(12) United States Patent
Kotula

(10) Patent No.: US 8,110,719 B2
(45) Date of Patent: Feb. 7, 2012

(54) ABI1 CONDITIONAL KNOCKOUT MOUSE

(75) Inventor: Leszek Kotula, Marlboro, NJ (US)

(73) Assignee: New York Blood Center, Inc., New York, NY (US)

( * ) Notice: Subject to any disclaimer, the term of this patent is extended or adjusted under 35 U.S.C. 154(b) by 0 days.

(21) Appl. No.: 12/430,814

(22) Filed: Apr. 27, 2009

(65) Prior Publication Data

US 2009/0271883 A1 Oct. 29, 2009

Related U.S. Application Data

(60) Provisional application No. 61/048,130, filed on Apr. 25, 2008.

(51) Int. Cl.
*G01N 33/00* (2006.01)
*A01K 67/027* (2006.01)
*C12N 15/00* (2006.01)
*C12N 5/00* (2006.01)

(52) U.S. Cl. ............... 800/18; 800/3; 800/21; 435/325; 435/320.1

(58) Field of Classification Search .................. 800/18, 800/21, 3; 435/325, 320.1; 325/320.1
See application file for complete search history.

(56) References Cited

U.S. PATENT DOCUMENTS 7,205,148 B2 * 4/2007 Economides et al. ........ 435/462

OTHER PUBLICATIONS

Wang, Cancer Cell, Sep. 2003, vol. 4, p. 209-221).*
Huang (Cancer Res., Aug. 2002, vol. 62, p. 4812-4819).*
Abdulkadir (Mol. and Cell. Biol., Mar. 2002, vol. 22, No. 5, p. 1495-1503).*
Zipfel, Current Biol., Jan. 10, 2006, vol. 16, p. 35-46.*
Lesche (Genesis, 2002, vol. 32, p. 148-149).*
Jenei (Orvosi hetilap, Jun. 12, 2005, vol. 146, No. 24, p. 1293-1299, abstract only).*
Ikeguchi (Oncogene, 2001, vol. 20, p. 4926-4934).*
Kasper (J. Cell. Biochem. 2005, vol. 94, p. 279-297).*
MGI website for PIN, 2010.*
Hoki (Human Mol. Genetics, 2003, vol. 12, No. 18, p. 2293-2299).*
Gyurko (Endocrinology, 2002, vol. 143, No. 7, p. 2767-2774).*
Macoska J.A., et al., "Loss of expression of human spectrin src homology domain binding protein 1 is associated with 10p loss in human prostatic adenocarcinoma", Neoplasia (New York, NY) Mar.-Apr. 2001, vol. 3, No. 2, Mar. 2001, pp. 99-104.
Ikeguchi A., et al., "Inhibition of v-Abl transformation in 3T3 cells overexpressing different forms of the Abelson Interactor protein Abi-1", Ongogene, Aug. 16, 2001, vol. 20, No. 36, pp. 4926-4934.
Maddison, L. A., et al., "Conditional deletion of Rb causes early stage prostate cancer", Sep. 1, 2004, vol. 64, No. 17, pp. 6018-6025.
Li, Y, et al. "Bcr-Abl induces abnormal cytoskeleton remodeling, beta1 integrin clustering and increased cell adhesion to fibronectin through the Abl interactor 1 pathway", Journal of Cell Science, Apr. 15, 2007, vol. 120, No. Pt. 8, pp., 1436-1446.
Yu, W. et al., "Abi1 gene silencing by short hairpin RNA impairs Bcr-Abl-induced cell adhesion and migration in vitro and leukemogenesis in vivo", Carcinogenesis, Sep. 2008, vol. 29, No. 9, pp. 1717-1724.
Echarri, Asier, et al., "Abl Interactor 1 (Abi-1) Wave-Binding and SNARE Domains Regulate Its Nucleocytoplasmic Shutting, Lamellipodium Localization, and Wave-1 Levels", Molecular and Cellular Biology, Jun. 2004, p. 4979-4993.
Shappell, Scott B., et al., "Prostate Pathology of Genetically Engineered Mice: Definitions and Classification. The Consensus Report from the Bar Harbor Meeting of the Mouse Models of Human Cancer consortium Prostate Pathology Committee", Cancer Research, Mar. 15, 2004, vol. 64, p. 2270-2305.
Suwa, Takahiko, et al., "Spontaneous Lesions in Control B6C3F1 Mice and Recommended Sectioning of male Acessory Sex Organs", Toxicologic Pathology, 2002, vol. 30, p. 228-234.
Van Der Neut, R. "Targeted gene disruption:applications in neurobiology" J. Neurosci. Meth. 71:19-27, 1997.
Kuhn et al. "Conditional Knockout Mice." Methods in Molecular Biology. 209:159-185, 2002.
Jorgez CJ, et al. "Genetic manipulations to study reproduction." Mol. Cell. Endocrin. 234:127-135, 2005.

* cited by examiner

*Primary Examiner* — Michael C. Wilson
(74) *Attorney, Agent, or Firm* — K&L Gates LLP; Louis C. Cullman; Michelle Glasky Bergman

(57) ABSTRACT

Genetically engineered conditional knock-out mice having conditional disruption of the Abi1/Hssh3bp1 gene are disclosed along with methods of making and using same.

9 Claims, 27 Drawing Sheets

FIG. 2A

SEQ ID NO: 19 - Abi1/Hssh3bp1 floxed allele

TCACTGCTCTTAACCACTGAGCCATCTCGCCAGCTCCCTCTTTCAATTCTTTAGGGTACAAA
TTATCCTTGCTTCATTTGTTTCTGCAATATCAAGCACTACTGCATGATGTACATCTGCGGTG
GTACCATAACTTCGTATAGCATACATTATACGAAGTTATGAATTCGTCGCCACCGCGAGAAT
TGATAGTTTTCAGGGTTTTAAATGAATTGGGGCATAAGTTAAGAAGGCAAAGTCTCTCTTAC
AAAATTGAGGAAGTCAGGATTCAGATTTCTATTTTTAATCGTTATCTGATTGGATGCCTTTG
ACTTACTGACTTTCCTAAGTAAGTTCTGCCAATTTTCAATGTTCTCATAGGAAAAATTTCGT
TGTCTAGATCAACTTGTGGCGCCATCTTCTGGGGCCTTAAGAAGACTCTCAAGATTTAAAAC
TGTATTGGTTTTTTTAAAGTCTTCCTAGTTTTTGGAAGTTCCTTAGACGCATGCGCCGGCCTA
GCCAGGAAGAAACTACAATTCCCAGAAAGCATTGCTATAGTGGATGGGTGGGGGACTCCCGT
TGTCATGGGGGGAAATGATTCTCGCGAGAAAGTGAGCCTGTGGCGGCTGTGCGTCCTGGGTGG
AGGGGGTGGGGGGGAGGAGGCGGGGAGAGTAAGGAGGAAGAGGAGGAGGTGCAGTCCCACAA
TACCCGGCGGAGCGGAGGGTGGGTGGTTGGCGTCTGGCTGTGCGGAGCTCGGGTTCCCGGCG
GACTCAGCTTCCTCTGTGTCTTTAATGCGAGAGGAAGCGATGCCGAGGGGTGGAAAATGGCA
GAGCTGCAGATGTTACTAGAGGAGGAGATCCCGTCTGGCAAGAGGGCGCTGATAGAGAGTTA
CCAGAACCTGACCCGGGTGGCGGACTACTGTGAAAACAACTATATACAGTGAGGGAGCTTGA
GCGGCCGGCGGGGGCCTGGACGACGGCGGCGGCCGCCGCGGCGATACAGGAAGTGGCCGCCTTGA
GAAAATGGGTGAGGAGCAGGGCCGCCGCGGGCGCCGGCTGACCCGATGCCGCTCCCCGcgtac
gccggcttaagtgtacacgcgtactagtctagcgaagttcctatactttctagagaatagga
acttcgttcgaacataacttcgtatagcatacattatacgaagttatggtacctgcagaatt
catgacataagcttggatccgttcttcggacgcctcgtcaacaccgtacgCAGCCTGCCCGG
GGCCGCCTGTGCTCCCCACAGCCTGCCCGGGCGTTGCTCCCTAAAGCCTACCCCGGCCGAGC
TCTGCTTCTCGCCGTCTGCCCGGCCCAGCTGTTGCTCCCCACCACCTGCCCTGGCTGAGGTCT
GCGCCTAAACCCCGCCGCTTTCC

FIG. 2B.1

SEQ ID NO: 14 - Abi1/Hssh3bp1 conditional allele

```
GTACTTTGCTTTTGGCTACACTTGGAGTTAGATTTTAAGATAAGTAAGTAAGGTAAAAATGA
AATGATTAGACTAGGGCCCTAATTAAATACAGCTGAGGTTTTTGTGTCATTATAAAAAGAGG
AAAAGATACAAGGGTTGGATATGTGAAGAGAAAATGCCGGGTGAGGGCACACAGATTATCAT
GCAAGGTGAGAGCCTCAGGAGAAACCTTGTTTGGGACTTGTGTCACCCAGAACTATGAGAAA
AACCTTTCTGTTGTCTGAGCTACCTTTCAGAGAGGGGAGAATGGGCGGTTCAGCTATAAAGA
CGTGTGAAGAAAGGCCATGTGCCCTGACTCTCTTACTTCTTCCTGAGTGGGTGCCTGCATC
ACTGAGGCTGTCATCAGACTTCAGATTCTCTAGCCTTGCAACAGGAATTGAATCCTTGTGGT
TCTCCAGGGAGCTTCCTGGACAGACTGCGGCTGCGCCTCCAGCCTTGTGGCCCAAGCAGTTG
GTGAGTTCTCTTCCTCTTCTGTGCCGACAGCTGTTGGTACACAACCCCCAACTTCTGTCCTT
TGCCAATCAAATAACTTTCTTACTGTTCTTTCGCTGTGAAGAAACACCATGACCATGGCAAC
TCTTAAAAAGAAAGCCTTTAACTAGGGGCTTGCCTATAGTTTCAGAAAGTTAGTCCATTAC
CATCGCAGGAGGGGAGCATGGCAGCAGGCAGGCATGGTGCTGGAGAGATAGCTGATAACTAC
ATCCTGATCCTTGGGGGTGGGGGGAGAGGGGGAGAGAGAGGAGGAAGGGGGAGGGGGAGAGG
GAGGAGAGGGAGAGGGAGAGACTAAGTCTTGTGTGGGCTTTTAAAACCTGAAAGCCCACCCC
CATTGACATATTTCCTCCAACAAGACCACACCTCCTAATCTTTCTATTGCTTTCAGACAGTT
CCATTCCCTGGTGATGAAGCATTCAAATATATGAGCCTCTGGGGGCATTCTTATTGAAACCA
TCACACTACACATTATGTATTTTCCTTTCAGTCTATTTCTCTACATAACCCTCCCTAACATG
AGAAATTATGCCATATGGGGATGGTGGCAATGCAAGTGGTGGGAGTATTTTGGAGGGTGCAG
GACAGATGGGGGAGTGGTTCTGCCTTCCTGACTGCTAGTTTCTTTCCAGTATATCACGTCGC
CATTCTGGATTCTAGCTTGCTGACCACCTACTTAGCATCCTGGTACACAGTGCTGTGAATTA
TCTACACAGAAAGTAAAAACAAAAAACAAACAGAAAGCAGAGTTCTGAAGTTTTTTCAGTGT
AATGTGCCAGATAATATCAGCAATTATGTACCAAAATAATCCAAATTATAATTTTTTTGCCT
GTCACATCACACATCTCTTTTTGTAGACATGATTTTTGATGAAATCATTTGTTTTGTAACCC
AGGCTGACTTCCAACAGGCAAATCTACTGGTTCAACCTCCCAAGTGCTAGAGTTGTAATGGC
ATATTACCAGGCTTAGCTACATAGCTGATCTCTTTATCTCTCTGAAGCAACGTCCATCATTG
TCAGCTATCTACTGTCTTAAAACTCAACCTGTAAAATGTTTTCCCATCTGTCCAGAATGTGC
ACTTCACAAACTTTTTTATTACCAAATTAATTTGCTTATGTCCATTAAAAGAAGGGTACAGG
TGCTAGGGAATCTAGCTTAGCTGGATTAGTGCCTGGTATGCATAAAGCCTAGCTTTAGCCCC
CAGCACTTCATAAAGCAAGATGTGGTGGCACATATCTGTAATCCCAGTACTGAGAAGATGGA
AGCAGGAGGATCAGTTCAAGGCTACCATTGGGTACATACTAAGTTTGAGGCTAGCCTAGACT
ACAACAGACTTTGTCTCATTAAATAAGTAAATAAATAAATGGTTGGATTTACAGGTTGAACA
CTGGCAAAAGTCATTACATTTAATACAAACACTGTTACTCTTTATTTTATTGCAATTTCATT
TTCTTTTATTTTATTCTGGTACGTGTGTGTGTGTGTGTGTGTGTGTGTGATCACATGTGG
GAACATGTGTGGGTACATGTACAGGTATACTTCCCTATAGATATCTTAAGGTACTATAGAAT
GTCTTCTTCAATCACATTCCATTTTACTTTTTTGTTGTTGTTGTTTTGGTTTTTCAAGACAG
GGTTTCTCTGTGTAGCCCTGGCTGTCCTGGAACTCACTCTGTAGACCAGGCTGGCCTCAGAA
GTCCACCTGCTTTAGCACAATACTCTTTAATACTTGCTTAAATGAGGCATGGCAGAAATCAG
CCTGTGATCCTAGCACTTGAGCCTTGGAGGATGGTTCAAGGTTGCTGGAGATAACTATGTTA
AGAGAAATAAATCAGGAACAGAAAGGGAAAAAAAAAAACACAGTGTTGTACTTAGCTATAGA
GAGGTTCAAGTCCACAGTGGATATGAGACCCTCTCTCAAGAACAAGCTAAGTTATTAGATGC
TATTAGTATTTTAACCTTGTCAAAAAAACAAAACAAAACATGGAAAGCCATCAGTTATAATG
TGGTACCTTGTCTTATGGTTATCTTCCTACAGGCTGGCTGTGAATGCAGGAAACTCCTTGTC
TCTAGCTCTCAGTTAGTTATTTTCTTCTTTTCTTTAGATTTATTTTGAGTGTTTTGCCTGTG
TGTATGTCTCTGTACCACACCCATGTCTTCTGTCTGCAGAGGTCAGAAGAGGGTTTCAGATC
CCCTGGGACTGGGAATTAGGAATAATTGTGAACCATTGTGTGGACACTAGGAACCAAAACAC
AGGTTATTTGCACCTCATTCTTTGGGATGTGTTGTTTTTCTTTCTTTGTTGTTGCATTGGCA
```

FIG. 2B.2

```
ATAGTTTCTCCATACGCTGTCTGTCTGGGACTTTTCTATATGCACCAGACCTTCCTCAAACT
TTCAGTGATCGTCCTGCCTCTGCCTCACCAGTGCTGGGCGACAGGTATGTGCAACCATGCT
AGCATTTAATTTCTTTTTGATTAGTATGCAAAGTAATGAGTTTCACTGTAACACTTTCATGT
ATATACTGCATTATATCCCGAGCTTTTGTCCCCGCCGGCAAGAACACACTCAGGACAACCGG
AATCTTCTGTGGCAAAGCTTTTATTGTTTACTTATCAGGAGGGAAGACCCCGAACCGGGAAA
ATGGCGCTGCTCATATAGCCCGCAGCGTGACGTTTCAGCACCTGATGTGGTGTGACAGCTCC
TGATTCATTGCTCGCCCATCACCCCATTACTACGCCGAGAGATGGGCAGTGACTAGGCGTGA
GTTCACTCTTGCACTTGCGCATAAGGCTTGTCTACTAGTTAGGCGCAGTGGAAGCCAGCGCC
ATCTTATAATGGTGATTGCTCACGGCACACACGCGATTGCTCGCGGCACGGCTCGGCTCTCC
ACAGCATTACATTGGTAACTTTATATATAATTATACTTTGCCATTCCACAACTACCTTCCTT
CCTCCTGCTGACTCCACCCCCACAGCCTGTGTTTGCCTTTATGTCACATGTCACATGCTCTT
TGTTACCTTTCCTTATTTGCTTATACTTCCCTTTAGACTTTCTTCTTCATGTTCACCACAA
GCTTCCTACCTTTGTGTTGTTCCTGCAAAACATGGCTTTCACCTCAAAGGCAATCTGAGATA
ACTTTCTTTTGTTACTGTTTTGGCTTTCTCTACTTTTAGACAGGGTATGTGTATAGTCCAGG
CCTCAAGCTCACCTGGTATCTGAGGATGACTTTGAACACATTTGTCACATTTGTTGTTTGGG
GGTTTTGTTTGTTCCTTTGTTTGTTTGTTGTTGTTGTTGTTTTTTTTTTTTTTTTGGTG
ACAGAGTTTCTCTGTGTAGCTTTCTCTTGCTATCTTGGACTTTGCTCTCCTGACCAGGCTTG
TAGGCTTGTATTTTTCAAAACCTATTTTAATAAGGGTTCTTCAATGCTTCAACCTGCCTTCT
AGCCCACTGACCAAAGGGAGGGGAGGAAAATGGCTAATAGGACAAGGGAATTGTGGACCTGT
TTAGAAGTAGTTTTTCGAGGGTGATTCCAGTCTTCGTTGTCAGCAGTCCAGTCCACTAGCAA
AACACCAAACACAAATCAGCAGCAGCAGTTCCATCTAGAAGAAACCTCAAGGCTTCCCTCTA
CTCAGTGCACAGAAGTGGCAAGAAGCAGCCAGAGCACCAACAGAAGTTCTTTGGTGCATTTC
TCCCACAATGTCACAATAAGCAAAGATCAGAGATGAAAGCAAGGTGAGTGAATACAAGAGTG
TCATCTTCAAAGACCAGCATTAGGGAAACCCAACAAAGACCAGCAAGGAAACCAATGCTGGA
GCAAGGTCCACTGTCTGTTGGGTTACACTTATACTCTTTCTAAACATCACATGTCCTCCCAA
GCGTCTACTACAGCAAAACATTACATGCCCTTTCACCAGGCAGCTTCCAGAAAAACACCTCC
TGTCTGTTCTCAGCAGAACATCCTCTCATAAGACAGCGTCAGAAAAACATCACATGACACAA
CTAAGTCTCCAATGAAACCAGATATTCCCACTTCAAGGCTGGTCTCGAACTCACAGAGATCC
ACCTGCCTCTGCTTCCCAAGAGCTAGGATTAAAGATGTGTGTGCGTCACCATCCAGCAACCT
TGAAGTCCTGATCCTCCTGCTTCCACCTCCTGAGAGAGAGATTACAGAGAGAGAGAGGCGGG
GGAGAGGGAGAGGGAAAGAGGGAGAGAGGGAGAGAGAGAGAGAGGGAGAGAGAGAGAGAGGG
AGAGGGAGAGAGGGAGAGGGAGGAGAGGGAGGAGAGGGAGGAGGGAGAGAGAGAGAGAGAGA
GAGAGAGAGAGAGAGAGAGAGAACTCTTAGTTGGGGTTGCCTTACAGTTTCAGAGGTTTA
TCATCTTGGCAGGAAGCATGTAGTCATGGTGCTGGAGAGGTGCTGAGAGTTCTACATTTTGA
TCTGTAGGCAGCAGGAGACTGTGTCACACTGAGTAAAACTTGAGCATTTTTGAAACCTCAAA
GCCTGCCTCCATAGTGACACACTTCCTCCAACAAGGCCACACCTTCTTCAATAAAGGTCACA
TCTCCTAATAGTGCCATTTCCTGTAGGCCAAGGATTCACATATATGAGTCTAGGGGACCAT
TCCTATTCAAACCACCATGGATATGTTCTTCCTTGGAAACAGTTATATGCATGTCTAGAGCT
GTTATTAGTTATAGAAACAGAGAAAATACTAAATCGATGTATTTACCAGATACAGAGTGGGG
AAACTTAGGAAGGAAGGCCATAGCCAGTAAGGTGAGTGAATTCTGCTACCTACTCAGACACT
ATGTGGCTGCATTCTTAACTTTCAGATTGATAGACATGAATCTAAAAGCCTAAAAGCCATTT
CAAAAGTTTTATCTGAAACTCAAAAGGGCATTAGGTCAGATATAGGAATGAGAAATAAATGG
ATATTAAGGGTAACTAAAAATAGGAGCTGGAGGGGTCTGGAACTGTCTCTAACACTGTTGCC
TGTCTGGGGACCCTTTCCCATAACTGGACTGCCTCATCTAGCCTCAATAGGAGAAGATGCGC
CTAGTCTTACTGAACTTAATATGCCAAGGCTGGTTGATATCCATGGGAGGCCTGCCCCTTCC
TGAAAAGAAAGGGGGAGGACTGGTGAGGGTGGGAAGATTGGGAAGGGAAGAGGGAGGAGAA
ACTGTGGTTGGAATGTAAAGTAAATTAATTAATTTTAAAAATAGAGGCTGGAAAAATGGCTC
AGCAGCTAATGACAGTGGACCCAGATTTGGGTATATTCCCAGCATCCATTTGGTGGATAACA
ACGGTCTGTAACTCCAGAAGCTTGGATGCCCTCTCTGTCCTTTGCTGGCACCAGCCACGCAC
GCACATACAGTAGACATATGCAGGCAAAACAGACATAACTATAAAAGGTAAATAATAGCACC
ATTTTAAAAGAAAGGGCACTACAAATAGCTAAAGAAAAAAAAATAGCTAAAGAATTTTTGCT
```

FIG. 2B.3

```
TTGTTTTGTTTTTGAAGACAGGGTTTCTCTGTGTATCTCTGGCTGTCTTGGAACTGGCCCTA
TAGACCAGGCTAGAAAGACTACTGCTCAGAGATCTGCCTGCCTCTGCTTCCTAAGCACTAGG
ATTAAAGGTAAGGGCCACCATGCCTAGCAGCTCAAGATGATGAAACTCAAATAAATCATATA
TTCATTTACAACCCTCAACACAGCATAGCTTGGTTGGGTCTTTTTCTGAGTGTTTCCATTTA
CAGTGTCACACACACACAAATTTAACTGTGTATTCTGCATGTGAGAGAAATATGACATG
TGTCTTCCTGAGTCTGACTCATCCAGTCTATTTCATTCTTTTCATCAACTTTTCTTGCAAAT
GTCAAAAATTCACCTTTTTTCCCCTAGCTCAATAAATTTTTTGCCGTTTATTGTTGTGAGGT
GGTTACCAGAGAAGACTGCTCAGACAAGGGATGAAGCCTATTGCAATGGTTTGTCTATGCTC
AGCCCAGGTAGTGGCCTTATTAGAAGTTGTGATCCTGTTCGAGTAGGTGTGGCCTCATTGGA
GTCAGCATGGCACTGTGAGTGTGGGCTTTAAGACCCTCATCCTAGCTGCCTGGAAACCAGTA
TCCTGCTAGCAGCCTTCAGATGAACATGTAGAACTCTCAGCTTCTCCTGCACCATAGACACT
GCCATGCTCCACCTTGATGACAATGAACTGAACCTCTGAACCTGTAAGCCAGCCCAATTA
AATGTTGTCCTTATGAGAGTTGTCTTGGTCATGGCGTCTATTCACAGCAGTAAAACCCTAAC
TAATACACCTATATAAAGTCTTTACTAGCTGACCAGTGACCCCAGTATAGTCCCGACCCTGT
TTTGGGGTGAGCTTTTAAGCACAAAAACCATATCCTGGGTTGACACACTTCTGTTAACAAGA
AGAGTTAACCAGAAGCAGGACTACAGAAGCCAAAAAGCAAGGTGAGAACATTTAGAGTCATT
CTCATGACTATGGACTTCGATGGATCAGGTCTTTGTTTTACTTTTGGCAGGTGGTGCTATGT
GCTAAATTTCATAGCCTGACTAGTATTTCCACCACGGAGTCAATTGTGTTAAGTTCTCAGGG
CCTACTAAGATCTAGGGCCCTGTTAGCTAAATATGCCTGTGTCCCTCCTTGCCCCCAGGGAT
TCTTGGCTGATAATGGTCCTTAAAAGCATCAGAAGCCAGGACCAGCTGTGGGGAGGCAGATC
AACTTTACTTAATGTGACACAAGGTTTATATAATCTGGGGAATGTGAGCAGGGTCAGATTAG
CTGAAGGCTTAAGATACCAAATGCCTCTTTTTTTTTTTTTTTTTTTTTTTGAGACAGGATA
TCTCATTACTCAAAGCTCACCAATTAGGCAAGGTTGGCTGGCCAGCAAGCCCCAGTACTTTC
CAGCAGCACTGGGACTATAAGTGTGTGCCACCAAGTCTGGAATTTTTTTTAATAAAAAAAT
ATGGGTCTCAAATCCAACTCAGATTTGAGACCTGTTTGCCAGGCAAGCACTTTATTGGCCAA
ATCATCTCCTCAGTTCCTAAACAGAACTTTTTTTTTTTACTCATTCCCGTGTACTTTAATAT
TGTTACCTCAAAGGATCTAGAATGGAAAATGGCAAACCTCTGGGCATGTCTATGACAATCTG
CAGATTAGGTGAGCAGAGACCAGAAGACATGCCTAATGTGTGGGAGGCACTGTTCCCTGGAC
TGAGAACCTAATCTGGATAAAAAGAAGAAAGAAAATTGAACACCAGCATCCAACTCTTTTGT
CTCCCTAATTGCATAAACAATGTTGCCAACTACCTCCTACATCTCCCACTCTGCTTCTCACC
AGGGTGGACTCGATCAGCTTGAACATAAAATAACAGCAAGGATTTTTTTCTCTCCTAACTT
AATTCTTCTCAGGTGCTTGTTTACACTGATGAGAAAAGCACCCATGTGGGTCAGTGAGATA
GCTCGGCAAGGAAAGGTGCTTGTATTTCAAGCCACATGACCTGAATTTGATTTGATTCTGGG
ATTTACATGGTAGAGAGATTCACCTTCTCCTTAAATTGTCCTCTGGCTTCTACACGTTTTCC
ACACATGCAAGCTCTCTCACACATACACATAGTTACACACCCATACCAGGCACATATACACA
CAAGATAAATAAATAAATAATGTTATAAAAATGTTTAAAGAAAGAAGGAATGGAGATTTAAT
TAGGGAGAGGATAAATTAATACAGAAGAAAGAGGGTAAAATAACCACTAAGGTGTCTGAAAA
ATCTTAAGAAATCATTTATTACCAATATACCTAAAATTACATGTAAGCCTGCATATACATAT
ATAGTTTAAATGATATTTGCCCATCCAGGGTGACAATGTCTTTTCCCTGAAGAGTCATAAAC
AATGCCCCAACACCAGGCATAAAAACCCTTTTTTGTTTGTCAAGATTGTCCAAGAGTCTCCC
AAAACATTTCAGGCTATTTCTGTGCCTTTGGTTGCCTCCCAGAAGTTGAAGATAAGTCTCCA
TTGCTAAAGATAACCTAGGTGTCTTTAATCCCATCACTTGGAAGGGAGAGGAGGGGGATCT
CTGAGTTCGAGGTCTGCTTGGTGTATAAAGCAAGTTCCAGGACAGTTGGGGCTACCCTGTCT
TGGGGTGGTGTCGGGGACGGGACTACACCATATGCTTCAGACATCTGACCCAGCTGATCTGA
ACTCTTTGTGATCTGAAAGCCTCCTTCCTGAGGACAAGCTTTCATGATACTAGAATGTGCCA
TGCACGCACGCTTCCAAGGGAAGGAAGTGAGCAATAATTCTACCCAGCTGTGATGCCTGTAG
AGGGACATTGTACAACAACCCTAAGGATGCAGTAGTGGAATGAATAGTTAGTGGTAATCAGG
AGCTTTCTGTAGGCTTATATATATATTTTAAAAATCTATTTTAATAAGGGTTCTTTAATG
CTTTAGCCTCCCTTCTAGCCCACCACCCATCAGAAGTAGTGGAAAGGAAAGGTTCATGGGGC
AAAGGAGGATGCGCTCTTGTTTAGAAACAGTTCTTTGGAGCAAATCCAATCTGCTTTGTCAG
CAGGTCACTGGATCCACTCACAAACATCAGTCTCTTTTTATTTTTTTTTTAAGAATTATTA
```

FIG. 2B.4

```
TCGCTTCTCGGTCTTTTGGCTAAGATCAAGTGAAGAATTATTTATTTATTTAATGTTTATTT
ATTTATTTTATGTACACTGTAGCTATCTTCAGACATACCAGAAGAGGGCATCAGATCGCATT
ACAGATGGTTGTGAGCCACCATGTGGTTGCTGGAAATTGAACTCAGGACCTCTGGAAGAGCA
GTCAGTGCTCTTAACCACTGAGCCATCTCTCCAGCCCCAACACCATTAGAGTATCAGCGATG
GCAGTTCGATCCAGAAGAAATCATAAGACTCTGCCAACCTGCCTCAGTCCTTGGAAGTGGCA
AGAAGAAAAACCACCTATGAAGTCACATCAAATGATGACCAGCAATGGATGGCAAGGTGAGC
CAATACCATACAGCATTGTCCACTGTCTGCTAGGTTATATTTATACCCTTTCTAAACATCAC
ACGTTCTCTCAAGCATCGGCTCTAGCAAAACATCACATACCTCTTTTCCAGGCTGCTTTCAT
AGAAACACCACTTCAGCTTTCTAGACAGATTATATTCTTACTCATCAAAAGAGAAGTCATGC
CTGGCACTGGAATCCCAGCCCACTAGCCAGGGCTAATGAACTCATGGATCTTGGAGGAAAAC
CTACAACCACCACTTTACTAAACCAGCATAATCCATAACTACACTCTAAATATGTTTCCTAT
GCCTGTAGGTAAATGTAGTTCTCACTCTTCAAGCAGGAAATTTCTCCTTGCCTCATACGAAG
ACCATTACAGAAAACCAGAACTGATATAACCCTGTTTTCGAGACAGGGTTTCTCTGTGTAGA
CCAGGCTGGCCTAGAACTCAGAAATCTGTCTGCCTCTGCCTCCCGAGTGCTGGGATTAAAAG
CATGCGCCACCACCCCTGGCTGGAGAGATCACTTTAGAAGAGGCAGATTGTAAGAGCCAGAG
GAACCCGAAGCTAGCTGTGAGATTTCACCTCCTAGAAATGACAACCAAAGTGTGGACACTTT
GCCCCTTCTTAGAATTGGAAACAATCACCCATGGAAGGAGTTACAGAGACAAAGTTTGGAGC
TGAGACAAAAGGATGGACCATCTAGAGACTGCCATATCCAGTGATCCATCCATAATTAGCC
TCCAAACGATGACACCATTGCATACACTAGCAAGCGTTTGCTGAAAGGACCCTAATATAGCT
GTCTCTTGTGAGACTAGGCCGGGGCCTAGCAAACACATAAGTGGATGCTCACAGTCAACTAT
TGGATGGATCACAGGGCCCCAATGGAGGAGCTAGAGAGATCTGCAACCCTGTAGGTGCAAC
AACATTATGAACTAACCAGTACCCCGGAGCTCTCGACTCTAGCTGCATATGTATCAAAAGAT
GGCCTAGTCGGCCATCACTGGAAAGAGAGGCCCATTGGACACGCAAACTTTATATGCCCCAG
TACAGGGGAACGCCAGGGCCAAAAAGTGGGAATGGGTGGGTAGGGGAGTGGGGGGAGGGTAT
GGGGGACTTTTGGGATAGCATTGGAAATGTAATTGAGGAAAATACGTAATGAAAAGAATATT
TAAAAAAAAAAAAGAAATGACAACAAAGCCTCACCCACTAAGTTTCATCAACATGGCTATCT
AAACAAGACCTGAATTAGAACAGGAACAGATATTATTAACAGGAAGAGGAAATCTCATCCAC
CCTCAACCCTTGACAAAGAGCTATCGGAAGCTAGCAAGAGAAATAGTCATTCCCAAGGAAGA
GCACCCGAACTGGATATCCAATGTCAAGGTCAGCCTTGACATAATGTACATACATATGGATT
ATAGAGACTGAGCAGGTAGGTTTACATGTTTTGGAAGCTATACACATACACATATACATACA
CATACTAATTTAAGAAATAGAGGTCATGATTTTGAGAAAGAGAAAATGGGGGGCTACATAGG
GAGAGTTGGAGGAAGAAAAGCAGGGATGCTATGATTTTATTATAATTTAAAATTATATATTA
TATATAGTTATATCTTAATTAAAATTATAATATATAAATAAATGAAGGGGGACAGGAGAGAT
GGCTCAGTGCTTAAGTGCATGTATTACTTTTGCAGAGGACTGGAGAACAGCTCTGAGTCCTC
ATGTTGGGTACCTCACAAGTGCCTATAACTCTAGTTCTAGGGACATGTACTGTGTTTAGTCT
CAGCAGGCACCTACACTCATGTGCACACACCCACAAACAGACATACTCTCACACGTGTAACG
TTTTAATATTTGGGAGGAACAAAAGGAAACAAAGAAAAGTAACGAATGCAGTCCTTCTCGAT
GAACACCTGTGGAGGGCCCAGATCTTGGCTGTTGAGAACAGCAATAAACACAGATGTGCATG
TATCTCTGTGGTATGTAAACATACAGTCCTTTGGGCATATACCAGGAAGTGGTGGGGCTGAA
TCATATGTTAGTTAGCTCTATTTTTAGCTTTTTGAGGAACTTCCACCCTGGTTTCCATTGTG
GCTGAACTAATTTACATTTCTGGTACCAGTGTCTAAGATTTGCCATTCCCCATGTCTTTGTC
AATATTTATTGTCATTGTTTTCAACAACAATTTCCAAAAGTTTGCTGAGTACTGTTGTTACT
TCAAAAATTGTGATTCTCAGTGAGTCCCAGAGAGGACTGGAAATATAGGTCTGTAAATAATA
TTTAAATTTAGGCAACTCTTTTCATAGCCTATTATTTCAAAATAATTTAATAGTTCTGGTGA
TATGACAGCTTGAAATACTGTCAAAGACCCTTTGAGACATTTGCAGAGCAAGTGATAAGAAA
TAAGAACAAAACAATTTTGTACAATGCAAGACAAAAACTCCTCCTCCTCCTCCTTCTTT
CTTATTTTTCCTCTTCTTCTGTAGTTTCTCCTCCTCCTCCTCCTCCTCCTCCTCCTCCTGG
TTTTTCAAGACAGGGTTTCTCTGTGTAGCCCTGGCTGTCCTGGTACTCACTTTGTAGACCAG
GCTGGCCTCGAACTCAGAAATCCCCCTGTCTCTGCCTCCCAAATGCTGGGATTAAAGGCGTG
TGCCACCACCATCCGGCTTTCTTTCAATTCTTTTTTTTTTTTTAAAGATTTATTTATTTAT
TATATGTAAGTACACTGTAGCTGTCCTCAGACACTCCAGAAGAGTGGCATCAGATTTCGTTA
```

FIG. 2B.5
CGGATGGTTGTGAGCCACCATGTGGTTGCTGGGATTTGAACTCGGGACCTTTGGAAGAGCAG
TCACTGCTCTTAACCACTGAGCCATCTCGCCAGCTCCCTCTTTCAATTCTTTAGGGTACAAA
TTATCCTTGCTTCATTTGTTTCTGCAATATCAAGCACTACTGCATGATGTACATCTgcggtg
gtaccataacttcgtatagcatacattatacgaagttatgaattcgtcgccaccgcGAGAAT
TGATAGTTTTCAGGGTTTTAAATGAATTGGGGCATAAGTTAAGAAGGCAAAGTCTCTCTTAC
AAAATTGAGGAAGTCAGGATTCAGATTTCTATTTTTAATCGTTATCTGATTGGATGCCTTTG
ACTTACTGACTTTCCTAAGTAAGTTCTGCCAATTTTCAATGTTCTCATAGGAAAAATTTCGT
TGTCTAGATCAACTTGTGGCGCCATCTTCTGGGCCTTAAGAAGACTCTCAAGATTTAAAAC
TGTATTGGTTTTTTTAAAGTCTTCCTAGTTTTTGGAAGTTCCTTAGACGCATGCGCGGCCTA
GCCAGGAAGAAACTACAATTCCCAGAAAGCATTGCTATAGTGGATGGGTGGGGGACTCCCGT
TGTCATGGGGGAAATGATTCTCGCGAGAAAGTGAGCCTGTGGCGGCTGTGCGTCCTGGGTGG
AGGGGGTGGGGGGGAGGAGGCGGGGAGAGTAAGGAGGAAGAGGAGGAGGTGCAGTCCCACAA
TACCCGGCGGAGGGAGGGTGGGTGGTTGGCGTCTGGTCTGTGCGGAGCTCGGGTCCCCGGCG
GACTCAGCTTCCTCTGTCTCTTTAATGCGAGAGGAAGCGATGCGGAGGGGTGGAAAATGGCA
GAGCTGCAGATGTTACTAGAGGAGGAGATCCCGTCTGGCAAGAGGGCGCTGATAGAGAGTTA
CCAGAACCTGACCCGGGTGGCGGACTACTGTGAAAACAACTATATACAGGTGAGGAGCTTGA
GCGGCCGGCGGGGGCGGCTGGGACGACAGGCAGGCTGGGCGCCGTGGGACTGCCCTACTCC
GCCACCCTCCGCCCCAGCCCGAGCGGCGGCCGCCGCGGCGATACAGGAAGTGGCCGCCTTGA
GAAAATGGGTGAGGAGCAGGGCCGCCGCGGGCGCCGCTGACCCGATGCCGCTCCCCGCGTAC
GCCGGCTTAAGTGTACACGCGTACTAGTCTAGCGAAGTTCCTATACTTTCTAGAGAATAGGA
ACTTCCCGCGGATAACTTCGTATAGCATACATTATACGAAGTTATGTCAGCTTCTGATGGAA
TTAGAACTTGGCAAAACAATACTGAGAATGAAGTGTATGTGGAACAGAGGCTGCTGATCTCG
TTCTTCAGGCTATGAAACTGACACATTTGGAAACCACAGTACTTAGAACCACAAAGTGGGAA
TCAAGAGAAAAACAATGATCCCACGAGAGATCTATAGATCTATAGATCATGAGTGGGAGGAA
TGAGCTGGCCCTTAATTTGGTTTTGCTTGTTTAAATTATGATATCCAACTATGAAACATTAT
CATAAAGCAATAGTAAAGAGCCTTCAGTAAAGAGCAGGCATTTATCTAATCCCACCCCCACC
CCCACCCCCGTAGCTCCAATCCTTCCATTCAAAATGTAGGTACTCTGTTCTCACCCTTCTTA
ACAAAGTATGACAGGAAAAACTTCCATTTTAGTGGACATCTTTATTGTTTAATAGATCATCA
ATTTCTGCAGACTTACAGCGGATCGATCCCCTCAGAAGAACTCGTCAAGAAGGCGATAGAAG
GCGATGCGCTGCGAATCGGGAGCGGCGATACCGTAAAGCACGAGGAAGCGGTCAGCCCATTC
GCCGCCAAGCTCTTCAGCAATATCACGGGTAGCCAACGCTATGTCCTGATAGCGGTCCGCCA
CACCCAGCCGGCCACAGTCGATGAATCCAGAAAAGCGGCCATTTTCCACCATGATATTCGGC
AAGCAGGCATCGCCATGGGTCACGACGAGATCATCGCCGTCGGGCATGCGCGCCTTGAGCCT
GGCGAACAGTTCGGCTGGCGCGAGCCCCTGATGCTCTTCGTCCAGATCATCCTGATCGACAA
GACCGGCTTCCATCCGAGTACGTGCTCGCTCGATGCGATGTTTCGCTTGGTGGTCGAATGGG
CAGGTAGCCGGATCAAGCGTATGCAGCCGCCGCATTGCATCAGCCATGATGGATACTTTCTC
GGCAGGAGCAAGGTGAGATGACAGGAGATCCTGCCCCGGCACTTCGCCCAATAGCAGCCAGT
CCCTTCCCGCTTCAGTGACAACGTCGAGCACAGCTGCGCAAGGAACGCCCGTCGTGGCCAGC
CACGATAGCCGCGCTGCCTCGTCCTGCAGTTCATTCAGGGCACCGGACAGGTCGGTCTTGAC
AAAAAGAACCGGGCGCCCCTGCGCTGACAGCCGGAACACGGCGGCATCAGAGCAGCCGATTG
TCTGTTGTGCCCAGTCATAGCCGAATAGCCTCTCCACCCAAGCGGCCGGAGAACCTGCGTGC
AATCCATCTTGTTCAATGGCCGATCCCATATTGGCTGCAGGTCGAAAGGCCCGGAGATGAGG
AAGAGGAGAACAGCGCGGCAGACGTGCGCTTTTGAAGCGTGCAGAATGCCGGGCTCCGGAGG
ACCTTCGCGCCCGCCCCGCCCCTGAGCCCGCCCCTGAGCCCGCCCCGGACCCACCCCTTCC
CAGCCTCTGAGCCCAGAAAGCGAAGGAGCAAAGCTGCTATTGGCCGCTGCCCCAAAGGCCTA
CCCGCTTCCATTGCTCAGCGGTGCTGTCCATCTGCACGAGACTAGTGAGACGTGCTACTTCC
ATTTGTCACGTCCTGCACGACGCGAGCTGCGGGGCGGGGGGAACTTCCTGACTAGGGGAGG
AGTAGAAGGTGGCGCGAAGGGGCCACCAAAGAACGGAGCCGGTTGGCGCTACCGGTGGATGT
GGAATGTGTGCGAGGCCAGAGGCCACTTGTGTAGCGCCAAGTGCCAGCGGGGCTGCTAAAGC
GCATGCTCCAGACTGCCTTGGGAAAAGCGCCTCCCCTACCCGGTAGAATGAAGTTCCTATAC
TTTCTAGAGAATAGGAACTTCGTTCGAACATAACTTCGTATAGCATACATTATACGAAGTTA

FIG. 2B.6

```
TGGTACCTGCAGAATTCATGACATAAGCTTGGATCCGTTCTTCGGACGCCTCGTCAACACCG
TACGCAGCCTGCCCGGGGCCGCCTGTGCTCCCCACAGCCTGCCCGGGCGTTGCTCCCTAAAG
CCTACCCCGGCCGAGCTCTGCTTCTCGCCGTCTGCCCGGCCCAGCTGTGCTCCCCACCACCT
GCCCTGGCTGAGGTCTGCGCCTAAACCCCGCCGCTTTCCCCGCCAGGGATCTGTTTCCTGCA
GCCTTCCCAGGCCGGGACGTGCTCCCGGCAGTCTTTCCTTCCCGGTCTCCGCTCACTGCAGG
CCGCTCTTCTTAGTCGGGCTGTATTCAGCTTTGCCTCTTTTGGCTGCGGTTGGTTCCTAAGA
CCCCCCACAGCCTTCCCTGGCTGGGGTCGGTCCTGGCTGAGGTCCCCCTGGAAATCCCGCAG
CCTCCCTTGGTCTCCTTGGAGCTCAGACTTCGCTGTCGCCCCATGTCCGGTGTGATGAGCC
TAGGACTGGGACAGCTGCGAGAGGAATGGGCAGGGAAGGAAAAGTGGGGTGTGTGTGTCG
TTGGAGGGTGGGGTGAGGGTGATTATGTCAGTTCATCCTAGAGGGTGTGCCTTTTATTTATT
TAAAAAAATTGTCACGAGTCACATTTGTACAGACCTCCTAATCGAGTGCGGAGAGTGACTGC
TGAGGGTGTGATAAAATCCATATTAAAATTCTTTTAATTGAAGGAAAAATGCGTGCTTGGCG
ATTTTCAAGTTGGGCTTTTCCTCTTCCACCTCCTCATATTTACTTCCGCTTTAGCATAATGT
ATACTCGTTATTATAAAGCACGAATGATTCATAGGGAAATTCAGTGGGAAATCTGTTAAATA
CTTTTCTTCCTCTAAATGTTCTTGGACTGTTGGCCTTGAACGCAGTAGTGTTATCGTGGTTG
CTTATGTTCTGAGATTTCTTTCTATACTGAGTTAATACATAGAAGAATATGAATAAAGTAGA
TTAGCAAACATTATGTAGTCTTTAAGTCATAACATAGAATTGCTCCTTAATTTATCAGGAAA
TTCTTGGCACTTTTACTATGCCATGCTTGCTTGTGTTTATCAGCGATTGTAAGTGAATTGTA
TGTAGTAGTTTGACTTGTCCCTATGGTTGAGTAAAAATTAACAGTTTTCACTAGAAGCAAAT
ACAGTAGTGGAATTCTTTGTATCAGATAATGAGAATAGAAATTCATTTCTTGTTGATAAGGC
AAAACCAGAACAGTCTTTGAAAAATAAGGAATATTGTACTTTGGACCTGCAGTATTTCTTAA
AGTGCCTTTCATGTGATTATCATTTTCAAGAGCGGCTAATTTCTGTTCTAGCAGATTCCTGT
AGATTTTGTTTTCAGAAGGAGATGCTGTCTTGAGACTTGTCTGAGTATTTGTCATTTTCCAT
ATTAGTAACATTCTATCTGGAGTGGTACTCCAAGGAGTTTGTCTTCCTACTCTCGTTTCCAG
CCTTTGACTTTGGTAATCTACTCATAAACTTGTTGAATGCTTCCTGTGTCTTCTGTATAACT
TGGTTTTGAAAACTATATGGCTGTTTAAAAACACATTTTAAGCAGCAGAAGGGCTGCCTTAA
CCACTGTTAAGAGCAGTTGGTGCTTTTGCAGAGGACTCGGGTTCAGTTCCCAGCGCCCTCAT
AGTGGTTCACAGCCATCCTTATCCTAGGGGGTCCGTGTCCTCTTCTGACACCTGTGGGCACC
AAACACACATTCAGTACACATACACACATACACACATGCATACACATAGGTACGATGAGTGA
GTTTAAACCTATTTCAAAATCATACAGAAATGTGGATATAGTGTGGAAATAGAAAGGTGATC
TTGTATTTTATAGATACTAAAAAATGTACATCTTTTATTTATTTTAGTATGAAAAACCTTGG
GTTTGTTGCATCTTTGGTTCCCAGCACTTGTATGAGGCAGGTTACAACTACCTCTAACTCCA
GCTTCAGGGGATCTAACACCCTATTCTGGATGTATGGGGTCCTGCACTCAGGAGTGCATGGA
CACATCCACAAACAATTAAAAAGTGGATAGACACACAATTTAAAGCAACCCACTTTAATTGG
TAATAGTGCTGATTAGGATAAGTAGTTGTGCTATTTGTTTTTCTTTGTGTGTAAAGTTTGCG
TTTGTTTTCAGACACAATCTCATTCTAGACCAGGCTGCTGACTTTCTATCCTCTTGTCAGCT
TCCAGGTGCCATGCAGCTGCCATACCCAGCTGAGGTGGGAAAGGGTTTTTATGGGGGTGAG
ATGGGGGACAGGGTCTTATTATGCCATCTTGGCTGGTCTGGAGCTTATTACATAGACTAGGC
TGGGTGACAGAGATCTCTCTTCTCTGTCTCATCTACTGAGATTAAACATGAATCACCATGCC
TGAGGAGAAAAATTGTCATACTTACTGTGAGACGATTGCTGTGTGTTTTACCATGATAATTA
TTTTGTTGTTTTCTTATGTTTGGAAAATTCAGCCCTGTTTGCTGAGAAGTTATTTTGGCTAG
TTCTTGGGCTTTGGGCCCTGCTGAGTTTAGTACTTAAACTGAGTTATTAAATGCAGATCTTA
TTGAAAGCTTCTTCAGCTCCTTAAAAAGAATGGAGTTTTAAAGTTATGGGGTGAGGCTGGAG
AAACAGCCACACCAGAAGAGGGTCCCATTACAGATGGTTGTGAGCCACCATGTGGTTGCTGG
GTATTGAACTCAGGAACTCTGGAAGAGCAGTCTGTGCTCTTAACCGCTGAGCCATCTTGCCA
GCCCTATTTTATTGTTTTAAATCATATGTATATATGCGTGCTTCTGCTGGGCATATGCACA
TGAATGCAGGTGCCTACACAAGCCAGTGGCATCAGATCTCCCTGGAGCTGGAGTTACAGTTG
GTTATGAGCCTCCTGATATGGGGCTGGGAATCCAATTTGTGTCCTTTGGAAGAGCAGTCTG
CACACTTAACTGCTTAGCTCAGAGAAAAGCCAGCTCTAAAGTACAAACCTACCTGCTCTTCT
GTTTGCAGCTTAGAACTTGGAATGTATTTTCAAAAGAATGGTTGCTGGAGCTGTCAGGTTCC
CATACTGGTCCAACAGGTCTACTTACTCTAAGAACATTCCTGAACTAGTCTGAGGTCTAGAT
```

FIG. 2B.7

```
TCTCATGAAAACTGTGTGATATACAAACTACTCTACCCACTTGTGGAGTCTGTCACACCTAA
GGAATCTGCCAATCACTAAATGTATAGCCAAGCAAAATTTATTTAACTTTCCTGTGTCTAAA
TTTTCTTACTTATATGAGGGCACTCCCTATGACAGCCAGCATATAAGGATTAAATACAAAGT
AGAAAGATTACAGCACAATAGAAACTCAATAAACAGACTCAATTAAGACTGGTTCTCCATAT
CTGTGTGATTCGACAATCATGTATTAAACCTACTGCTGACCCAATGTGCTGCGCAGATTTTA
TTGTCACTCTTCCCTAAAAACTATTGTGTGTGAAAACTTAAGAATTTAGGGTCAGCATCTAT
AGCACAGAGGGCAGGAATAGTGAGCAGTTGGGTAGATGGATTCAGCACTAAGGAACAAAGAT
GGGCTTCTCTCTCAGACTTCTGTATAGCTGGGTTATTGCTGGAGGGTCTGTCTATTTTAGGG
AGGGGTTTTCTGCTCAGTCAGTAGGATTTTCTTTTCAAAGTACATCATTGAAAGGATAATAG
GGAAAATAACAATGCACTTTGATAAAGAAATAGTTGACTTGATAATTTTAACAGTATACGTA
TATAGTGGACTTTGGGGTTGCTTTTAGTGGTACTACTCTGTTGACCCAAATAAGTTTACCC
TTGGCTCTGTTGATTTTTCTCCACTTATAAAAATTTTAGAATTAATTGCAAGTGTATCCAT
GTTCATAACAAGAATCTGAAAGCAAATAGAACATCTTAAGAAAGGTAATGTTTTTGTCGCTA
AGTGATGTGATGGCCTGGTGTGATGACTGTTGCCTGTAATCCTGTGGTAGGAGGATCACTAG
GAGTTCATGGCAGCCTGTTGAGGTACAGAGTGATCCAAGTTAGCCTAGTCTAGAATGAGACT
CTGGCTCAAACAAATGACAGAAGAATTAGCTGTAAAACTAAGTTCCTTCTTTTCCCCACTTT
ATCTCTCCCTTCTTCCTCTCTCTCTCTCTCTCTCTCTCTCTCTCTCTCTCTCTCCTCTCC
CTCCCTCCCTCCCTCCCTTCCTTCCTCCCTCTCTCCCTTTCTTCCCTTTTATTGTAGCCCAG
GCTGATTTCTAACTGGTAGGTAGTTGAGATTGACCTAGAATTCCTTTACTGCCCCTATCTTC
CATATTCTGTGCTATGCAGCTGTGTGTGATTCTTCACAACTGTGTTATCCTACTTGTTCCTA
TTCCTGCCCCAAACTACCACTAGTTCATCTTGGGTGTGTGTATTTGTGTTGGGAGGGAGAGA
TAGAAAGAGATGGATAGATGGATTCATGCAGATGCCACAGTGCCCATTTGGAAGTCACACAG
CCTTTGACGGTTTGTCCATTCCTTTTACTGTGGTCTGATGATTATTCTGGGTTTCAGGTTAT
TAGGCTTTCACTGTCCAGCAGTTTCTCTGCTGAACTATATTTCAGCCTCCCTTCATCCCCAT
TAATTCTTCTTAAGTGGCTTAAATAATTCCTTTTGTTTTATTTATTATGTTTTTGAGACAAT
CTCACTGTGTAGCTCAGGCTGACCTGAAACTCATGGGTGGCAATGTCTTCCCTTTATCTCCC
GAGTGTTGGGACTGTAGTGTGAAACACCTCACCTGTGGGTTTTTTTTTTTTTTAATGGACTA
TAATGCTCCAGTATGAGGAGAGGCAGCACTGGAGAATGTCTCCCAGCTGACTCACTAAGTGA
GTCACTTTAAAAAAGCAATCTGTTGGAATTCTGGCCTGCTCAACAAGAGGGAAAGCATGTTT
AGTACTGGAAACCTAGCCAACTACCCAGAACTAGTGAAGTCATGGATCTTGGAAGAGAACCT
ACAATCAACCGCCACTTCTAAACCAGCATAATCCTTAACTACATTTAAAATTTTTTTTTCAT
ACAGAATACTTTGATCTGATTATTTGCCTTCTTCCAACTCCTCCCAGGTTTTTCTTAACTCC
TGACCAATGTGTACATGAGAGCCCAAGCAAACTTCCCGAAAGCAGCAACCCTCAAAAGCAGA
AAGAAACAAAACAAAATGAGTGCACATAAAAATGGAGTCCGCACGCCTTTAATCCTAGCACT
TGGGAGGCAGAGGCAGGTGGATTTCTGAGTTCGAGGCCAGCCTGGTCTACAGAGTGAGTTCC
AGAACAGCCAGGGCTACACAGAGAAACCCTGTCTCAAAAAACCAAAAAAAACAAAAAGCAAA
AAACACCCCCCCCCAAAAAAAAAGGAGTCCATTTTGGTTTTGTGTTGGTCATTTCCTCCTG
CGCATGGGGCATGTTATACCTCCCAGTGGCACCTCATTGTAGGAAGCTGATTTTCTTTTCCC
AGCAGGTATCAATTGCAGATAGCTTCTTGGTCTAGAGTGGGACCTTCTCTGTGCTGCTTTTC
TGCCTGGTTTGAACTTGGGCAGGATTTGTGCCTGCTGTCACAGTTGCTGTGAGTTCATAAAG
ATAACTGTCCTGTTGTCTCTGGAAATGGTGTTTATGGCTTAGAGTCATCTGCCACCTCTGG
CTTGAACGATCTTTCTACCTCTTCTAAATAGCTGCATTTTGCATAGACACATTTTAAATATT
GATCTTTATGCCTCACCTTTCATCATCTAACTTCTTTTTGCAATGGAGGGGAACCATTACAG
AAAATGATAACCCACAAAATAAAGGGTTGTAGAGCCCAGTTATAACCATTACATCTACAACA
CAGCTCCTGCACCTAAGGCTCGGGGATCATTGCGTAAGAGTGAGTAGAAAAGATTGTTAAGA
GCCAGAGCATCTTTTGATGTGGGAGTGTCTCCTAGAAATGACAGAAGCTACACTCATGAGGT
CTCATCAGCATAGTTGCATGAACACGACCTGAAAAAGGACTATACCAGTAGACATGCTAATA
TGAGAGGGAAAAGCTTACAAGGTCTCTAGACAAATAGAGAAGTGTCCCTTCCCACTCCCCT
AATTGCTTATCAAATACCAAAAGGTCAGTCCTGAGAGCATACATACAAGTAACATCATTTGG
ACTGAACAGGTTGTTTTTATGTGTTTAGGAATACACACACATACACAGACATATTCAAACAA
TTAAAGAAAAAGAGGCCATGAGTTTGAAAGAGAGTGTGGTGTGAATGTACGTGAGGGGTTGG
```

FIG. 2B.8

```
AAGGAGAAAAGACAAGCTGGAAATCATATAACTAATCTTTTTTTTTTTTAAAGATTTATTT
ATTATATGTAAGTACATTGTAGCTATCTTCAGACACTCCAGAAGAGGGCATCAGATCTTGTT
ACAGATGGTTGTAAGCCACCATGTGGTTGCTGGGATTTGAACTTAGGACCTTTGGAAGAGCA
GTCAGTGCTCTTAACCACTGAGCCATCTCTCCAGCTCCATGTAACTAATCTTAAAAGGAAAA
AAAAGGAGCAACCATTTTTGTGTTTGGGCCAATCACAACCATTTCTTTGGACCAGTCACAGC
CTTGTCCCCTAGCATTAATTATAGTCTTTGGGGCTTGGATTTTAGGCCCTCTGTAAGTCTCA
CCACTTAGCATCAGTCAGAGTAGTACCTCTACTGGGGACAGCGCTAGCTCTCTGACCAAGGT
GGCAGTAGTTGCAGGGGCACCTAGAGTCCCTCAGGGCATGTGATAGCAAAAGCCTGGTACCA
GCTATTCCAGACAGCCCTGGCTGAGCTGGTTCCTTTAGGAGCGGCAGTCTTAGTGTGATTAC
CAGGGGTTTCCAGGGTAATCCAAACAGCTAGTTCTAGTGTATAGGTGCACATCTGACTCAGA
AGATAACTTTTTGTTTTGTTTTGTTTTGTCCTTTGCAGACAGAGCTGTTCTTGAACTTGCTG
TGTAGCTGAGGGTGATCTTGAAAACGATGTCCTCCTGTTACATTTCAAGTGCTGGGATTACA
GGAGAGCATTTATTAAATCCTGGCTTCTATTACATTTTAAAAAACATTTTGTATTTTTATGT
GTATGCATGTTTTGCCTGCATCTGTGTCTGCATACCACATGCCTGCTTGATGCCCAGTGATG
CCAGAAAAGGTGCCAGATCCCCTGGAACTGGAGTTATGAATAGTTGTGAGCCATCATGTGGG
TGCTAGACTGAATCTGGGTCCTCTGCAAGAGCAATAATTGCACTTAATTTCTTTCCAGTTCT
CTACCCCACCCACACCTGGCTTTTACATCTTAAGTTTGTCTATTCTATATCCATTGCATTAA
CTGTTGAGTAGACATTTGCTATAGCTTCCCAATGATCCTTTTGTCATCTTCACACATCTTCC
TTTGACCAATTATCCCTCCTGAGCTTTTGTTGCAATACTGTGGTACTTTCAAAGTAGAAATC
TGGACTGATGCAAGGCTTAGGGGGTTAGAGCACTTGCTGCCAAGAGTGATGACCTGAATTGA
TCTTTGGGATCCATGTGGTACAAGGAGAGAATTTACTATCACCAGTTGTTCTCTGATTTTCA
TGTTTACACCATGGGAATGCATGCAAACAAGTATTAAAAAAAAAAAGTGAGCCTAGCATGG
TGGGGCACACCATTTATTTTAGCACTCAGGCGGTAGAAGCAGTTGGGTCTCTTGAGTTCAAG
GTTAGCCTGGTCTACACAATGAATTCCAGGACAGCCAAGGCTATGAAGAAAAGCCCTGTCTC
AAAAAAGCAAAAACACCACTGCCTGTTTAAAATACTCTACTGATTTACTATTAATATACTTG
TAGTTTGAATGATCGTACACCTTAAAGACTCATGTAACTGAGGCTTTTTGGGGGTGCTTGT
CGTGGGGATTCTGTCCTCAGAAATGGGGTAGTACTTAAAGGTTAGAGGGAATGAGTTTAGCT
TGTTTGCCCTTTGGCCTTTTGCCATATGAGGATATAGCAAGAGACTATCACTACACAAAATA
AATGTCCACAACTTTCTTTTTGGCTCTTTTTTTTTTTCCTTTGAGATAGGGTTTTTCTGTG
TTCTTGACTGTCCTGGAACTTGCTCTATAGACCAGGCTGGCCTTGAACTCACAAAGATCTGC
CTGCCTCTGCCTCCTGAGTGCTGAGATTAAAGGCATCAGCCACCACTGCTTGACAAGTATCC
TAGATTTTAAAACTGAAATAAGGGGCTGGTGAGGTGGTAGAGCACTTGCTGCTTTTCCTTAG
GACTCAGGTTTATTCCTAGCACCCACATACTGGTTTACAGCAGTAACTCTAGTTCCAGAAGA
TTGGAACATTCTCTTCTAGCCTCTGCAGGCACCATACACATGTAGTATACAGATATACTTGC
AGTCAAAATACCCTTACACATAAATTGTAAAGTTTGTGTTTTTTAATGTGTGTGTGTGTATG
TGTGTGTATGTATGTGTGTGTGTATATATATAAAATCACAGCCTGTGATATTTTGTTGTAAC
AGCACACATTAAGATATGTTTCAGTGAGGTCTGGAAAGGTCTGTATGTATAGGTGGATTGGC
CATACTGACTTCTTAACTACCTTTCAGTGGCTGTGACAAAGCACTGTGACCAAGAAGGCACC
TTATGGAAGGAAGTGCTTATGGTGGCTTGCAGTGTCAGAGGGTGAGTTTGTATTTATCATTG
TAGGAAGCATGGTAGGCAGACACGTATGGTGCTGGAGCTGTAGGTGAGAGCCTGAACCTGAC
TTACAAGCAAGAGGCACACGCTCGAATGCTCACACGCACACACACACACACACACACACACA
CACACACACACACATACACACACACACACAAGGGGGGGGGAGAGAGAGAGAGAGAGAGG
GAGGGGCATTTGAAACCTCAAAGCCTGCTTTTAGTGATATACCTTCTCCAACAAGGTCCCAC
CTCTTAATCTTCCCCCAACAGTTTAACCGACTGTGGACCAAGTATTCAAGTACATGGGCCTA
TGGGAGTCATTCTCATTCAGACCATCACATTGGCTTTCAGTATTCCTAGTTTTCTTTTTAAA
CTCACTTTAATTCCTTAGTAGTATCCTCTAATTTGATTTGTTTCTTTTGATGGATATTACTC
ACCCATGAGGGCTTTCCTTGTCTAGATGGAAAATTGTCATATTCTTCCATACATTAATACTT
AACTTAATTGTGTATCTATTTTGCCTCCCAGAGATAATAATGACTGAGACAAAGACTATATA
TCCTTAGGAAATTTTCGTTATGGGGACAAGGGAACATGCTGAGTATGCACACACACACCTCG
CGCACACACACCCCACACCCACACGCACATAACCAAACACCAAAACTAAAACCCCTCATTTCA
AATAGATAAGGAAGTAGTAAGATGGGAGCTAGAAAACCAGGATTTGGAAGAAGGGGCTTCTT
```

FIG. 2B.9
```
CAGCTACAGGGGTTTGGAAATCAATCTTTCTTTTCTTTCTTTCTTTCTTTCTTTCTTTCTTT
CTTTCTTTCTTTCTTTCTTTCTTTCTTTCTTTCTTTCTTTCTTGGGTGGGGGCAGACTAGAC
ATGGTTTCTCTGTATAGCCCTGGCTGTCCTGGAACTCTCTGTGTAGACCAAGCTGGCCTCCA
ACTCAGAAATCCCTCTGCCTCTACCTCCCAAGCGCTGGGATCAAAGGTGTGCGCCACCACTG
CCCAGCTGAAGATAGCTTCTTTATATTATATCTAAATATTTTTATGTGTTCTGAGAGTGTGC
AGTGGCTGCAGAGGCCAGAGAGGGCACCAGATTCTGTGGAGCTAGGAGTTATAGGTGGTTGT
GAGCTGCCTAATGTGGGTGCTGGGAACAGATCCTGGGTCCTTTGGAAGAGCAGTAGTGCCCT
TAGCCACAGTCATCTCTGCAGCCTCTGTGAAAGGAGCATTCATGCAGATTTGGAGGACTTGC
TAGTTGCCTGCTTTTTTGAAGATCTAAGGAAACCATGTGGAACTGTTAGGAAATGAGAAAAA
AAAATTTTTTAATCTTATTTTATTTTTAGGGTAAAGTTCTTTATGGCAAGTATGGAGGCA
TTCTGGGGCCAGATTTATTTTAACATAACAGTATTACAATAAAATTTAGTCAACAAACATGC
GACAAAAGGAGGTGTGGGAAGCAAATGGGAACAGAGAGAGGGACAGAATCTTCAGTGAAGAT
CTGCTGAACTCTTTACAATTTCAAACCTGTTTCCCAGAGAAGTCATATGAAAATGGTGATTC
CAGGATGTTCACCTGGGACTCAGCCATGAAAGTCAGTAAAGTCACAAAAGGAGTGAACACAG
CCTAGAAATCCAGATCAGTTTAAAAGTTGTATCGGTGGATTTATCGGAGACAAGTAAATCAG
AGAAATAACCAGGAGCCAATTTGTGACTCATAGGAAGAAAGCTGGAGTTTTCTTAGGTTTGA
TGGGGTGAGTTTATTATGGGAGTATTTGATTCACTTTTCCTTTTAAGGACAGGATCTCACT
GTGTAGTCCTCCGTGACCAGAGACTCACAGAGATCTGCAAGTCTCTGCCTCCTGAGTGCTGG
GATTAAAGGTGTGCCTCGGTTGTGCTGGGCTTGACTTACTTCTTAGAGAATTAGACTGCTCA
GTGGGAAACAGACTGAAGGAGGGAGGGCAGAGTCAGCCAGTGGGGTGAGTATGACACTGAGG
AGTTAGAGCAGGTACGTGTGTTGAAGACACAGTGGGAAGTGTATGTTGGATTGCACGTGGTG
TAAGAGAACGGTGTAAGTACTCCTCCATTCCCTTTAGCATGCTAGCAGATGGCTGGGCCCTG
GGGGTAGGTTTTAGGGAGAAGAATATGATGGTGTCTGTTCAGTTATGTAAAGTATGAGATAT
CAATTAAGCATATGGTCCAGTTGGCCATGCTGGAGCTCAGGAAAAACTATATAAGATATGAA
AAATACATACTTAGTAACACTACCAAGGTCTCATTGGAAAAATTTTAAATATTGAAGAGGTT
TAAAGCTCAAGTGATAAATGTGTTTTCCCAAAATCTTTTTTTTTTTTGACTTCAGAGTTCA
AATTTTATTTATTGATGATAAGTCTTGCTGGTTATTTTCCTTAAATGACAAACTGTGTACTC
ATCAGCAGGAGACTGCCAGTACTCAAGCCTGAAAGTAGTAGTTGGTGTGTCAGTTTAAAAAA
AAAAAATGGTCTCCTTTTACAAGTAAGTTGTACTGCGGCTTTTTTCTAAAGACAACCATCAT
ATGTAGTATGTAACAAAGGCAATTTTCAGGTATTTAAGTTCTCTTGTGGGGAGAAGTTGAAA
TAGGGTCTTATCCTGTATCTCCAGCTGGCTTGGAATTTGCTGTATAGACGAGGCAGAACTCA
TAGAAATCCATCTGCCTCAGCCCCCCAAGTGCTGGATTGGAAAGCTGAAGGCCAGCTTGAGC
TACATAGGGAGAGCGAGTCTGGAAAAGTTTGACCTTGATCTTGTGAACAATCCCTCCCTAAA
GTAGACCATACTAAAGAGCCTTTGTGATTTAGTAAGCTTCATAACTTCTGCTGTAGTAATGG
GAGCCTGCATTTTACAAATCATAGTATACTTATTAATATTTTATATTTATTGAGTGTCTCTG
ACTAAAGTAAATTGGTAATCTCATAAAAATTTAGTTACTTATGCATGAATCTTCTTGGCATA
ATATCTAATATATATTATTTTAATAATTTTATATAGAGGGCTAGAGATGGTTAATAGCATA
CATAGCACTTGGTAGTGTTTTGGAGAACCTGAGTTTGGTCCCTAGCACCCACACTGAGTGGT
TCATAATCACCTATACTTTCATATAGGTTCCAATCACCTATAATCTTCAGCTCCAGGGAATC
CAACATTATTCTTTTGGCTTCTGAGGGCATCTGCATCACATGCACATTCTCACACACATACA
TATGATTAAAGAAAGTGAGGAGTTGGAGAGGTGGCTCAGTGGTTAAGAGTACTAGATGCTC
TTCCAAAACACCAGAGTTCATAGACCAGCACCCATGCCCATGACCACCAGCTGCCTGTAACC
AGCACCCATGACCATGACCACCAGAGTTCATAGACCAGCACCCATGCCCATGCCCACCAGCT
GCCTGTAACCAGCACCCATGCCCATGACCACCAGCTGCCTGTAACCAGCACCCATGCCCATG
ACCACCAGAGTTCATAGACCAGCACCCATGCCCATGACCACCAGCTGCCTGTAACCAGCACC
CATGCCCATGACTCACAACTGCCTGCAGTTCTAGTTCCAAGATCTGACACCTTCCTCTGGCC
TTGGTGGATATTCCCTCACATGTAGCAGACATTCAAATTAACACACAGAAATAAAAATAATC
TTAAAAAATCTTTGACTAGGAATTTAGATTCAGAGCCTTTCTATTATGTATATTTAATTGC
TGATGATCCTGTATTCGCTTTCTAGAGTCTGTGTCTATCAATAATTACTTACATGGTTGTTT
TTAGGCGGTTGTTCAAAACGATTTTTAGGAAAGAGTGAAAAATAGCTTTTTACTCTAAAATG
ATGATATAGTCATTTTAAATTTGAAAATGTTTCACATTGGGTTTAAAGAAATCTTATGAACA
```

FIG. 2B.10

```
CTCCTTTATTCTTGTAGAAGATCTGAATTTAAGCATCTACTTGGTGGCTCATAGAGAATCTA
ATGACCTTCTGGCCTCCACTGGCACGAGGTGTGCATATGGCACATAAACATGTAGGCAAAAG
ACTCATAAGCATAATTTAAATCCCCCCTCCCATCCCCAGAAACCTAAATCTGTTGTTGGAGG
CCAGTGAGATAAAAGTATTTGCTCTGAAGCCCAAATTCTGTCCATAGAGCCCATGTAGTAAA
GGAGACAGCCAGTACTCTCAGCCTCTGACTGCCACACATTTAACACCCACTGATAAATGTT
TAAAAGAAGCCCATTGTTCATGCCTATGGTACTTATAGAACTTCCAATTTAGAATATGTGT
GTGTGTGTGTGTGTGTGTGTGTACATGATGCCATGTGCAGGCCAGGCTGCTCCCTG
TTTACTTGACATCTTTCTTTGGGTGGTGGTTGCTGCTGTAGCCATACTTCTTGCTGCAGTTT
ACAGCATAGTGTGCAGGTCAGCACTTGCTGTAGATCATCATGTCCTAGGTTTATGTACTTCA
GGGCAAGCTGTCACAGTGAGGGCCAGTTGATAACACTGTGCATGCAGGGTAAACTCTTAATG
TTGGACACAGTGCTGTCATACTCCAGCTGTTCGACCATGAGTATGGAGTGTGATAACATTCT
TGATAATGTTACTGGGCTTGATCTCAAGAGCTATATGGTCTTGTGAGTCAAGGTCTTCTCAA
AGACTAGTATCTTGTCTGTTGGTGAGCTGCCCTGTTGAAGAAGAAAAACTGGGCTCAGTTC
TTGATCCTGTTGTCTTAACGTCTCAAATGCTAGGATTACAGGTCTGTAACACCATGTCTGAC
TCTTCATTTTCTTATATACATTTATTACTTTTGTGAAAGGCTTTGAATGAGTACATTTTTCT
GTCAAACTATGTCATTTTAAAAAGGTTTGATAAATCTGTTTTATTTTCTAACTCCAGGTTCC
ATTAAAGTTTCTAATATTTAAATTTACTAAATTGTGAGAATTTATCTTCTTATTTTGTCCTA
TGATGTTTTAATTTTTTTTTTTTTTTTTGAGTATTAATAGAGTACCAAAAATCCCAGAGGA
AACCGGCAAACTTTTATATGATCTCAAGTTAGAATCACAGAGTTTCAAAATAAATGTTTAGT
AAAATGAGATGTATCTAACAATCTGTAATGTGCTTCACCGCAGGAATATATTCGTTACTTGT
TAAGTTATCCAGCAACCTAAAAAGTGCATTCATCTTCTGTGTGAGGAGGCAGGAGGGAGAGA
GAGAGAATATGAACGTGTTGTTTGTGAGTCCTGAGCAAATATGTACCATGGTGTGCATGCCA
AGGTCTTAGGACAACTTTTGAGAGTCAGTTCTTTCCTTCTAACATGTGGGTCCTGCAGATCA
AACATAGGTCATTAGCCCCTTTACACACTGAGCCATTTTACTGACCTTTTTAGTTTTAAAGA
TTTTATTTTTATTTTTACTTTTTACTCTGATTTTATGTTGTTCAGGCTGGTCTTGAACTCCTG
ATTCATTTGCCTCCACCTTCCAAGTGCCCAATCACAGATGTGTGTTGGGCGCCAGCATGCCC
AGCTTGTTTAGTTGGTTTTTTGGAGACAAGGTCTCATTAGTTGCACAGGTTAGCCTTGAAG
GCCTAGTCTCAAGTAATCCTTTTATGGTAGGCTTATCTGTGGGTAGAATAAAAGTTGCCAGT
CACCCTGTCAGCATGTCTAGCTTAGCAACTTTCTGCCTCCTATTATTCATTCCAGTGGTTTT
GTCTATAAGATGTAATCACTCTCCTCAAATCTTTCTCATTAGTCAAATAAGTCATGAAACAT
AATAAATGGTATAGAGAAAAACACATTGACACAACAGAGTTCTTCTACTCAGCTTGATATGT
CAAAGAAGACATTATTAGGCTTGAGTTCTGAAAAATGTTAATCAGGAAAGCTGGGGTTGTGG
GGGTGCAGATAGTGGTATGTATCTAGACCAAAGTTATGTGAAAACAGAATGATTTTTAACAG
TTTATAAGCTTGGGTGCTTTAGATTACACAAAGTAGGGCAACAGTCTGTAAAGAAGTAGTAG
GAATCAGATTCAGCAAGACCTTATCAAGTCATTGTAGTGATTTTAGCTTTTTTCAAACCCTT
AGGCTGATGAAAAGGTACTGAAAGTTTTTTTTTTTTTTTTTTTTCTTCGAGACAGGGTTT
CTCTGTGTAACCCTGGCTGTCCTGGAACTCACTCTGTAGACCAGGCTGGCCTTGAACTCAGA
AATCTATCTGCCTCTGCCTCCCAAGTGCTGGGATTAAAGGAGTGTGCCACCTTTGTTCAGTA
CTGAACGTTTTAAACAATGAGATGACACTAATCCCAACTCTTGGGAAGCTGATGCTGAGGCC
GAGGCCATTCTTGACCACAAGAGACCCTATCTCAAAAAGGGGACGTGGGGGCTGGTGAACTG
GCTCAGGTGTTAAAAGTGAGTGCTGTTCTTATAAAGGACCCAAGTTTGGTTCCCAGTGCCTA
TGTCATGTGCCTCACAGATGCCTGTAACCCCAAATGCAGGGGACCCAGTACCCTCTTCTATC
GTCTGTGGGAACCTGTAGTCACATGCACATGCTAACAAGCATATACACATACTTTAAAATAA
GATAAGTTGGGCTAGAGGGTTGTTTCAGAGGTAAAGAGCATTGGCTATTCTTCAAAAGGACC
CAGGTTCAATTCCCAGTGTGCACATGGCATATCACAACTGTCTGTAACCTTAGTTCCAGGGG
ATCCAACACCATCACACACACATACAAGCAGGCAGAACTCCAATGTACAGAAAATAAAAAT
CATAAAAATAAAAATAAGTTGAAACAACAATTGCAAATTAAAAATAAGGTTATTTTTGCC
TTATGTGATGACACGAGGCTCACACCAGTAATTTCAGTACTCAGGAGCCGAGGAGGCAGTAT
TGCTACAACTTCAAGGTTAGTTGGGGCTAATACTTTTAAGCCACAGAG
```

*FIG. 2C*

SEQ ID NO: 20 - Abi1/Hssh3bp1 KO allele resulting from Cre recombinase-mediated recombination.

TCACTGCTCTTAACCACTGAGCCATCTCGCCAGCTCCCTCTTTCAATTCTTTAGGGTACAAA TTATCCTTGCTTCATTGTTTCTGCAATATCAAGCACTACTGCATGATGTACATCTGCGGTG GTACC<u>ATAACTTCGTATAGCATACATTATACGAAGTTAT</u>GGTACCTGCAGAATTCATGACAT AAGCTTGGATCCGTTCTTCGGACGCCTCGTCAACACCGTACGCAGCCTGCCCGGGGCCGCCT GTGCTCCCCACAGCCTGCCCGGGCGTTGCTCCCTAAAGCCTACCCCGGCCGAGCTCTGCTTC TCGCCGTCTGCCCGGCCCAGCTGTGCTCCCCACCACCTGCCCTG

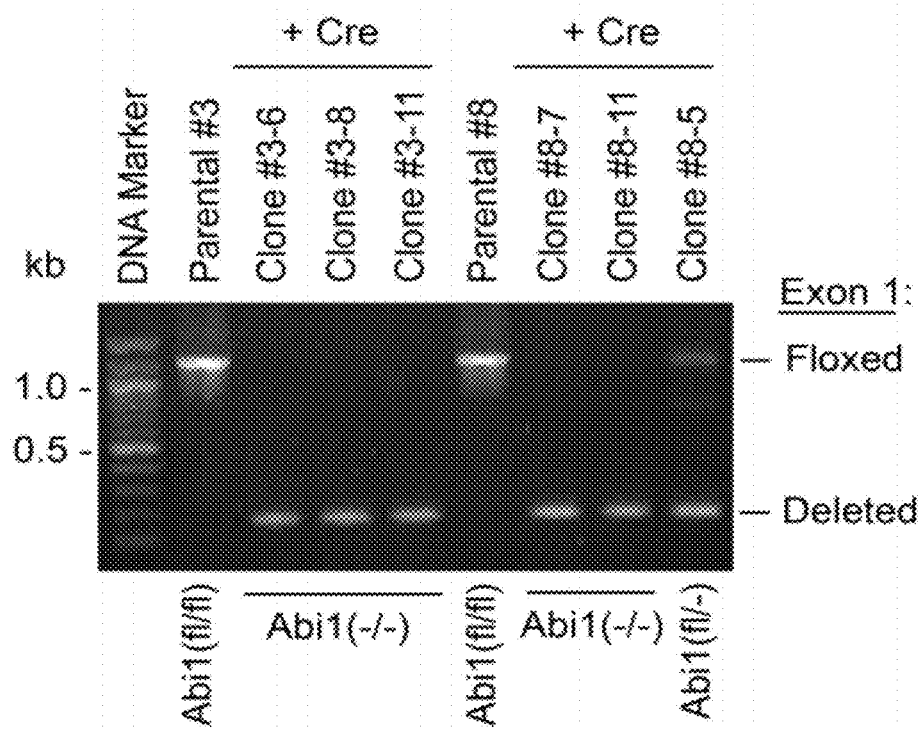

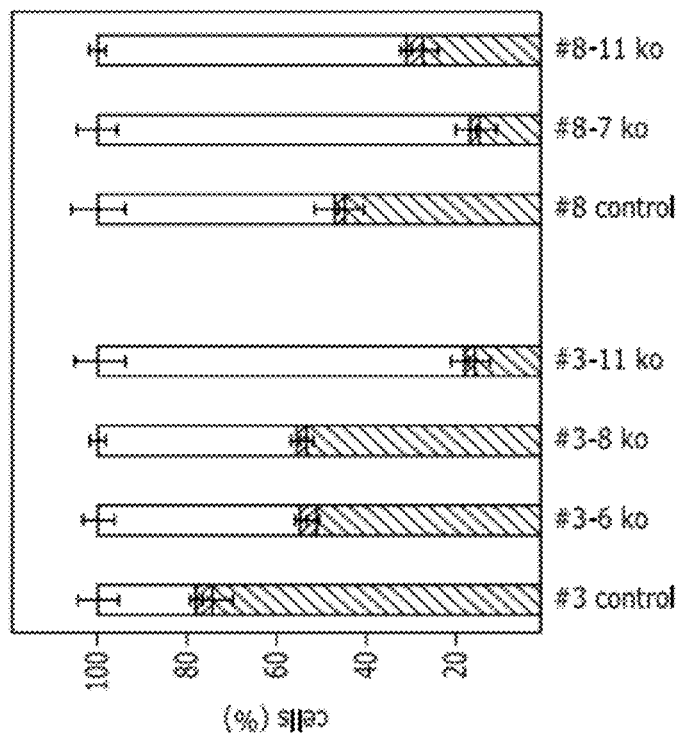
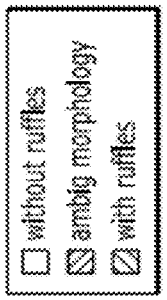
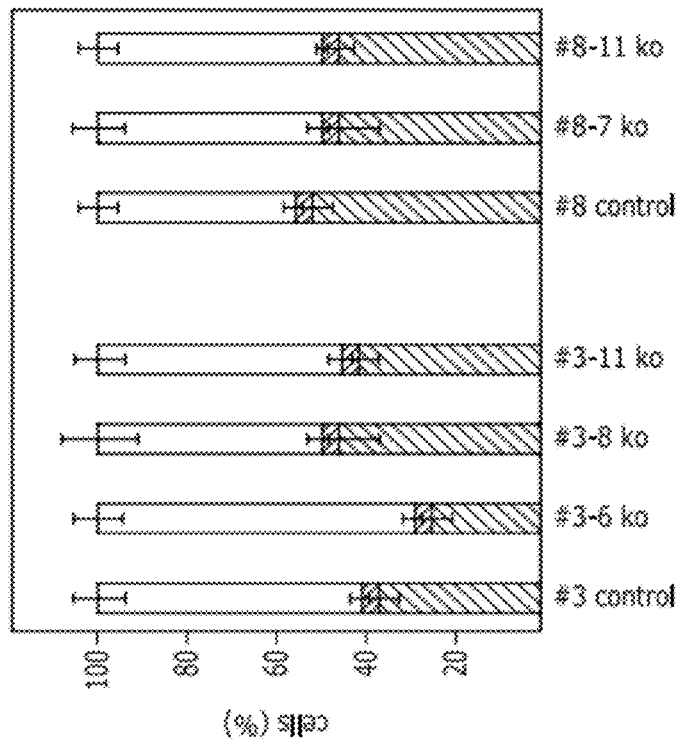
FIG. 8B
FIG. 8A

ABI1 CONDITIONAL KNOCKOUT MOUSE

CROSS-REFERENCE TO RELATED APPLICATIONS

The present application claims the benefit under 35 USC §119(e) to U.S. Provisional Patent Application 61/048,130 filed Apr. 25, 2008, the entire contents of which are incorporated by reference herein.

STATEMENT REGARDING FEDERALLY SPONSORED RESEARCH

This invention was made with Government support under Grant No. W81XWH-08-1-0320 awarded by the Department of Defense and Grant No. R01 NS044968 from the National Institutes of Health. The Government has certain rights in this invention.

FIELD OF THE INVENTION

The present disclosure relates to genetically engineered conditional knock-out mice having a conditional deletion in the Abi1/Hssh3bp1 gene and related methods.

BACKGROUND OF THE INVENTION

One of the common mechanisms in tumor formation is inactivation of one or more so-called tumor suppressor genes. Tumor suppressor genes (also known as "tumor-preventative" or "anti-tumor" genes) play an important role in the regulation of many basic cellular processes such as cell growth, division and proliferation, cell differentiation, and in communication of cells with other cells and with the extra-cellular environment. Inactivation of a tumor suppressor gene usually has devastating consequences on the regulation of cell growth within a specific tissues and usually results in tumor growth.

The selective growth advantage of tumor cells is often achieved by functional imbalance of opposing functions of tumor suppressors and oncogenes. Increased function of oncogenes such as growth factor receptors (such as epidermal growth factor receptor [EGFR] and platelet derived growth factor receptor [PDGFR]), or signaling molecule molecules (such as PI-3 kinase, Ras or Myc) promote proliferative potential of cells. When this is combined with decreased function of tumor suppressors and stabilized by inactivating mutations, cells may run out of protective responses such as apoptosis or senescence to balance the problem. Additional genomic instabilities including genetic events such as chromosomal translocations often stabilize effects of mutations subsequently leading to further amplification of anti-apoptotic, anti-senescence, and pro-proliferative signals.

The recently discovered TMPRSS2-ETS gene family chromosomal translocations and genetic alterations of tumor suppressor genes are the most common causes of neoplastic transformation leading to prostate tumorogenesis. Known prostate cancer tumor suppressor genes include Pten, p53, Rb, Nkx3.1, KLF6, and p27. However, it is clear that additional tumor suppressor genes are inactivated in primary prostate adenocarcinoma. According to the multi-hit/multi-gene hypothesis, several genes that control critical growth/survival/apoptotic pathways must be altered to lead to fully penetrant prostate cancer. For example, in mice, the loss of Pten must be accompanied by loss of p53 for progression from noninvasive to highly invasive tumors. Similar relationships have been found in other Pten double knockout models, which the second knockout gene is Nkx3.1 or p27.

A recently identified prostate cancer tumor suppressor gene is Hssh3bp1 which inhibits growth of prostate tumor cells in laboratory culture conditions. Expression of the Hssh3bp1 gene product, which is a protein, is lost in some patients with prostate tumors. Additionally Hssh3bp1 regulates the function of Abi1 kinase, which is implicated in malignant processes in leukemia. Inactivating mutations of Abi1/Hssh3bp1 have been found in primary tumors.

The successful development of novel therapies for cancer requires animal models which incorporate the unique anatomical and physiology characteristics of the target organ or tissue and appropriate stromal-tumor interactions and appropriate immunological responses. Genetically engineered mice provide these aspects. Tissue-specific developmental (through the use of developmentally regulated tissue-specific promoters driving Cre recombinase expression) or conditional (through the use of tamoxifen-responsive promoters driving Cre retroviral vectors) disruptions or overexpression of targeted genes resembles closely the mutation-driven inactivation of human tumor suppressors or activation of oncogenes, respectively, in situ. This allows evaluation of the process of tumorigenesis from early time points of gene inactivation, through early histopathological changes, and subsequently through tumor growth and metastases if such occur. The possibility of evaluation of different levels of tumor suppressor inactivation (through one- or two-allele knock-outs, or production of hypomorphic, as well as knock-in mutant strains) allows understanding of both cell signaling pathways as well as production of specific preclinical models.

SUMMARY OF THE INVENTION

The present disclosure encompasses genetically engineered mice having conditional disruption (knock-out) of the Abi1/Hssh3bp1 gene.

A transgenic knock-out mouse whose genome is heterozygous for an engineered conditional disruption in the Abi1/Hssh3bp1 gene, wherein said engineered conditional disruption in a homozygous state inhibits production of a functional Abi1/Hssh3bp1 protein.

In one embodiment, a conditional knock-out mouse is provided whose somatic and germ cells comprise a conditionally disrupted Abi1/Hssh3bp1 gene, wherein the disruption results in an inability of the mouse to produce detectable levels of the Abi1/Hssh3bp1 protein.

In another embodiment, the conditional disruption is induced by breeding the mouse with a mouse expressing flippase or Cre recombinase. In another embodiment, the conditional knock-out mouse comprises a recombinant Abi1/Hssh3bp1 allele containing a neomycin gene, frt sites and loxP sites flanking at least a portion of the Abi1/Hssh3bp1 gene.

In another embodiment, the at least a portion of the Abi1/Hssh3bp1 gene is exon 1 of the Abi1/Hssh3bp1 gene. In yet another embodiment, the conditional disruption occurs in exon 1 of the Abi1/Hssh3bp1 gene.

In another embodiment of the conditional knock-out mouse, the Abi1/Hssh3bp1 gene is not expressed in all the mouse's tissues. In yet another embodiment, the Abi1/Hssh3bp1 gene is not expressed in only a portion of the mouse's tissues, such as in the mouse's prostate tissue.

In another embodiment of the conditional knock-out mouse, the mouse exhibits at least one phenotype selected from the group consisting of disruption of cell motility, increased directional persistence, decreased migration distance, and decreased migration rate.

In one embodiment, a cell isolated from the disclosed conditional knock-out mouse is provided. In another embodiment, the cell is from the mouse's prostate tissue.

In one embodiment, a Abi1/Hssh3bp1 gene conditional knock-out construct is provided comprising a portion of an Abi1/Hssh3bp1 gene, wherein exon 1 of the Abi1/Hssh3bp1 gene is flanked by a 5' loxP site and a 3' selectable marker cassette, wherein the selectable marker cassette comprises a selectable marker flanked by frt sites and loxP sites 3' to the 3' frt site and 3' to the 5' frt site. In another embodiment, the Abi1/Hssh3bp1 gene conditional knock-out has the sequence of SEQ ID NO:14.

In one embodiment, a method is provided for producing a mouse with a targeted conditional disruption in an Abi1/Hssh3bp1 gene, comprising the steps of transfecting the disclosed knockout gene construct into a population of murine embryonic stem (ES) cells; selecting a transfected ES cell which expresses the selectable marker; introducing the transfected ES cell into an embryo of an ancestor of the mouse; allowing the embryo to develop to term to produce a chimeric mouse with a conditional knock-out construct in its germ line; breeding the chimeric mouse to produce a heterozygous mouse with a conditionally disruptable Abi1/Hssh3bp1 gene; and breeding the heterozygous mouse with a mouse expressing flippase or Cre recombinase to produce a mouse with a disruption in the Abi1/Hssh3bp1 gene and does not contain the selectable marker.

BRIEF DESCRIPTION OF THE DRAWINGS

FIG. 1 depicts construction of the Abi1/Hssh3bp1 conditional knock-out (CKO) mouse.

FIG. 2 depicts sequences of exemplary genes and alleles disclosed herein. FIG. 2A depicts the DNA sequence of the Abi1 floxed allele sequence after removal of the neomycin gene with both 5' loxP (underlined) and 3' loxP (double underlined) sites and exon 1 (bold underline, coding strand). The forward sequencing primer DL75' (bold and underline, SEQ ID NO:7) and the reverse sequencing primer Flankneo13' (bold, underline and italic, SEQ ID NO:4) are indicated. Bases in lower case represent DNA sequence of the neomycin cassette remaining after flippase-mediated neomycin gene removal. FIG. 2B depicts the DNA sequence of the ABL-1 full-length conditional allele with all recombinant elements and including the neomycin gene. The long homology arm is indicated in bold, Exon 1 is highlighted, the short homology arm is underlined, the single loxP site is indicated in double underline and the loxP/FRT sites flanking the neo cassette are indicated in bold underline. FIG. 2C depicts the DNA sequence of the Abi1/Hssh3bp1 KO allele resulting from Cre recombinase-mediated recombination. As a result of the recombination exon 1 is deleted and it contains only one loxP site (underlined). The forward sequencing primer DL75' and the reverse sequencing primer Flankneo13' are indicated (bold and underline). Only the coding strand is presented in FIG. 2C.

FIG. 5 depicts PCR-based genotyping to identify MEF cells homozygous for the recombinant Abi1 floxed allele.

FIG. 8 depicts the quantification of peripheral (FIG. 8A) and dorsal (FIG. 8B) ruffling. MEF control (fl/fl) and Abi1/Hssh3bp1 KO were plated on glass coverslips and serum-starved overnight. Cells were stimulated with PDGF, fixed and stained with Alexa Fluor 594 conjugated phalloidin to detect F-actin. The percentages of cells with different cell morphologies in response to PDGF treatment were quantified in the indicated MEF cell lines. Dorsal circular and peripheral PDGF-induced ruffles were independently evaluated. The following categories of morphologies of PDGF response were scored: with ruffles, without ruffles, or with ambiguous cell morphology. At least 100 cells were analyzed and categorized for each condition. Columns are percentage of cells with respective morphology displayed as means±SEMs of at least three independent experiments. #3 control, indicates parental MEF#3 cell line; #3-6 KO, #3-8 KO, and #3-11 KO, indicate MEF#3 subclones lacking Abi1/Hssh3bp1 expression; #8 indicates parental MEF cell line; #8-7, #8-11, indicate MEF #8 subclones.

DETAILED DESCRIPTION OF THE INVENTION

Figure 1A:
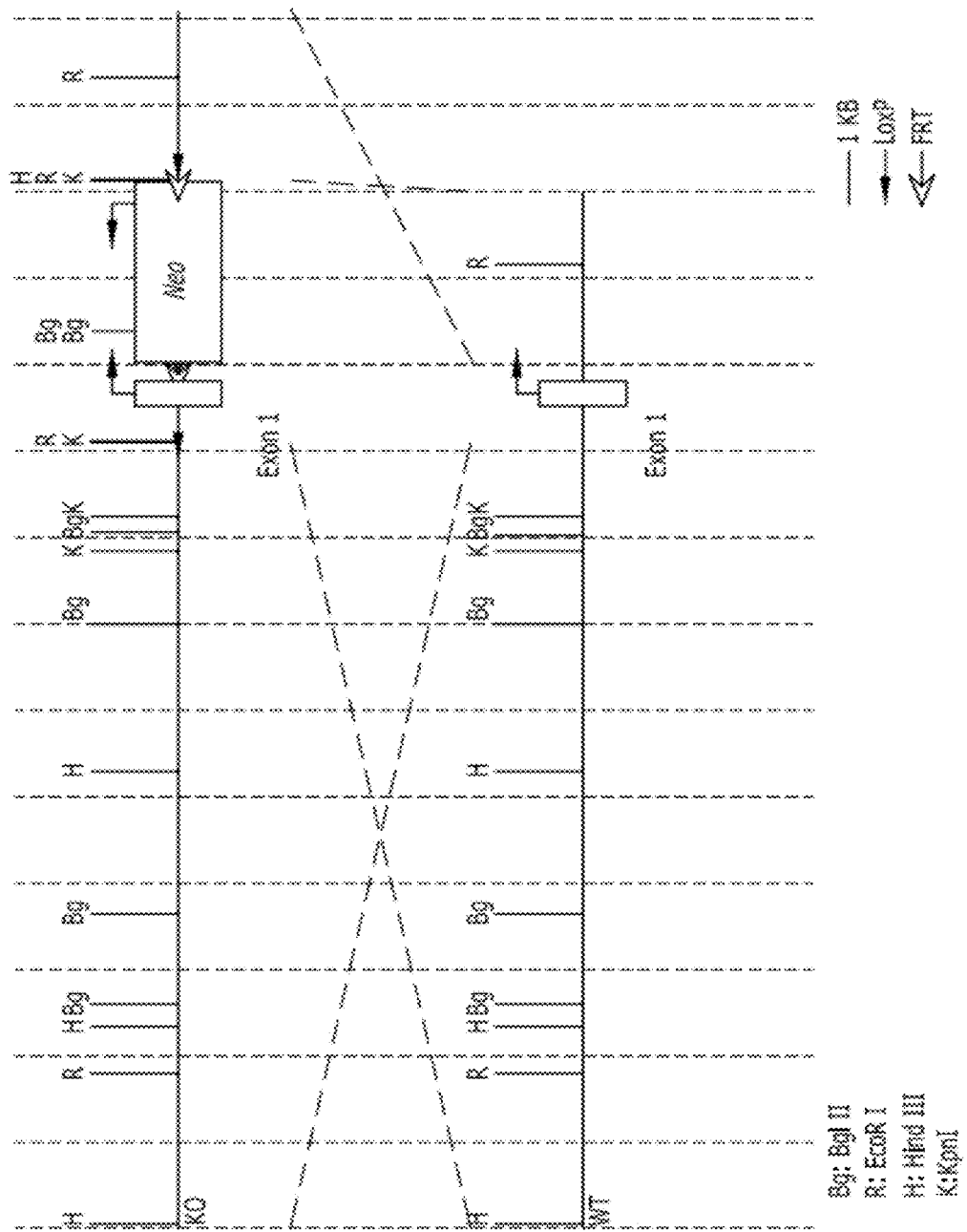
FIG. 1A depicts one embodiment of a knock-out construct.

The present disclosure encompasses genetically engineered mice having a conditional disruption of the Abi1/Hssh3bp1 gene and mice lacking expression of Abi1/Hssh3bp1 in at least one tissue. The term "Hssh3bp1" refers to a clone of the spectrin SH3-binding protein 1 (SSH3BP1) gene. The term Abi1 refers to the Abl interactor 1 (Abi-1) protein which serves as a regulator of Abl function in transformation or in signal transduction. Abi-1 and Hssh3bp1 have been determined to be the same protein. Therefore the gene is referred to herein as the Abi1/Hssh3bp1 gene.

As used herein, the term "floxed" refers to the sandwiching of a DNA sequence between two lox P sites.

As used herein, the phrase "conditional knockout," or "CKO," when used to describe a mouse, refers to mice containing the knock-out construct comprising a selectable marker inserted adjacent to exon 1 of the Abi1/Hssh3bp1 gene and wherein the selectable marker is flanked by frt sites. Additionally, there are loxP sites 5' of exon 1 and 3' of the selectable marker 3' frt site. An additional loxP site is 3' to the selectable marker 5' frt site. The conditional knockout mouse retains a functional Abi1/Hssh3bp1 gene. The term "knock-out," or "KO," as used herein refers to a mouse, or a tissue within a mouse, in which exon 1 of the Abi1/Hssh3bp1 gene has been disrupted and this mouse, or the specific tissue, does not have a functional Abi1/Hssh3bp1 gene.

c-Abl tyrosine kinase is expressed in most human tissues and has been implicated in the regulation of cell growth and death. Mutated forms of c-Abl, such as BCR-Abl, have been implicated in some forms of cancer such as, but not limited to, chronic myeloid leukemia and some forms of acute lymphocytic leukemia.

Abi1/Hssh3bp1 is a physiological inhibitor of Abl kinase. Imantinib mesylate, an inhibitor of c-Abl kinase, is an effective therapeutic agent for chronic myelogenous leukemia and other types of cancer. However, certain patients with CML are resistant to therapy with imantinib mesylate. Therefore, new therapies targeting this enzyme are needed. Abi1/Hssh3bp1-based compounds have the potential to be used for the treatment of prostate cancer. Other types of cancer are likely to involve c-Abl tyrosine kinase or Arg tyrosine kinase (Arg tyrosine kinase is the second member of the Abl family of tyrosine kinases). The Abl family of tyrosine kinases regulate the actin- and microtubule-based cytoskeleton and through the cytoskeleton, regulate basic cellular processes such as cell proliferation, division, endocytosis and differentiation. Defective fidelity of these processes often underlies tumorogenesis. Arg and Abl tyrosine kinases have highly conserved sequences, particularly in the SH3, SH2 and kinase domains. Thus Abi1/Hssh3bp1 is likely to be the source of inhibitors for multiple members of the Abl tyrosine kinase family.

Peptides, whose sequences are derived from the Abi1/Hssh3bp1 protein, inhibit c-Abl kinase activity in vitro (see U.S. provisional patent application Ser. No. 60/741,208, and subsequent non-provisional U.S. patent application Ser. No. 12/095,728 and PCT patent application PCT/US2006/45570, the disclosures of which are incorporated herein in their entirety). Some of the Abi1/Hssh3bp1 peptides contain a specific phosphotyrosine residue that is phosphorylated by c-Abl kinase. Both phosphotyrosine-containing and non-phosphorylated peptides have inhibitory activity on c-Abl kinase but mechanisms of kinase inhibition by these peptides are different. The mechanism of c-Abl kinase inhibition by phosphopeptides involves binding to the c-Abl SH2 domain, or binding to both Abl SH2 and SH3 domains, depending on the peptide length. The critical role of the Abi1/Hssh3bp1 gene in c-Abl kinase activity is supported by inhibition of cell growth upon expression of Abi1/Hssh3bp1 in cells deficient in the region containing regulatory kinase.

The conditional knockout mice, and resultant cell lines, described herein are useful for the study the role of the Abi1Hssh3bp1 gene in the formation, progression and behavior of cancer. Furthermore, the CKO and KO mice, and the resultant cell lines, are useful in screening drugs or therapeutic modalities for the treatment of cancers, in a non-limiting example, prostate cancer.

The creation of a genetically engineered CKO mouse involves inserting specific DNA sequences, such as a knock-out construct, into the mouse DNA. The inserted sequences are recognized by two DNA specific enzymes, frt recombinase (also known as flippase) and Cre recombinase, not normally present in mice. Cre recombinase recognition sites are termed loxP sites and flippase recognition sites are termed frt sites. Each of these enzymes can cut and remove a DNA sequence that is flanked by its recognitions sites. This can lead to disruption of gene function if a functional DNA sequence of the gene of interest is removed. In addition, a selectable marker gene is inserted into the mouse, the introduction of which allows selection of embryonic mouse cells (stem cells) that contain the Cre recombination or flippase recognition sites. The resultant mouse is a conditional knockout mouse.

A knock-out construct is a nucleic acid sequence, such as a DNA construct, which, when introduced into a cell, results in suppression (partial or complete) of expression of a polypeptide or protein encoded by endogenous DNA in the cell. An exemplary knock-out construct is provided herein. This construct contains a loxP site 5' to exon 1 of the Abi1/Hssh3bp1, a selectable marker cassette and a loxP site 3' to the selectable marker cassette. The selectable marker cassette comprises frt sites 5' and 3' to the selectable marker and an internal loxP site between the 5' frt site and the selectable marker gene. Suitable selectable markers include, but are not limited to, neomycin, puromycin and hygromycin. Suitable vectors include, but are not limited to, pBLUESCRIPT, pBR322, and pGEM7. Details for preparing the knock-out constructs are provided herein.

Embryonic stem (ES) cells are typically selected for their ability to integrate into and become part of the germ line of a developing embryo so as to create germ line transmission of the transgene. Thus, any ES cell line that can do so is suitable for use herein. For example, the 129SvEv ES cell line described herein may be used. Alternatively, suitable cell lines which may be used include, but are not limited to, the 129J ES cell line, the D3 ES or the JI ES cell line. The cells are cultured and prepared for DNA insertion using methods well-known to the skilled artisan Introduction of the knock-out construct into ES cells may be accomplished using a variety of methods well-known in the art, including, for example, electroporation, microinjection, and calcium phosphate treatment. For introduction of the DNA sequence, the knock-out construct DNA is added to the ES cells under appropriate conditions for the insertion method chosen. If the cells are to be electroporated, the ES cells and construct DNA are exposed to an electric pulse using an electroporation machine (electroporator) and following the manufacturer's guidelines for use. After electroporation, the cells are allowed to recover under suitable incubation conditions. The cells are then screened for the presence of the knockout construct.

Screening for cells which contain the transgene (homologous recombinants) may be done using a variety of methods. For example, as described herein, cells can be processed as needed to render DNA in them available for screening with specific probes by polymerase chain reaction (PCR).

Once appropriate ES cells are identified, they are introduced into an embryo using standard methods. They can be introduced using microinjection, for example. Embryos at the proper stage of development for integration of the ES cell to occur are obtained, such as by perfusion of the uterus of pregnant females. For example, mouse embryos at 3-4 days development can be obtained and injected with ES cells using a micropipet. After introduction of the ES cell into the embryo, the embryo is introduced into the uterus of a pseudopregnant female mouse. The stage of the pseudopregnancy is selected to enhance the chance of successful implantation. In mice, 2-3 days pseudopregnant females are appropriate.

Successful incorporation of ES cells into implanted embryos results in offspring termed chimeras. Chimeras capable of germline transmission of the mutant allele are identified by standard methods. Chimeras are bred and the resulting progeny are screened for the presence of the desired alteration (e.g., the modified recombinant Abi/Hssh3bp1 allele). This may be done, for example, on the basis of coat color or by obtaining DNA from offspring (e.g., tail DNA) to assess for the transgene, using known methods (e.g., Southern analysis, dot blot analysis, PCR analysis). Transgene expression may also be assessed (e.g., to determine if a replacement construct is expressed) by known methods, such as northern analysis or PCR analysis. Southern hybridization or PCR analysis of progeny DNA (e.g., tail DNA) may be conducted to identify desired genotypes.

The present disclosure describes a CKO wherein the disrupted gene is the Abi1/Hssh3bp1 gene. Conditional disruption of the Abi1/Hssh3bp1 gene was obtained by breeding the CKO mice with mice that express flippase or Cre recombinase. The Jackson Laboratory (Bar Harbor, Me.) sells over 70 strains of mice expressing flippase or Cre recombinase. The flippase or Cre recombinase-expressing mouse strains express these enzymes in all mouse tissues, or can express the enzymes under signals that cause them to be present only in specific tissues, such as in prostate tissue, or only in a specific cell type, such as astrocytes. In addition to tissue- or cell-specific signals, development-specific signals (such as endogenous developmental factors or diet responsive gene promoters) can be used to control the time of flippase or Cre recombinase expression. In one embodiment of the instant mouse, the action of flippase removes the neomycin gene and the action of Cre recombinase removes a critical part of the targeted gene of interest, exon 1 of Abi1/Hssh3bp1. In another embodiment of the instant mouse, the action of Cre recombinase removes both the neomycin gene and exon 1 of Abi1/Hssh3bp1. Removal of exon 1 of Abi1/Hssh3bp1 leads to inactivation of the gene due to lack of a start codon and thus no production of protein (FIG. 2C). In a knockout, preferably the target gene expression is undetectable or insignificant.

The AbiHssh3bp1 knock-out mice exhibit one or more phenotypes including, but not limited to, disruption of cell motility, increased directional persistence, decreased migration distance and decreased migration rate.

The CKO mice disclosed herein include at least three elements: (1) at least two enzyme-specific recognition sites flanking a critical portion of the target gene; (2) a gene encoding a selection marker such as, but not limited to neomycin; and (3) at least two enzyme-specific recognition sites flanking a selection marker gene for easy removal upon breeding with specific mouse strains. In a non-limiting example, exon 1 of the target gene has been designated as the critical portion. In one embodiment the enzyme-specific recognition sites flanking the critical portion of the target gene are loxP sites. In another embodiment, the enzyme-specific recognition sites flanking the selection marker gene are frt sites. In another embodiment, both sets of recognition sites comprise the same the same. In additional embodiments, other exon(s) or portion(s) of the target gene can be designated at the critical portion. In additional embodiments include DNA modifying enzymes other than flippase and Cre recombinase which mimic their action. In another embodiment, any other method of gene activation can be used to inactivate the target gene can be used. Embryonic stem (ES) cells from alternative mouse strains may also be used for gene targeting.

As used herein, nucleotide sequences which are substantially the same share at least about 90% identity, and amino acid sequences which are substantially the same typically share more than 95% amino acid identity. It is recognized, however, that proteins (and DNA or mRNA encoding such proteins) containing less than the above-described level of homology arising as splice variants or that are modified by conservative amino acid substitutions (or substitution of degenerate codons) are contemplated to be within the scope of the present disclosure. As readily recognized by those of skill in the art, various ways have been devised to align sequences for comparison, e.g., Blosum 62 scoring matrix, as described by Henikoff and Henikoff in Proc. Natl. Acad Sci. USA 89:10915 (1992). Algorithms conveniently employed for this purpose are widely available (see, for example, Needleman and Wunsch in J. Mol. Bio. 48:443 (1970).

EXAMPLES

Example 1

Genetically Engineered Abi1/Hssh3bp1 Mice

Embryos of the Abi1/Hssh3bp1 heterozygote floxed mice (Abi1/Hssh3bp1$^{loxP+/wt}$; also called Abi1/Hssh3bp1(fl/+)) were deposited at the American Type Culture Collection (Rockville, Md.) under Accession Number PTA-9966 and identified as mouse embryos 9050671 VF-1 through 9050671VF-10. These mice have the minimal amount of sequence required for conditional disruption of the gene (loxP sites around exon 1 of Abi1Hssh3bp1, hereinafter "exon 1"). These mice do not have the neomycin gene in the recombinant Abi1/Hssh3bp1 locus; there is a small amount of sequence from the neo cassette remaining (see FIG. 2A). Abi1/Hssh3bp1$^{loxP+/wt}$ are bred to obtain Abi1/Hssh3bp1$^{loxP+/loxP}$ (Abi1/Hssh3bp1 (fl/fl)) mice.

An ABI-1 conditional targeting construct (SEQ ID NO:14, also referred to as the knock-out construct or the targeting vector) was constructed having a PGK-Neo cassette flanked by frt and loxP sites inserted into exon 1 of the mouse ABI-1 gene (accession numbers NM_007380 and ENSMUSG00000058835), the mouse ortologue of the human gene ABI-1 (accession number NM_005470).

Figure 1B:
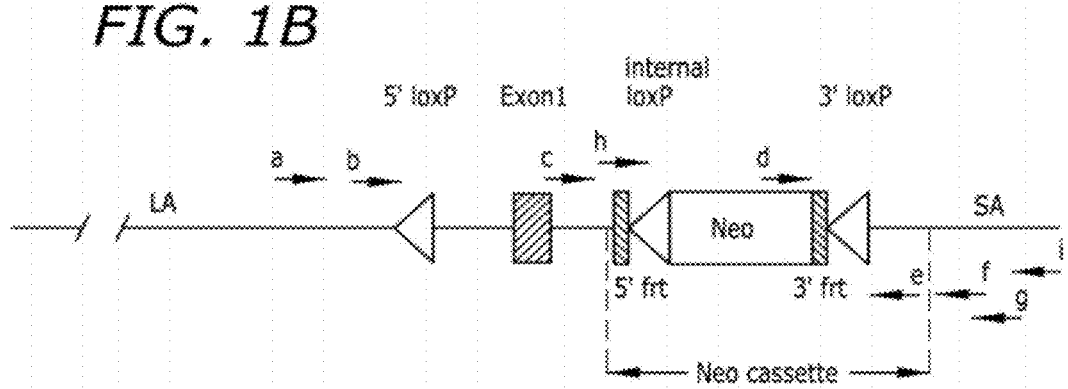
FIG. 1B depicts the cloning strategy for generation of the Abi1/Hssh3bp1 mouse. Approximately 11.8 kb region used to construct the targeting vector was first subcloned from a positively identified BAC clone. The region was designed such that the short homology arm (SA) extends 1.9 kb 3' to exon 1. The long homology arm (LA) ends on the 5' side of exon 1 and was approximately 9 kb long. The single loxP site was inserted 5' to exon 1, and the loxP-flanked neomycin gene cassette was inserted 3' to exon 1. The neomycin gene cassette was bound by two frt sites, with one loxP site 3' to the 5' frt site. The target region was 0.9 kb and included exon 1. Locations of primers used for confirmation of the locations of loxP sites and for subsequent genotyping are indicated: a, mAbi1loxP35' (SEQ ID NO:3); b, DL75' (SEQ ID NO:7); c, mAbi1Intr15' (SEQ ID NO:15); d, LAN1 (SEQ ID NO:1); e, Neogene13' (SEQ ID NO:16); f, Flankneo13' (SEQ ID NO:4); g, A2 (SEQ ID NO:2); h, WT1 (SEQ ID NO:17); and i, SG1 (SEQ ID NO:18). The "h" and "i" primer set (arrows) are specific for the wild type Abi1/Hssh3bp1 gene sequence only.

A genomic bacterial artificial chromosome (BAC) clone was isolated and the conditional KO construct was generated. An approximately 11.8 kb region used to construct the targeting vector was first subcloned from a positively identified BAC clone using a homologous recombination-based technique. The region was designed such that the short homology arm (SA) extends 1.9 kb 3' to exon 1. The long homology arm (LA) ends on the 5' side of exon 1 and is approximately 9 kb long. The single loxP site is inserted 5' to exon 1, and the loxP-flanked Neo cassette is inserted 3' to exon 1. The target region is 0.9 kb and includes exon 1 (FIG. 1, FIG. 2). The targeting vector was confirmed by restriction analysis after each modification step and by sequencing using specific primers.

The conditional KO construct was transfected into 129SvEv embryonic stem (ES) cells, and approximately 300 antibiotic-resistant colonies were selected. After in vitro expansion, aliquots of cells were lysed, DNA was extracted, purified, and dried into 96-well tissue culture plates. The 96-well plates of DNA isolated from the homologous recombinant clones were screened using a PCR-based strategy utilizing PCR primers located in both the short homology arm and within the Neo cassette. Positive clones were then submitted for sequencing to confirm proper integration of all loxP and frt sites, and then finally expanded into cultured ES cells.

Two positive ES clones, 1-2D3 and 1-3D1, were microinjected into C57BL/6 blastocytes which were implanted into the uteri of pseudo-pregnant females. Pseudo-pregnant female mice then gave birth to the offspring. Upon reaching 4 weeks of age, chimerism in the offspring was analyzed by coat color observation. Five males of at least 90% agouti chimerism were obtained. Male mice having at least 90% agouti chimerism upon reaching 6 weeks of age were haremmated with C57BL/6 wild-type female mice for the production of heterozygous offspring. Both F1 heterozygous male and female offspring were obtained.

Heterozygote mice with the initial recombinant DNA elements (i.e. neomycin gene, loxP, and frt sites (i.e. neo+/loxP+/frt+)) were found to be less fertile; breeding of these mice led to fewer pups, in the range of 2-4 (6-12 pups is normal). Homozygote mice with the neomycin gene in the recombinant gene cassette were not obtained. Homozygote floxed mice were obtained upon removal of the neomycin gene.

Following successful breeding of Abi1/Hssh3bp1 chimeric mice, the germline transmission of the modified recombinant Abi1/Hssh3bp1 allele (containing the neomycin gene, frt and loxP sequences) was achieved and subsequently led to production of F1 strain. The resultant offspring were genotyped by PCR to determine the presence of the conditional knockout (CKO) allele and were also sequenced for the presence of loxP and frt sites.

Figure 3:
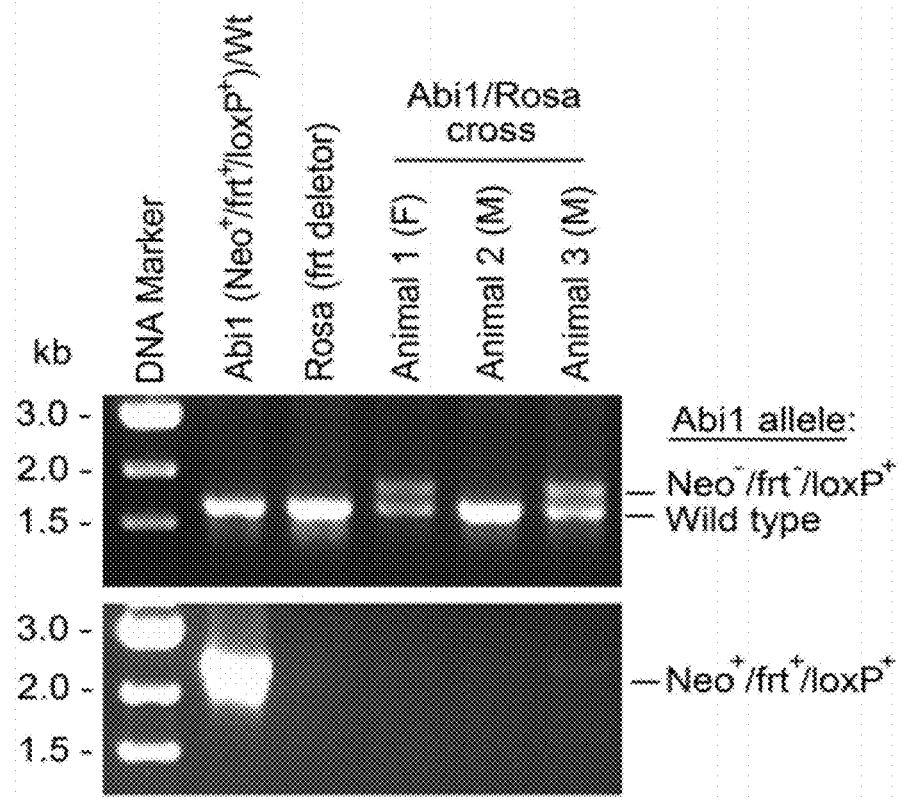
FIG. 3 depicts genotyping of the F1 Abi1/Hssh3bp1 heterozygous strain by polymerase chain reaction (PCR) with primers LAN1 (5'-CCAGAGGCCACTTGTGTAGC-3'; SEQ ID NO:1) and A2 (5'-CTGGAAGCTGACAAGAGGATAG-3'; SEQ ID NO:2) for the neomycin gene cassette (Neo$^+$/frt$^+$/loxP$^+$), with primers mAbi1loxP35' (5'-AATAATTTAAT-AGTTCTGGTGATAT GACAGC-3'; SEQ ID NO:3) and Flankneo13' (5'-GGGCAGACGGCGAGAAGCAGAG-3'; SEQ ID NO:4) for the wild type allele (Wt) (upper panel, lower band) or the floxed Abi1/Hssh3bp1 allele, which is lacking the neomycin gene and the 3' frt site (Neo$^-$/frt$^-$/loxP$^+$) (upper panel, upper band).

Mice heterozygous for the recombinant Abi1/Hssh3bp1 allele containing neomycin gene, frt sites and loxP sites were bred with the "frt deletor" strain 129S4/SvJaeSorGt(ROSA)26Sortm1(FLP1)Dym/J (Jackson Laboratories, Inc. stock number 003946). Flipase-mediated deletion of the neomycin gene from the recombinant gene cassette was confirmed by genotyping with specific primers. Heterozygous Abi1/Hssh3bp1 animals (Abi1/Hssh3bp1 (loxP+/wt) also called Abi1/Hssh3bp1 (fl/+) or (floxed/+)) (see FIG. 3) were subsequently bred to obtain homozygous Abi1/Hssh3bp1 (fl/fl) mice. Mouse embryonic fibroblast (MEF) cell lines were subsequently obtained from these mice.

Example 2

Cell Lines with Normal and Mutant Hssh3bp1 Genes

Figures 5A, 5B:
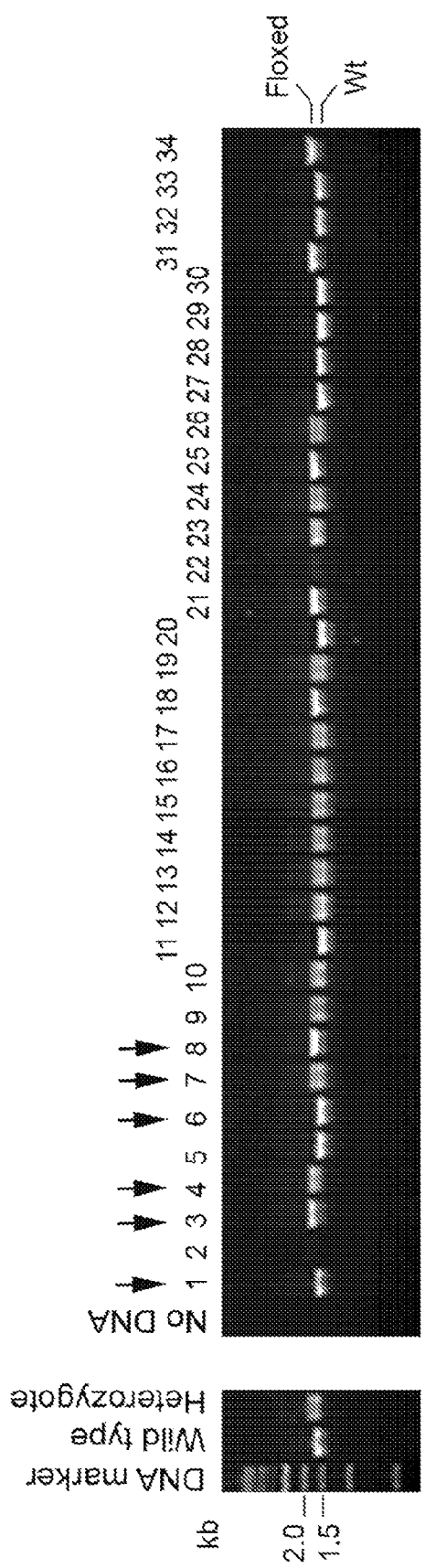
FIG. 5A depicts the genotyping controls for MEF cell screening. Genomic DNA obtained from the frt deletor strain and expressing only wild type alleles (lower band), and heterozygous Abi1/Hssh3bp1 (fl/+) animals expressing wild type (lower band) and Abi1/Hssh3bp1 floxed alleles (upper band), were subjected to PCR genotyping.
FIG. 5B depicts screening of MEF cells. MEF cell DNA samples (#1-34) were isolated from mouse embryos that resulted from breeding of heterozygous Abi1/Hssh3bp1 (fl/+) animals. Upper band, floxed Abi1/Hssh3bp1 allele (Floxed); Lower band, wild type allele (Wt). Genotyping was performed using primers mAbi1loxP35' and Flankneo13'.

A cell line was isolated from the heterozygote mouse described in Example 1. The cell lines, termed MEF for mouse embryonic fibroblast, have one copy of the wild-type gene and one copy of the genetically recombined Abi1/Hssh3bp1 gene with loxP sequences flanking exon 1 (this cell line contained the neomycin gene). Following isolation of primary MEF, the cells were genotyped by PCR (FIG. 5). Several MEF cell lines were randomly selected. These included cell lines expressing wild type Abi1/Hssh3bp1 as well as lines expressing the desired homozygous floxed Abi1/Hssh3bp1 gene (FIG. 5).

MEF cell lines were immortalized by retroviral transduction of the SV40 large T antigen. Following genotype confirmation, homozygous Abi1/Hssh3bp1 (fl/fl) MEF cell lines (parental MEF #3 and parental MEF #8) were used to obtain syngeneic cell lines in vitro (i.e. for in vitro genetic knockout experiments). The Abi1/Hssh3bp1 (fl/fl) cell lines were either transiently transfected with a Cre recombinase-encoding plasmid in order to remove the floxed alleles, or with a control EGFP (enhanced green fluorescent protein) plasmid expressing puromycin. Both plasmids carried the puromycin resistance cassette. For transfection FuGene6 reagent was used according to the manual (Roche). Transfection medium was replaced after 24 hours by normal medium supplemented with 5 µg/ml puromycin. Cells were cultured with puromycin for six days (the appropriate puromycin concentration was achieved by performing a killing curve). Cell lines were then cultured under normal conditions as described above. Single clones were obtained by limiting dilution subcloning. For each Abi1/Hssh3bp1 precursor cell line at least 10 individual Abi1 KO cell clones were established. The effective removal of the Abi1 floxed alleles in cells transfected with the Cre recombinase encoding plasmid was confirmed by PCR, by evaluation of protein expression levels, and by RNA-array analysis.

Figure 6:
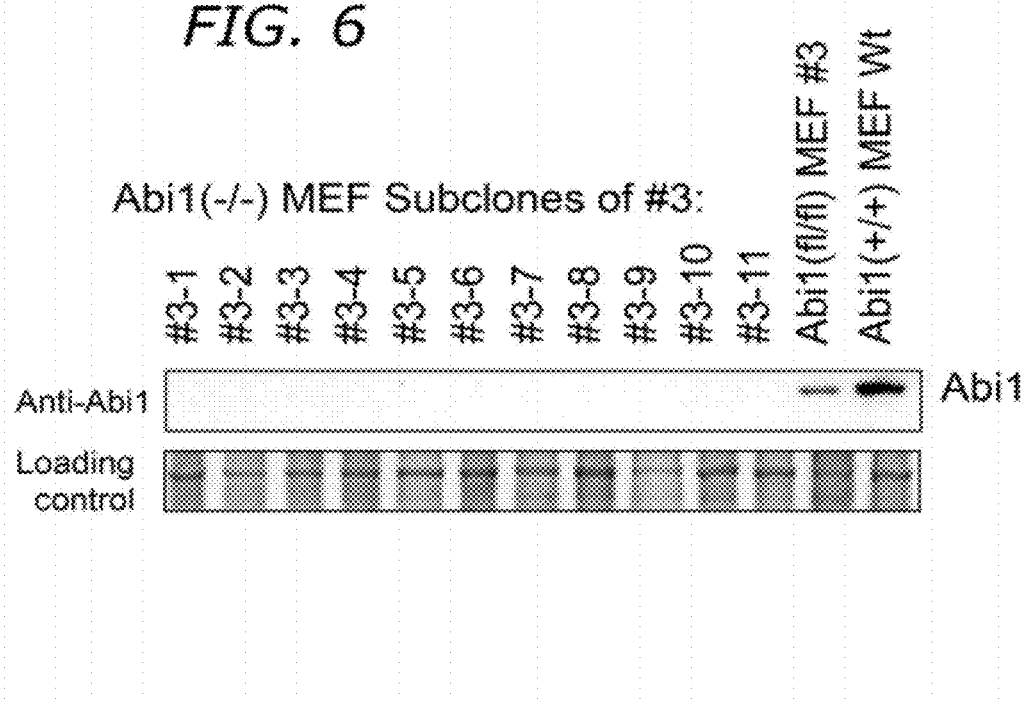
FIG. 6 depicts Cre recombinase-mediated loss of Abi1/Hssh3bp1 protein expression in MEF#3 cell line subclones. Western blot analysis of Abi1/Hssh3bp1 expression in parental MEF#3 Abi1(fl/fl) and in exon 1 deleted Abi1(−/−) MEF cell lines is depicted in the lower panel. Cell lysates of the indicated cell lines were blotted with antibody 7B6 (specific for Abi1/Hssh3bp1). Clones #3-1 through #3-11 represent subclones of the parental MEF#3 obtained following transient Cre recombinase expression. Abi1 (+/+) MEF Wt represents mouse embryonic cells expressing the wild type Abi1/Hssh3bp1 gene. Loading control represents part of a protein-stained gel of the same samples as used for Western blotting analysis in the upper panel.
Figure 4A:
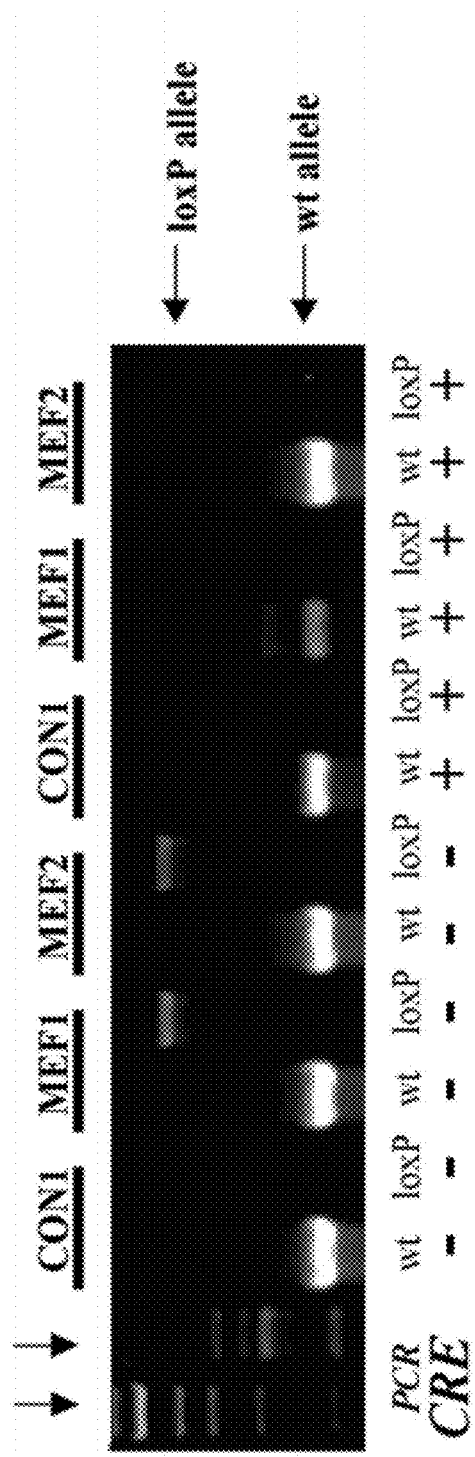
FIG. 4 depicts the Abi1/Hssh3bp1 gene disruptions in primary mouse embryonic fibroblasts isolated from Abi1/Hssh3bp1$^{loxP/+}$ (FIG. 4A) and Abi1/Hssh3bp1$^{loxP/loxP}$ (Abi1/Hssh3bp1[fl/fl]
FIG. 4B) mice.

Clones #3 and clone #8 were used for production of Abi1/Hssh3bp1 deletion lines. Disruption of the Abi1/Hssh3bp1 gene by deletion of exon 1 was achieved by transient transfection with Cre recombinase using a plasmid conferring resistance to puromycin. Genomic deletion of Abi1/Hssh3bp1 exon 1 was confirmed by genotyping with several PCR primer sets, including primers DL75' (SEQ ID NO:7), Neogene 13' (SEQ ID NO:16), and mAbi1loxP35' (SEQ ID NO:3) (FIG. 4), and by sequencing PCR products. Western blot analysis (FIG. 6) demonstrated the lack of Abi1/Hssh3bp1 protein expression in the clones. Representative data from 11 subclones of the parental MEF clone #3 are presented in (FIG. 6).

Example 3

Morphology of Cells Lacking Abi1/Hssh3bp1 Gene Expression

Abi1/Hssh3bp1 is localized to PDGF (platelet derived growth factor)-stimulated peripheral and dorsal ruffles in precursor (fl/fl) cells, but is absent from knockout MEF cells. Abi1/Hssh3bp1 is known to be involved in actin reorganization resulting in lamellipodia, and in actin-rich peripheral and dorsal ruffle formation. Therefore, it was determined whether Abi1/Hssh3bp1 localizes to these structures in isolated MEF cells and whether any defect in these structures is observed in cells lacking expression of a functional Abi1/Hssh3bp1 gene.

Figure 7:
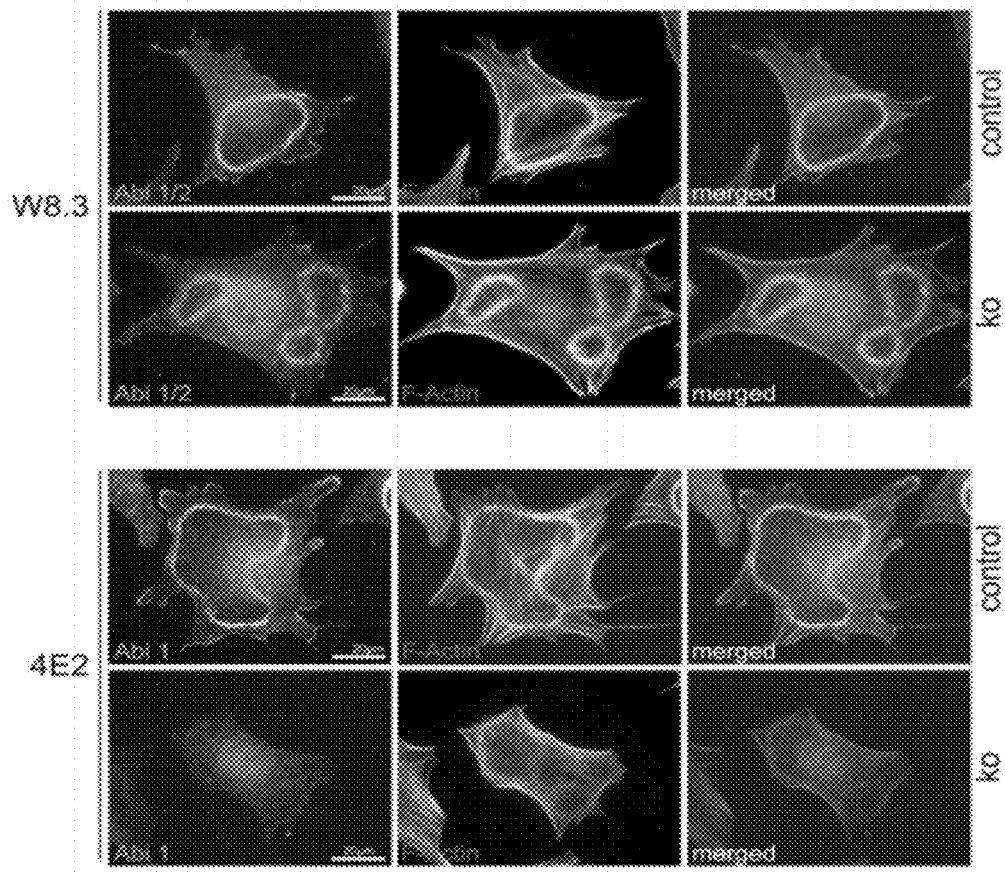
FIG. 7 depicts the localization of Abi1/Hssh3bp1 in control and deficient MEF cells after platelet derived growth factor (PDGF)-stimulation. Control (#3) and Abi1/Hssh3bp1-KO (#3-11) cell lines were grown on glass-coverslips, starved and treated with PDGF, and immunostained with antibodies and phalloidin. Anti-Abi1/2 antibody (W8.3) or anti Abi1 (4E2) antibody were used.

Upon PDGF treatment, both Abi1/Hssh3bp1 (fl/fl) control (#3) and Abi1/Hssh3bp1 deficient (clones #3-11) cells display peripheral as well as dorsal ruffle formation, although dorsal ruffling is less prominent in the Abi1/Hssh3bp1 KO cell line. Abi1 is highly enriched in dorsal ruffles and localizes at the tip of ruffles in the cell periphery in Abi1/Hssh3bp1 control cells, while it cannot be detected in the Abi1/Hssh3bp1 knockout cell line. Abi2 is also present in both cell lines, but in the Abi1/Hssh3bp1 control cells, it cannot be distinguished from Abi1/Hssh3bp1 localization (FIG. 7). Thus, we have confirmed the participation of Abi1/Hssh3bp1 in the formation of circular and peripheral ruffles in control (fl/fl) MEF cells and the absence of Abi1/Hssh3bp1 in knockout MEF cells.

PDGF stimulation of Abi1/Hssh3bp1 MEF cell lines led to the formation of both peripheral and dorsal ruffling in Abi1/Hssh3bp1 control and Abi1/Hssh3bp1-deficient cells. Multiple cell morphologies were observed, and were quantified and classified according to the following categories: with ruffles, without ruffles, or with ambiguous cell morphology (FIG. 8). Remarkably, lack of Abi1/Hssh3bp1 did not affect peripheral ruffle formation in a quantifiable manner, whereas dorsal ruffling was significantly reduced in all tested Abi1/Hssh3bp1 KO cell lines as compared to their respective parental controls. Abi1/Hssh3bp1 KO clone #3-11 showed the most severe phenotype in response to PDGF treatment. Notably, the Abi1/Hssh3bp1 #3 control cell line was stimulated to a greater extend by PDGF as compared to the Abi1/Hssh3bp1 #8 control cell line (FIG. 8).

Figure 9:
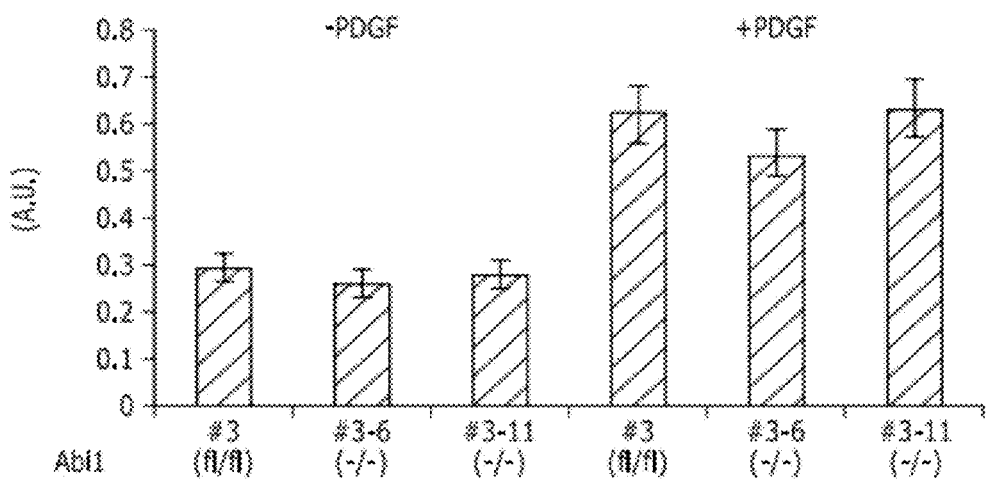
FIG. 9 depicts PDGF-induced Rac activation. The indicated parental Abi1/Hssh3bp1 (fl/fl) and Abi1/Hssh3bp1 KO (−/−) cell lines were analyzed in the assay.

No change in Rac activity was observed in cells lacking a functional Abi1/Hssh3bp1 gene. Rac activity was assayed in Abi1/Hssh3bp1 MEF cell lines following PDGF treatment using the G-LISA kit (Cytoskeleton, Inc.) according to manufacturer's instructions. The PDGF treatment induced strong Rac activation in both Abi1/Hssh3bp1 control and Abi1/Hssh3bp1-deficient cell lines (FIG. 9). However, no significant effects were observed in the Abi1/Hssh3bp1 knockout cells. This observation suggested that Abi1/Hssh3bp1 acts either downstream of Rac or that Abi1/Hssh3bp1 function is compensated for by another protein, for instance Abi2.

Figure 10A:
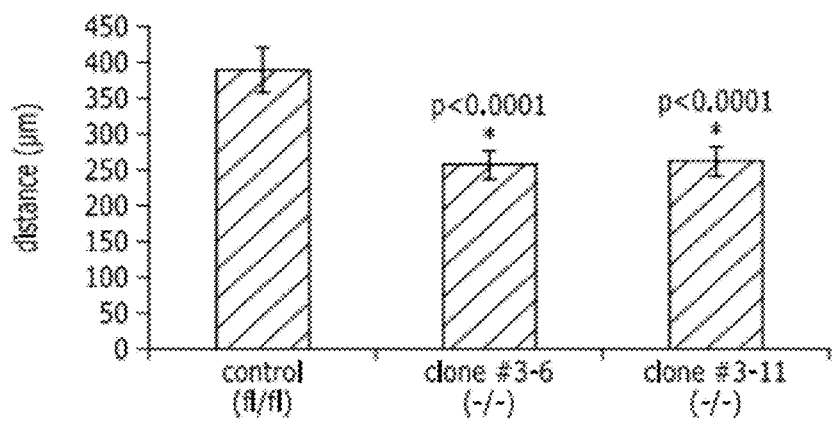
FIG. 10 depicts the evaluation of cell motility of mouse embryonic fibroblasts lacking Abi1/Hssh3bp1. The parameters of random cell motility, migration distance (FIG. 10A), rate (FIG. 10B), and directional persistence (FIG. 10C) were evaluated in Abi1/Hsshb3p1 null cell lines (clones #3-6 and #3-11) and Abi1 floxed cells (control #3, (fl/fl)) cells.
Figure 10B:
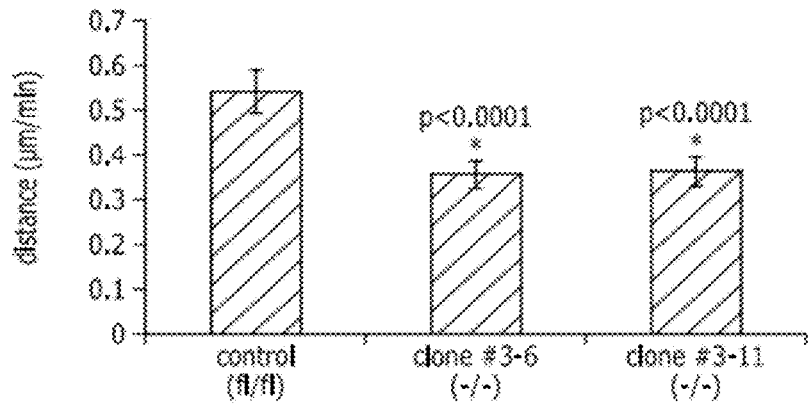
Figure 10C:
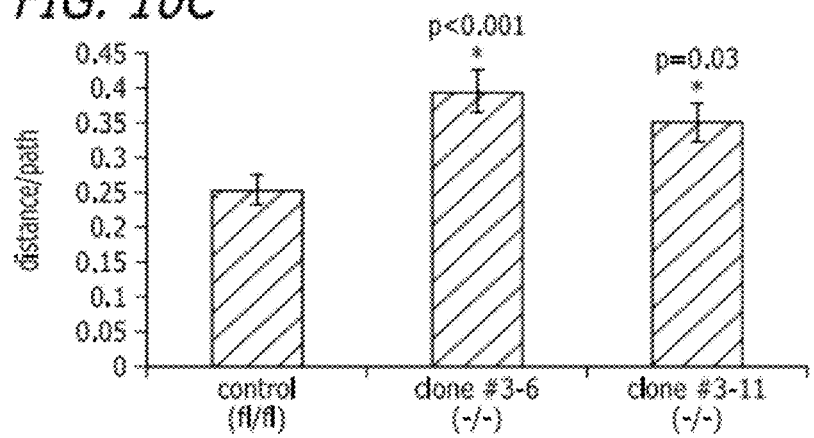

Cells lacking Abi1/Hssh3bp1 exhibit cell motility defects. Abi1/Hssh3bp1 has been implicated as a regulator of actin cytoskeleton-dependent cell motility as part of the Wave 2 complex. Therefore, Abi1/Hssh3bp1 KO MEF cell lines were examined in a series of motility assays. For random migration analysis, cells were seeded in 6-well plates at a density of $10^4$ cells/well in regular growth medium, and placed in a temperature- and $CO_2$-controlled microscope chamber (Axiovert 200, Carl Zeiss, Microimaging Inc.). Time lapse recording started 6 hours after plating. Images were collected with a 10× objective at 15-minutes intervals over an 8 hour period, using an AxioCam MRm camera (Zeiss) and Axiovision software. Motility parameters including migration path, distance, rate and directional persistence were obtained from time-lapse movies. To track the migration path of individual cells, cells were manually located in each frame using ImageJ software (NIH ImageJ, software Version 1.41n); nuclei were used as geographical centers for tracking. The migration paths were expressed as graphs. The rates of cell migration were calculated as a ratio of the total length of migration paths and the duration of migration. Migration distances were determined as the net translocation during an 8-hour period. Directional persistence was calculated as a ratio of the direct distance during an 8-hour period and the total length of the migration path. These assays indicated reduced random cell motility (migration rate and migration distance), but increased directional persistence of cells lacking Abi1/Hssh3bp1 (FIG. 10).

Figure 11A:
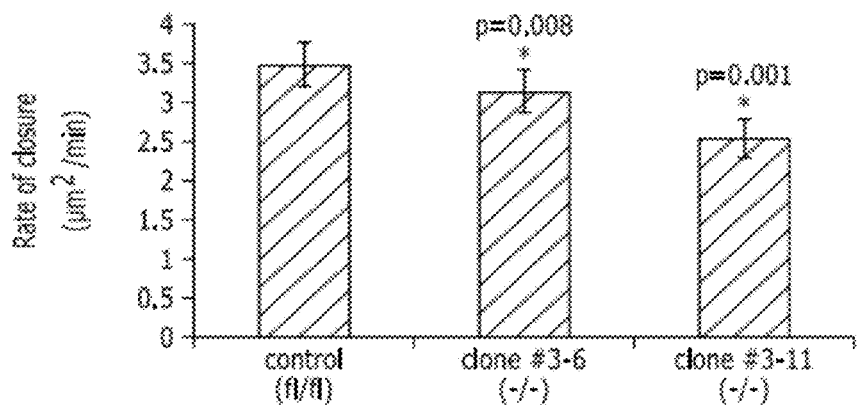
FIG. 11 depicts data from the wound-healing migration assay. The rate of wound closure was determined by measuring the area not covered by cells per unit of time. Data represent means±SD of four independent assays of Abi1/Hssh3bp1 KO cell lines (#3-6 and #3-11) as compared with control #3 (fl/fl) MEF cells (FIG. 11A).
FIG. 11B depicts representative micrographs from live cell observations.
Figure 11B:
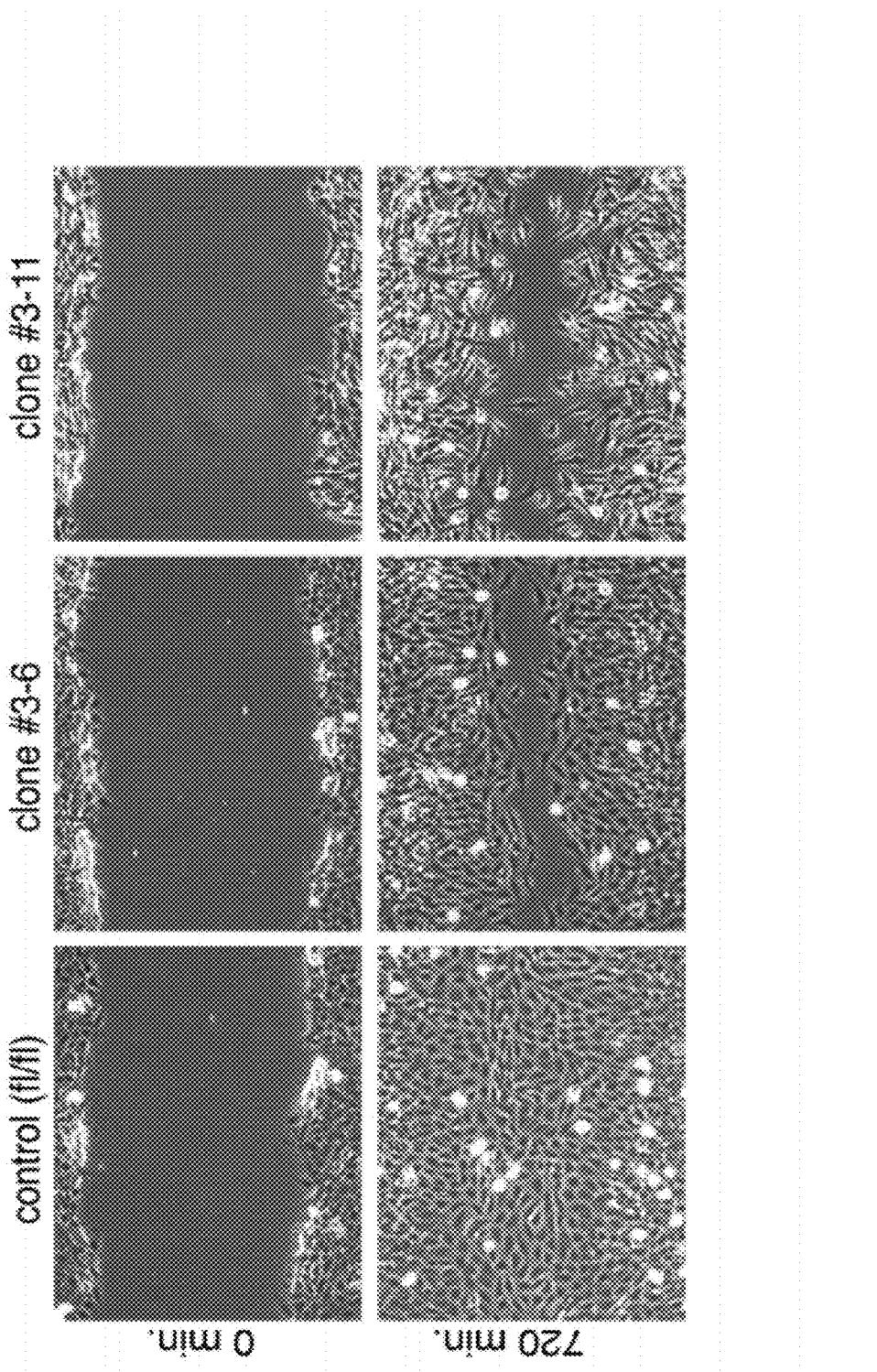

To determine the effects of Abi1Hssh3bp1 on wound healing, cells were seeded in 6-well plates at a density of $1 \times 10^6$ cells/well in regular growth medium. After 6 hours, the confluent monolayer of cells was scratched with a fine pipette tip, and migration was visualized by time-lapse imaging as described above. The rate of wound closure was determined by measuring the area not covered by cells per unit of time. Each assay was repeated at least four times. In this assay, subtle but statistically significant impairment of wound closure of cells lacking Abi1/Hssh3bp1 (FIG. 11).

Figure 12:
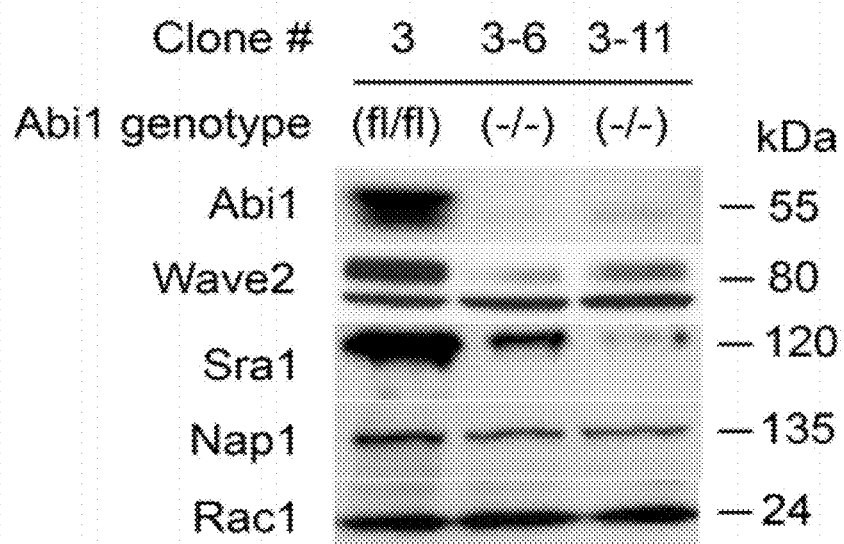
FIG. 12 depicts the evaluation of Wave complex in Abi1/Hssh3bp1 KO cells. Western blot analysis of MEF cell lysates of Abi1/Hssh3bp1 KO cell lines. WAVE 2, Nap1, and Sra-1 protein levels were evaluated with specific antibodies in total cellular lysates obtained from 2 clones (#3-6 and #3-11) lacking Abi1/Hssh3bp1 expression and from the parental line MEF#3.

Cell motility assays indicated defects in cell motility in Abi1/Hssh3bp1 KO cells and suggested downregulation of Wave 2 dependent actin polymerization. It is assumed that Abi1/Hssh3bp1 is a vital part of the Wave 2-Arp 2/3 activating complex, which is regulated by Rac1 activation. Interaction between Rac1, Wave complex and Abi1 is mediated by Nap1 and Sra-1. Data from RNA silencing experiments indicated that upon downregulation of individual subunits, all major components of the Wave 2 complex are coordinately down regulated. How gene disruption-mediated (i.e. genetic) knockout of Abi1/Hssh3bp1 affects the stability of the WAVE2 complex components was studied. Western blot analysis demonstrated that Wave 2, Sra-1 and Nap1 expression levels were lower in Abi1 (−/−) null cells but were not completely abrogated (FIG. 12).

Example 4

Sequencing of Abi1/Hssh3bp1 Knock-Out Mouse Genome

Figure 14:
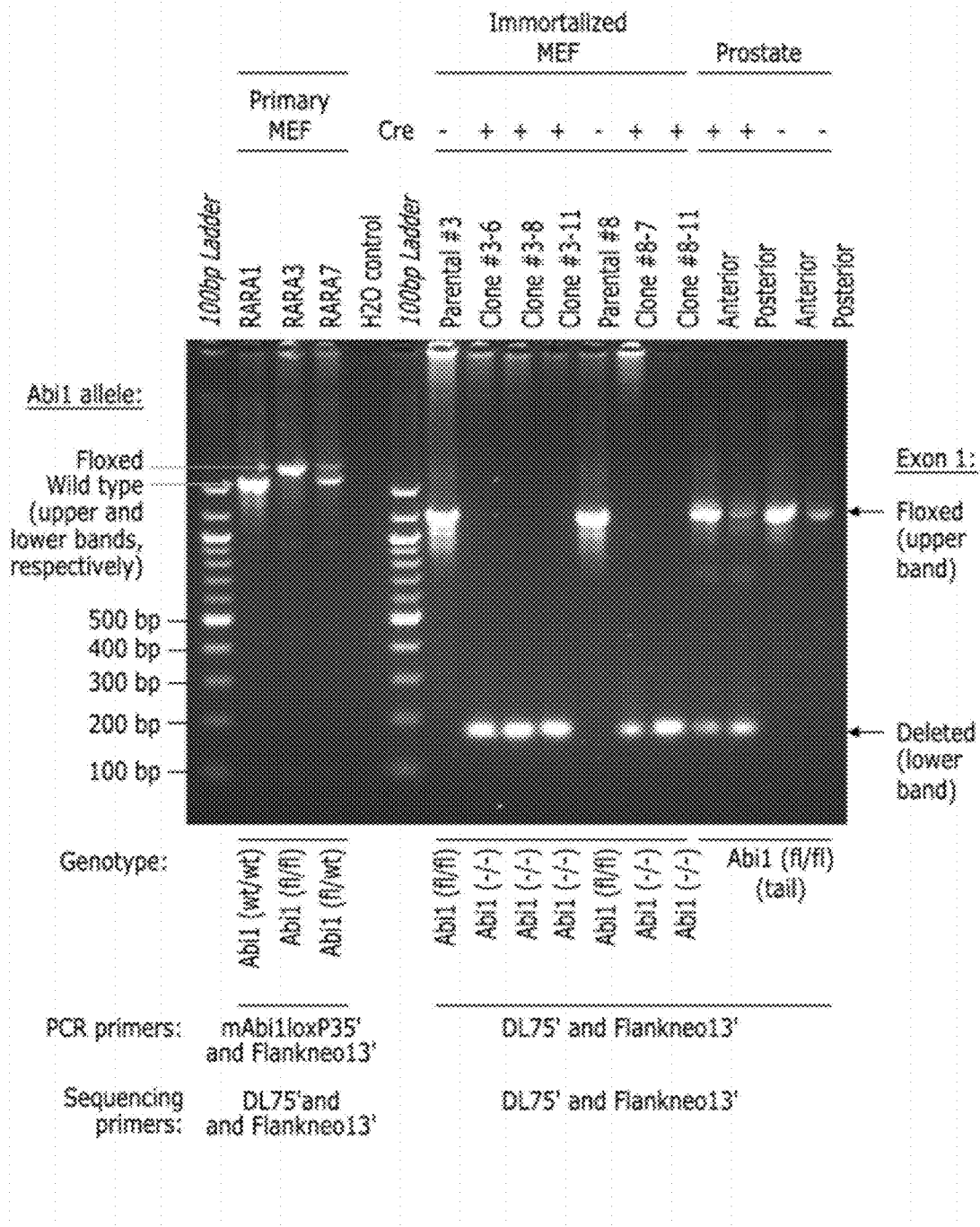
FIG. 14 depicts the prostate-specific disruption of the Abi1/Hssh3bp1 gene. Animals (males only) resulting from breeding of the probasin promoter driven Cre recombinase expressing strain [B6.D2-Tg(Pbsn-Cre)4Prb] with the Abi1/Hssh3bp1 floxed (fl/fl) strain were genotyped for expression of the floxed Abi1/Hssh3bp1 allele and Cre recombinase expression. Prostate tissue (anterior prostate and posterior prostate) from animals expressing Cre recombinase demonstrated exon 1 deletion (Deleted) in contrast to animals negative for expression of Cre (Floxed). Primary MEF (RARA1, RARA3 and RARA 7), parental MEF #8 (Abi1 (fl/fl)) and its subcloned cell lines #8-7 and #8-11 and parental MEF#3 and its subcloned lines #3-6, #3-8 and #3-11 were also genotyped.
Figure 15:
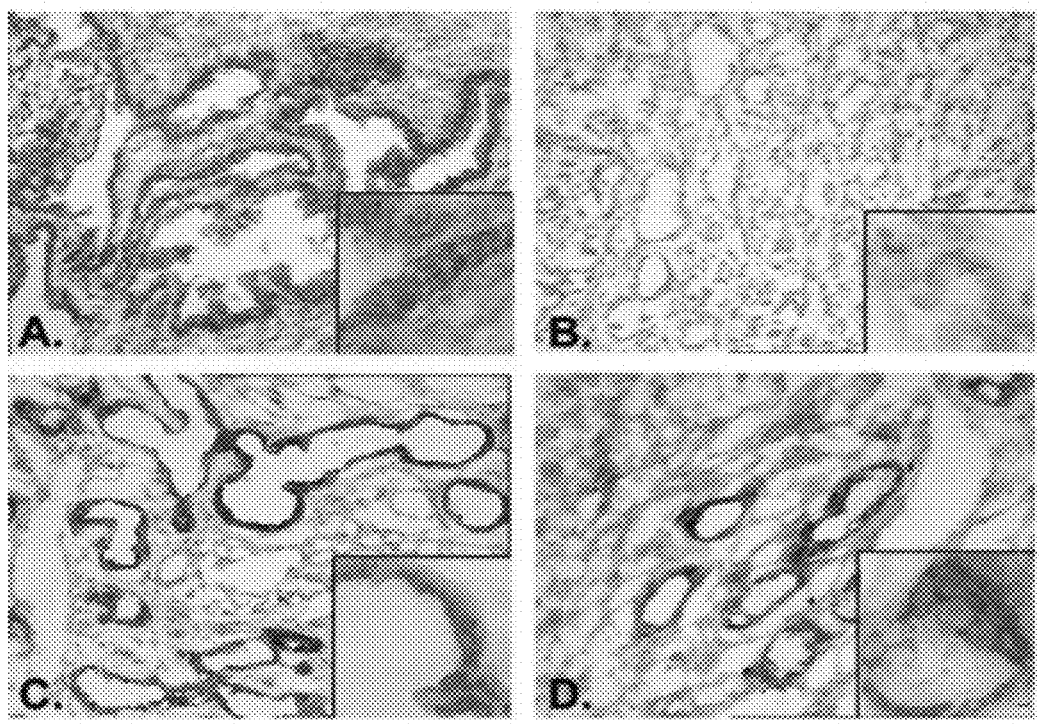
FIG. 15 depicts staining of normal (FIGS. 15A and 15C) and malignant (FIGS. 15B and 15D) prostate tissues from cases 398 (FIGS. 15A and 15B) and 400 (FIGS. 15C and 15D) with mAb 2G8 antibody to Hssh3bp1. Staining is intense in both normal tissues shown (FIGS. 15A and 15C) and in tumor tissue from case 400 (FIG. 15D), which was not deleted for 10p loci. Note the complete absence of staining in the malignant tissue from case 398 (FIG. 15B), which also demonstrated deletion of sequences adjacent to the Hssh3bp1 locus on 10p. The large panels are shown at ×100 magnification; insets are at ×400 magnification.

Total genomic DNA was isolated from the indicated sources below and subjected to PCR amplification using the indicated primers (PCR primers). PCR fragments were separated on 1% agarose gel (FIG. 14). Sequencing of the PCR product bands was performed using primer DL75' (forward sequencing primer; SEQ ID NO:7), which is located upstream of 5'loxP site, and with primer Flankneo13' (reverse sequencing primer; SEQ ID NO:4), which is located downstream of 3'loxP site. Names of MEF cell lines and mice are indicated.

Primary MEF Cell Lines

"RARA1" is the obtained from a mouse embryo resulting from breeding of heterozygous Abi1/Hssh3bp1 (loxP/+) strain and genotyped to be negative for the loxP allele. Sequencing data confirms the lack of a 5'loxP site and lack of a 3'loxP site in the WT sequence of the Abi1/Hssh3bp1 gene.

"RARA3" is obtained from a mouse embryo resulting from breeding of heterozygous Abi1/Hssh3bp1 (loxP/+) strain and genotyped to be homozygous for the loxP allele. Sequencing confirms the presence of a 5'loxP site and a 3'loxP site in the recombinant Abi1/Hssh3bp1 gene.

"RARA7" is obtained from mouse embryo resulting from breeding of heterozygous Abi1/Hssh3bp1 (loxP/+) strain and genotyped to be heterozygous for the loxP allele and the wild type allele. Sequencing confirms the presence of both 5' and 3' loxP sites. Also, the WT sequence was confirmed with the DL75' and Flankneo13' primers.

Where indicated, the term "upper band" refers to sequence data from the recombinant Abi1/Hssh3bp1 floxed allele and the term "lower band" refers to sequence data from the wild type Abi1/Hssh3bp1 gene allele.

Sequencing data from primary MEF cell lines confirmed the presence of 5'loxP and 3'loxP sites and the lack of neomycin gene in the recombinant Abi1/Hssh3bp1 floxed gene.

Immortalized MEF Cell Lines

MEF#3 (parental #3 MEF Abi1/Hssh3bp1 floxed cell line): Sequencing confirmed the presence of both 5' and 3' loxP sites in the recombinant Abi1/Hssh3bp1 gene.

MEF#3 clones #3-6, #3-8 and #3-11: Sequencing confirmed the deletion of exon 1 and the presence of only one loxP site in the recombinant Abi1/Hssh3bp1 gene.

MEF#8 (parental #8 MEF Abi1/Hssh3bp1 floxed cell line): Sequencing confirmed the presence of both 5' and 3' loxP sites in the recombinant Abi1/Hssh3bp1 gene.

MEF# * clones #8-7 and #8-11: Sequencing confirmed the deletion of exon 1 and the presence of only one loxP site in the recombinant Abi1/Hssh3bp1 gene.

Sequencing data from the immortalized MEF cell lines confirmed the presence of 5'loxP and 3'loxP sites and the lack of neomycin gene in the recombinant Abi1/Hssh3bp1 floxed gene allele in parental #3 and #8 cell lines. In cell lines subcloned following transient Cre recombinase transfection (#3-6, #3-8, #3-11 from the parental MEF #3 and #8-7 and #8-11 from the parental MEF #8), the Abi1/Hssh3bp1 gene sequence located between loxP sites including exon 1 and including one loxP site is deleted from the recombinant allele. This resulted in disruption of Abi1/Hssh3bp1 protein expression (see the FIG. 6 for protein expression data from #3 subclones).

Prostate Tissue from Abi1/Hssh3bp1 Floxed Mouse Crossed with PbCre Mice and Positive for Cre Recombinase Expression Mouse #418 anterior and posterior prostate: Sequencing confirmed the presence of both 5' and 3' loxP sites in the recombinant Abi1/Hssh3bp1 gene.

Prostate Tissue from Control Abi1/Hssh3bp1 Floxed Mouse Crossed with PbCre Mice but Negative for Cre Recombinase Expression Mouse #419 anterior and posterior prostate: Sequencing confirmed the presence of both 5' and 3' loxP sites in the recombinant Abi1/Hssh3bp1 gene.

For these tissues the term "upper band" refers to sequence data from the floxed allele and the term "lower band" refers to sequence data from the exon 1 deleted allele.

Sequencing data from the mouse prostate tissue confirmed the presence of 5'loxP and 3'loxP sites and the lack of neomycin gene in the recombinant Abi1/Hssh3bp1 floxed gene allele in anterior and posterior prostate tissues in animals #418 and #419. In prostate tissues obtained from the mouse expressing probasin-driven (i.e. prostate specific) Cre recombinase (mouse #418), Cre recombinase-mediated deletion of the Abi1/Hssh3bp1 gene sequences was observed located between loxP sites and including exon 1 and one loxP site.

Example 5

Abi1/Hssh3bp1 Knock-Out Mouse

Mice homozygous for the recombinant floxed Abi1/Hssh3bp1 allele were bred with a probasin promoter driven Cre recombinase (Pb-Cre) expressing strain: B6.D2-Tg(Pbsn-Cre)4Prb (National Cancer Institute-Frederick; the Mouse Repository of the Mouse Models of Human Cancers Consortium). In these transgenic mice, the prostate-specific promoter of the rat probasin gene (Pb) regulates expression of Cre recombinase, hence the enzyme is expected to be expressed only in mature prostate-tissue. The Pb-Cre strain is maintained in the hemizygous state by breeding to C57BL/6J females. Cre must be transmitted through the male mice to avoid small, but significant oocyte-mediated recombination. Breeding pairs were supplied as a hemizygous male and a female C57BL/6N mate. Successive generations of Pb-Cre mice were bred to C57BL/6J mice to generate sufficient Pb-Cre mice for experiments. Mice were genotyped using tail-obtained DNA.

Figure 13:
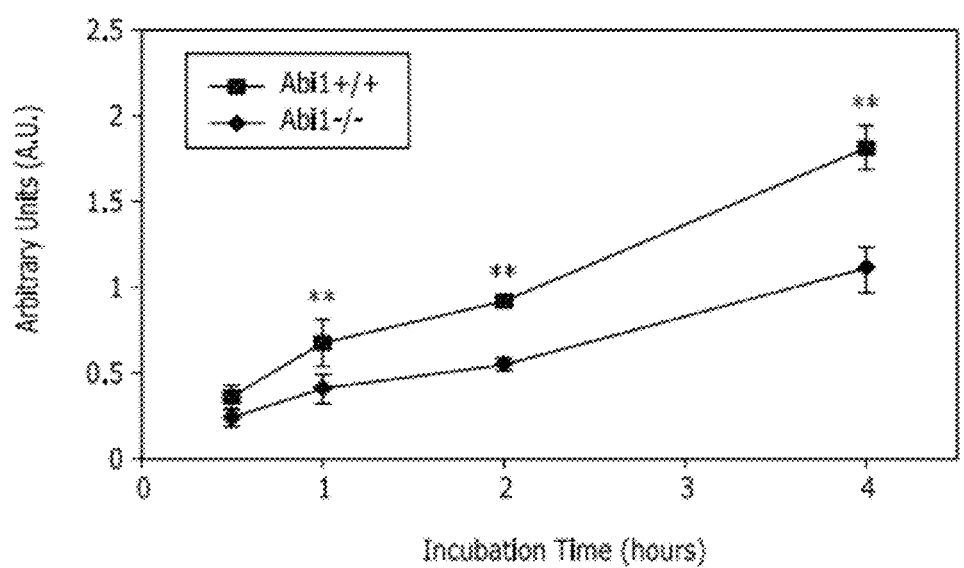
FIG. 13 depicts the activity of mitochondrial dehydrogenase in Abi1−/− and Abi1+/+ MEF cells (**p<0.01).

Prostate specific deletion of Abi1/Hssh3bp1 exon 1 was confirmed in prostate tissue by genotyping with primers DL75' and Flankneo13' (FIG. 13). This result confirms the functionality of the loxP sites in vivo, and demonstrates the suitability of these mice for studies of Abi1/Hssh3bp1 gene function.

Example 6

Proliferation of Cells Lacking Abi1/Hssh3bp1

The proliferation rates of cells lacking Abi1/Hssh3bp1 are higher than control Abi1/Hssh3bp1(fl/fl) MEF cells. Loss of Abi1/Hsshb3p1 in primary prostate tumors and subsequent identification of primary tumor mutations that lead to disruption of Abi1/Hsshb3p1 function suggested that loss of Abi1/Hsshb3p1 protein leads to dysregulation of cell growth. This was tested using MEF cells isolated from the Abi1/Hssh3bp1 CKO mice. Consistent with the tumor suppressor hypothesis, enhanced proliferation rates as determined by activity of mitochondrial dehydrogenase were observed in MEF Abi1/Hsshb3p1 (−/−) cells (clone #3-11) in comparison to parental clone #3 Abi1 (+/+) (FIG. 13). Primers DL75' and Flank-neo13' were used for genotyping.

Example 7

Role of Abi1/Hssh3bp1 in Prostate Cancer

The deletion of specific chromosomal regions has been reported in human prostatic tumors. For chromosome 10, both the 10p and 10q arms have been reported as frequently deleted. Deletions on 10q often involve the 10q23-24 region, including sequences mapped to the candidate prostate tumor suppressor gene, PTEN or MMAC1. Loss of heterozygosity (LOH) on the short arm of chromosome 10, 10p, has also been observed in prostate tumors. Several studies performed using polymorphic markers indicated high rates of LOH specifically in the 10p11.2 region. The rate of LOH varies among the studies, dependent upon the marker used and the stages of the cancers examined. Genetic alterations on 10p are often present in conjunction with the changes on 10q. An extensive deletion mapping of 10p in human prostate tumors at 13 highly polymorphic loci has been performed. In this study, 57% of 35 tumors examined demonstrated loss of 10p sequences. The highest concentration of allelic losses on 10p spanned a 4- to 7-cM region and included loci D10S211, D10S89, and D10S111, which defined a minimal common region of deletion on 10p in human prostate tumors. Moreover, this study suggested that one or more deletion domains may map to 10p, as some tumors were deleted exclusively at D10S211 or D10S89-D10S111. These studies were confirmed by the observation that the LOH of 3.2% in localized (Stage B) and LOH of 27% in advanced prostate cancer (Stages C and D) using the marker D10S111. Taken together, these allelotyping studies suggest that one or more tumor suppressor genes map to 10p in human prostate tumors. Functional studies supporting this hypothesis were provided by studies in prostate cell lines supplemented with portions of chromosome 10p. The introduction of subchromosomal fragments encompassing 10pter-q11 into the PC3 prostate adenocarcinoma cell line reduced tumorigenicity following injection of hybrid clones in nude mice. Similar results were obtained by another group using the PPC-1 cell line, a subline of PC3, in which decreased colony formation in soft agar was observed following introduction of 10p sequences.

Thus, both allelotyping and functional studies suggest that one or more tumor suppressor genes critical for prostate tumorigenesis map to 10p inclusive of the D10S89 and D10S111 loci. The minimal common region of deletion on 10p in human prostate tumors contains a gene encoding a candidate human spectrin SH3 domain binding protein 1, Hssh3bp1. Hssh3bp1 binds to SH3 domains of spectrin and Abl tyrosine kinase, associates with macropinocytic vesicles in cultured cells, and is a potential regulator of macropinocytosis. E3b1, a protein identified independently by another group as Eps8 binding protein and which is identical to isoform 2 of Hssh3bp1, was recently implicated in transmission of signals from Ras to Rac. Hssh3bp1 maps near loci D10S89 and D10S111 within the 10p minimal region of deletion observed in prostate cancer, and all three sequences localize to a single YAC, 961C7. Moreover, Hssh3bp1 protein expression is downregulated in prostate tumors deleted for D10S89 or D10S111. Two prostate tumor cell lines contain a mutation in Hssh3bp1 gene leading to expression of the aberrant form of Hssh3bp1. These data are consistent with a role for Hssh3bp1 as a candidate tumor suppressor gene inactivated during prostate tumorigenesis.

DNA Analysis

Colonies from each of 11 CEPH YACs (965D10, 746D9, 815C7, 747H10, 857C9, 934E11, 796F8, 899E10, 875B4, 746G7, and 961C7), comprising a complete contig of the 10p minimal region of deletion, were picked and incubated in 10 μl of lyticase solution (1.2 M sorbitol, 10 mM sodium phosphate, pH 7.4 [1:4 v/v monobasic: dibasic from 1 M stocks]) and 2.5 mg/ml lyticase (Sigma) at 37° C. for 5 min. Five microliters of each digestion mixture was used in subsequent polymerase chain reaction (PCR) comprising 200 μM each dGTP, dATP, dTTP, and dCTP; 1× PCR buffer (50 mM KCl, 10 mM Tris-HCl, pH 8.3, 2.5 mM $MgCl_2$); 1 μM each forward and reverse primers, and 0.6 U Taq Polymerase (Life Technologies) using an annealing temperature of 55° C. The linkage order of these markers has been reported as: pter-D10S211-WI4906-10S553-D10S1789-D10S550-WI4133-D10S582-D10S1673-D10S586-D10S1749-D10S1747-D10S572-D10S89-D10S111-centromere.

Primer sequences and linkage information were obtained from databases maintained by the Human Genome Data Base E-mail: (http://gdbww-w.gdb.org/), Center for Genome Research at the Whitehead Institute for Biomedical Research E-mail: (http://www-genome.wi.mit.edu/), and the National Center for Biotechnology Information (http://www.ncbi.nlm.nih.gov/). The Hssh3bp1 forward primer used was PROM 35' (5'-CTGCAGAGACCCATGATTGTGCC-3', SEQ ID NO:8), and the reverse primer used was PROM 53' (5'-CAAGTTGAGTACGAATACTCCGTAC-3', SEQ ID NO:9). Reaction products were electrophoresed on 2.5% agarose and visualized after ethidium bromide staining.

The Hssh3bp1 exon 6 sequences were amplified from genomic DNA isolated from prostate cell lines using forward primer Ex615' (5'-CAAAGGGAGACTCACATA TTTT TGG-3', SEQ ID NO:10), and the reverse primer Ex613' (5'-TCCATAGGAGT TTGTCGCCAGTCAG-3' (SEQ ID NO:11) and sequenced. The primer sequences were derived from Contig NT 008730 (Gen-Bank) containing the entire Hssh3bp1 gene (see also AceView of the gene at NCBI web site at the address indicated above).

Analysis of Hssh3bp1 Expression

Frozen paired normal and tumor prostatic tissues previously characterized for 10p dosage status were utilized. Monoclonal antibody (mAb) 2G8 was raised to the recombinant C-terminal portion of Hssh3bp1, plasmid C5 at the Institute for Basic Research in Developmental Disabilities Antibody Facility using standard techniques. Immunohistochemistry was performed in 5 micron sections, which were cut from paired frozen normal and malignant tissues from radical prostatectomy specimens, fixed for 10 minutes in ice-cold acetone, then air-dried briefly at 4° C. The slides were stained with a 1:2000 dilution of mAb 2G8 using a Ventana 320 ES Automatic Immunohistochemistry/IPOX Staining Station according to manufacturer's protocols. The antibody staining was evaluated by a pathologist, and the degree of staining was assessed as 0 (absent), 1 (weak), 2 (moderate), or 3 (strong).

markers D10S89 and D10S111. Because D10S89 also localizes to a more telomeric YAC, 875B4, the likely sequence order is: 10pter-D10S89-Hssh3bp1/D10S111-10cen, where "/" indicates that the actual orientation is unclear (Table 1). The relatively small size of YAC 961C7, which is 1.67 Mb, suggested the possibility that the Hssh3bp1 gene may be co-deleted in tumors deleted for D10S89 or D10S111.

TABLE 1

YAC Contig of 10p Prostate Cancer Minimal Deletion Region.

| YAC Designation | D10S211 | WI-4906 | D10S553 | D10S1789 | D10S550 | WI-4133 | D10S582 | D10S1673 |
|---|---|---|---|---|---|---|---|---|
| 965-D-10 | + | | | | | | | |
| 746-D-9 | + | | | | | | | |
| 815-C-7 | + | + | | | | | | |
| 747-H-10 | | + | + | | | | | |
| 857-C-9 | | | + | + | + | + | + | + |
| 934-E-11 | | | | + | + | + | + | + |
| 796-F-8 | | | | + | + | + | + | + |
| 899-E-10 | | | | | | | | |
| 875-B-4 | | | | | | | | |
| 746-G-7 | | | | | | | | |
| 961-C-7 | | | | | | | | |

| YAC Designation | D10S586 | D10S1749 | D10S1747 | D10S572 | D10S89 | Hssh3bp1 | D10S111 |
|---|---|---|---|---|---|---|---|
| 965-D-10 | | | | | | | |
| 746-D-9 | | | | | | | |
| 815-C-7 | | | | | | | |
| 747-H-10 | | | | | | | |
| 857-C-9 | | | | | | | |
| 934-E-11 | + | + | + | | | | |
| 796-F-8 | | | | | | | |
| 899-E-10 | + | + | + | | | | |
| 875-B-4 | | | | | + | + | |
| 746-G-7 | | | | | | + | |
| 961-C-7 | | | | | + | + | + |

YAC clones are listed on the left and chromosome 10p loci are listed on the top. YAC 961-C-7 contains D10S89, Hssh3bp1, and D10S111. The analysis was done by PCR using specific primers.

Protein Truncation Test (PTT)

Prostate cell lines LNCAP.FGC-10 (CRL-10995), LNCaP.FGC (CRL-1740), and PC3 (CRL 1435) were obtained from ATCC and were grown according to ATCC instructions. RNA from cultured cells was prepared using Tri-Reagent (Molecular Research Center). RT-PCR was performed using Hssh3bp1-specific primers T7-M (5'-GAT-TAATACGACTCACTATAGGGACGC-GAGAGGAAGCGATGCAGAG-3', 5' primer; SEQ ID NO:12) and P3 (5'-CTTGAATTCAAGCAAATCAGT-GAAGGAAAGGAC-3', 3' primer; SEQ ID NO:13). In vitro translation of gel-purified PCR products (200 ng) was performed using T7-h1 primer and T7 TNT System (Promega). SDS-PAGE protein electrophoresis and Western blotting were performed. Polyclonal antibody Ab-2 to Hssh3bp1 was used in the analysis.

Hssh3bp1 Maps to the 10p Minimal Common Region of Deletion in Prostate Tumors

Figure 16:
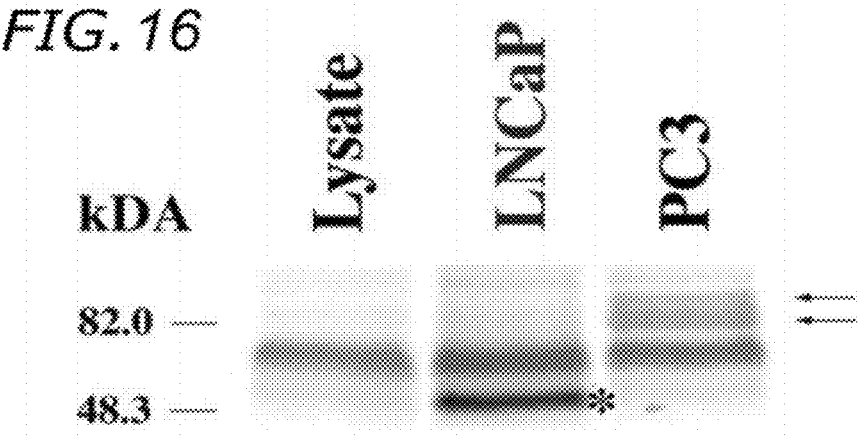
FIG. 16 depicts protein truncation test of Hssh3bp1 in prostate tumor cell lines by in vitro translation of Hssh3bp1 cDNA using rabbit reticulocyte lysate. Reaction mixtures following in vitro translation of PCR products were separated on 7% Tricine SDS polyacrylamide gel; the gel was blotted with the polyclonal antibody Ab-2 to Hssh3bp1. Lane 1, reaction mixture without addition of exogenous DNA; lane 2, reaction mixture containing Hssh3bp1 cDNA from LNCaP; lane 3, reaction mixture containing Hssh3bp1 cDNA from PC3. Apparently the rabbit reticulocyte lysate contains an Ab-2 antibody reactive band (lane 1). Arrows indicate the full-length Hssh3bp1 polypeptides representing isoforms 2 and 3 of Hssh3bp1 as confirmed by PCR analysis (not shown). Asterisk indicates a truncated polypeptide.

Each of 11 CEPH YACs was amplified for 14 loci mapping within the 10p minimal common region of deletion. These experiments ordered the YACs into a contig spanning this region (Table 1). The Hssh3bp1 gene localized exclusively to YAC 961C7, which also contains sequences specific for Hssh3bp1 Expression is Downregulated in Prostate Tumors Deleted for Adjacent 10p Sequences Immunohistochemical analysis of prostate tissues using a mAb to Hssh3bp1 was performed to determine whether Hssh3bp1 protein expression correlated with D10S89 or D10S111 dosage in prostate tumors. Seventeen paired normal and malignant prostate specimens previously characterized for dosage at D10S89 and D10S211 were utilized for these studies. Of the 17 tumor tissues, six were characterized by deletions at D10S89 or D10S111 (Table 2). The remaining 11 tumors retained normal diploid dosage at D10S89, D10S111, or both loci (Table 2). Immunohistochemical staining of epithelial cytoplasm was graded into four groups: absent (0), weak (1), moderate (2), or strong (3). Moderate or strong expression of Hsshb3p1 was detected in 82% (14/17) of normal tissues examined (Table 2). In contrast, moderate or strong expression of Hssh3bp1 was detected in only 41% (7/17) of malignant tissues examined. Moreover, 4/6 (67%) tumors deleted for 10p sequences at D10S89 or D10S111, within the minimal common region of deletion, failed to express Hssh3bp1 protein compared to 5/11 (46%) tumors that retained normal diploid dosage at these loci. An example of Hssh3bp1 staining in normal and malignant is shown in FIG. 16.

TABLE 2

Expression of Hssh3bp1 in Prostate Tumors.

| Case Number | 10p Deletion* | Antibody Staining† Normal | Antibody Staining† Tumor | Correlation with 10p Status | Tumor Grade‡ | Tumor Stage§ |
|---|---|---|---|---|---|---|
| 404 | yes | 3 | 3 | no | 3 + 3 | T2b |
| 334 | yes | 2 | 0 | yes | 3 + 3 | T2b |
| 340 | yes | 2 | 0, 2¶ | yes | 3 + 4 | T2b |
| 398 | yes | 1-2 | 0 | yes | 3 + 3 | T2 |
| 408 | yes | 3 | 0 | yes | 3 + 4 | T2 |
| 394 | yes | 2 | 3 | no | 3 + 3 | T1b |
| 344 | no | 1 | 1 | yes | 3 + 3 | T2 |
| 402 | no | 3 | 3 | yes | 4 + 3 | T3N1 |
| 244 | no | 0 | 2 | no | 3 + 3 | T3 |
| 390 | no | 3 | 3 | yes | 3 + 3 | T3 |
| 260 | no | 2-3 | 1 | no | 3 + 4 | T2b |
| 392 | no | 1 | 0 | no | 3 + 3 | T2 |
| 400 | no | 3 | 3 | yes | 3 + 3 | T3 |
| 386 | no | 3 | 0 | no | 3 + 3 | T3N1 |
| 380 | no | 2 | 1 | no | 3 + 4 | T3 |
| 320 | no | 2 | 2 | yes | 3 + 4 | T2 |
| 268 | no | 3 | 1, 3¶ | no | 3 + 3 | T2b |

*10p deletion was characterized as described [6]. "no" indicates that the tumors were not deleted at 10p or were uninformative at one or more loci.
†Mab 2G8 was used in all cases. (0) Absent; (1) weak; (2) moderate; (3) strong.
‡According to Gleason score.
§According to TNM system.

Taken together, these experimental results show that the loss of Hsshb3p1 protein expression was clearly associated with the deletion of adjacent loci on 10p deletion in human prostate tumors.

Prostate Tumor Cell Lines Contain Mutations in Hssh3bp1

PTT was performed in two prostate tumor cell lines, LNCaP (CRL-10995) and PC3 (CRL-1435). The PTT test used an antibody to the C-terminus of Hssh3bp1 and indicated the presence of a truncated polypeptide in LNCaP cell line in comparison to two polypeptides in the PC3 cell line (FIG. 16). As determined by DNA sequencing, the LNCaP cell line, but not the PC3 cell line, contains deletion of nucleotides 660-800 (total of 141 nucleotides) of the Hssh3bp1 cDNA. This results in the in-frame deletion of amino residues 194 through 240 of Hssh3bp1 and is consistent with the observation of a smaller translation of product in the PTT. Identical deletion of Hssh3bp1 sequences was observed in another tumor cell line, CRL-1740. Sequencing of Hssh3bp1 gene from these cell lines revealed the presence of a heterozygous point mutation in exon 6 of the gene located near the 3' splice junction of the preceding intron: the sequence TAG↓ACGG is now TAG↓ACAG, where italic indicates intronic sequence, an arrow splice site, and underline/bold mutated residue. The mutation causes codon 194 change from R (CGG) to Q (CAG). This missense mutation apparently led to exon 6 skipping in the splicing of Hssh3bp1 mRNA, which may be explained by at least two independent mechanisms: a missense-induced exon skipping or by a conformational change in Hssh3bp1 mRNA near the 3' splice site. PCR analysis of Hssh3bp1 cDNA in PC3 cells using isoform-specific primers revealed expression of isoforms 2 and 3 of Hssh3bp1, which is consistent with the observation of two closely spaced polypeptides (FIG. 16). Apparent migration of the polypeptide from LnCAP cells corresponds to migration of isoform 5 of Hssh3bp1 lacking amino acid sequence encoded by exon 6.

Previous allelotyping and functional studies suggested that one or more tumor suppressor genes important for prostate tumorigenesis mapped to the 10p chromosomal region. The Hssh3bp1 gene was mapped adjacent to loci D10S89 and D10S111 within the 10p minimal region of deletion previously defined by our laboratory for prostate tumors. Moreover, expression of the Hssh3bp1 protein was reduced in the majority of prostate tumors deleted for either D10S89 or D10S111. These studies suggest that the observed reduction of Hssh3bp1 protein expression may be due to the allelic inactivation of the gene through the deletion of one copy and mutation of the remaining copy. This mechanism is consistent with that of the "two-hit" model originally proposed for the "prototype" tumor suppressor gene, retinoblastoma. Therefore, Hssh3bp1 is a candidate tumor suppressor gene important for prostate tumorigenesis.

The co-localization of Hsshb3p1 sequences with D10S89 and D10S111 within the 10p minimal common region of deletion in prostate cancer suggests that expression of Hssh3bp1 may be lost in prostate tumors. This is supported by the immunohistochemical studies presented here which show that Hssh3bp1 protein expression is absent or reduced in the majority (5/6, 83%) of prostate tumors examined with deletions of D10S89 or D10S111, but is expressed in the majority of normal tissues and prostate tumors intact at these loci.

Two mechanisms that may account for the observed reduced expression of Hssh3bp1 protein in conjunction with the deletion of adjacent 10p loci include deletion and/or mutation of Hssh3bp1 sequences. Other mechanisms may also be involved, however. For example, five tumors (cases 344, 260, 392, 386, and 380) failed to express Hssh3bp1 protein, though they did not exhibit deletion of D10S89 or D10S111. In these cases, it is possible that Hssh3bp1 expression was downregulated through other means, e.g., small interstitial deletions, mutations involving both Hssh3bp1 alleles, transcriptional downregulation, or reduced protein stability. Significantly, these proposed events are apparently specific to prostate tumors, as the vast majority of normal prostate epithelial specimens (14/17, 82%) exhibited moderate or strong Hssh3bp1 protein expression. It should also be noted, as an exception, that one tumor (case 404), deleted for one allele at both D10S89 and D10S111, expressed high levels of Hssh3bp1 protein. It is possible that deletion affected only one allele of Hssh3bp1 in this tumor, allowing normal expression of the remaining allele.

Two prostate tumor LnCAP cell lines, CRL-10995 and CRL-1740, contain a missense mutation in exon 6 of Hssh3bp1. These cell lines are derivative of each other, which is why the same mutation in the gene was observed. This mutation leads to an apparent exon 6 skipping resulting in expression of aberrant form of Hssh3bp1 mRNA and protein. Although the exon 6 mutation is observed in one allele of Hsshb3p1 gene, only expression of the truncated polypeptide is observed in these cells, suggesting downregulation of the normal allele by mechanisms mentioned in the previous paragraph. Exon skipping was demonstrated to be due to nonsense or missense mutations located in exonic splice enhancers present in both constitutively and alternatively spliced exons in genes such as BRCA1 and others. The identified mutation may also affect RNA secondary structure and conformation required for appropriate splicing of exon 6 since it is located at the +3 position from the 3' splice junction of the preceding intron. The presence of exon 6 sequences is invariably observed in Hssh3bp1 cDNA obtained from various tissues including primary prostate cells, PC3 cells, human brain, as well as several cultured cell lines. Alternative splicing of Hssh3bp1 in brain leads to five isoforms of the mRNA coding region with additional possibility of alternative splicing of the 3' untranslated region. Expression of specific Hssh3bp1 isoforms in different cells may be functionally significant and is different in PC3 than in LnCAP cell lines.

Lack of exon 6 sequences that encode amino residues 194 through 240 of Hssh3bp1 results in the loss of a portion of Abl tyrosine kinase SH3 domain binding site (amino residues 144-260 of Hssh3bp1) in Hssh3bp1 in LnCAP cell lines. Such deletion may affect subcellular localization of Abl tyrosine kinase and alter its kinase activity, resulting in cellular transformation. This hypothesis is consistent with the fact that mutations of the Abl SH3 domain lead to the increased transformation ability of Abl Consistent with the proposed tumor suppressor function, Hssh3bp1 may be a negative regulator of the function of Abl tyrosine kinase, an oncogene.

Previous studies identified Hssh3bp1 as a marker of macropinocytic vesicles. In addition, overexpression of Hssh3bp1 decreased endocytosis of a fluorescent dye, suggesting a potential negative regulatory role of Hssh3bp1 in macropinocytosis. Macropinocytosis is upregulated in tumor cell lines by stimulation with growth factors, and PI-3 kinase is a positive regulator of the process. LY294002, a specific inhibitor of PI-3 kinase, blocks endocytosis of fluorescent dyes into Hssh3bp1 macropinosomes and dramatically affects their morphology. This suggests that Hssh3bp1 is involved in a transduction pathway involving PI-3 kinase. PI-3 kinase function is, in turn, opposed by PTEN/MMAC, a tumor suppressor gene implicated in prostate tumorigenesis. Thus, Hssh3bp1 and PTEN may be located in the same signal transduction pathway affected in prostate cancer. Thus, down-regulation of Hssh3bp1 may be a downstream event of abberant regulation of PTEN or PI-3 kinase. Downregulation of Hssh3bp1 protein expression may also occur independently through a deletion and, possibly, mutation mechanism.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

I claim:

1. A knock-out mouse for use in screening compounds for anti-cancer activity, wherein said mouse contains a prostate-specific disruption in exon 1 of an Abi interactor 1 (Abi-1) gene, and said disruption results in an inability of said mouse to produce detectable levels of the Abi-1 protein in said prostate tissue and said mouse develops prostatic intraepithelial neoplasia.

2. The knock-out mouse of claim 1 wherein said Abi1 gene is only disrupted in the mouse's prostate tissue expressing a Cre recombinase.

3. The knock-out mouse of claim 1, wherein the disrupted Abi-1 gene comprises a recombinant Abi-1 allele, a selectable marker, frt sites flanking the selectable marker, and loxP sites flanking a portion of the allele.

4. The knock-out mouse of claim 1 wherein said Abi-1 gene is not expressed in only a portion of the mouse's tissues.

5. The knock-out mouse of claim 1 wherein a prostate cell in said mouse exhibits at least one alteration selected from the group consisting of disruption of cell motility, increased directional persistence, decreased migration distance, and decreased migration rate.

6. A cell isolated from the mouse of claim 1.

7. The cell of claim 6 wherein the cell is from the mouse's prostate tissue.

8. A mouse Abi-1 gene knock-out construct comprising:
a) a portion of a mouse Abi-1 gene, wherein exon 1 of said Abi-1 gene is flanked by 3' and 5' loxP sites;
b) a selectable marker between exon 1 and the 3' loxP site;
c) frt sites 5' and 3' to the selectable marker; and
d) an additional loxP site 3' to the 5' frt site,
wherein the construct comprises SEQ ID NO: 14.

9. A method of producing a knockout mouse with a prostate-targeted disruption in an Abi-1 gene, comprising the steps of:
transfecting the knockout gene construct of claim 8 into a population of murine embryonic stem (ES) cells;
selecting a transfected ES cell which expresses said selectable marker;
introducing said transfected ES cell into an embryo of an ancestor of said mouse;
allowing said embryo to develop to term to produce a chimeric mouse with a conditional knock-out construct in its germ line;
breeding said chimeric mouse to produce a heterozygous mouse with a conditionally disruptable Abi-1 gene; and
breeding said heterozygous mouse with a mouse expressing flippase or Cre recombinase only in prostate tissue to produce a mouse with a prostate-specific disruption in the Abi-1 gene, wherein the prostate tissue does not contain said selectable marker and wherein said mouse develops prostatic intraepithelial neoplasia.

* * * * *

UNITED STATES PATENT AND TRADEMARK OFFICE
CERTIFICATE OF CORRECTION

Page 1 of 1

PATENT NO. : 8,110,719 B2
APPLICATION NO. : 12/430814
DATED : February 7, 2012
INVENTOR(S) : Kotula It is certified that error appears in the above-identified patent and that said Letters Patent is hereby corrected as shown below:

In the specification
Column 1, lines 14 - 18, delete "The invention was made with Government support under Grant No. W81XWH-08-1-0320 awarded by the Department of Defense and Grant No. R01 NS044968 from the National Institute of Health. The Government may have certain rights in this invention." and insert --This invention was made with government support under Grant W81XWH-08-1-0320 awarded by the Department of Defense and Grant R01 NS044968 awarded by the National Institute of Health. The government has certain rights in the invention.--.

Signed and Sealed this
Nineteenth Day of January, 2016

Michelle K. Lee
*Director of the United States Patent and Trademark Office*

SEQUENCE LISTING

<160> NUMBER OF SEQ ID NOS: 20

<210> SEQ ID NO 1
<211> LENGTH: 20
<212> TYPE: DNA
<213> ORGANISM: Artificial
<220> FEATURE:
<223> OTHER INFORMATION: Primer

<400> SEQUENCE: 1
ccagaggcca cttgtgtagc                                              20

<210> SEQ ID NO 2
<211> LENGTH: 22
<212> TYPE: DNA
<213> ORGANISM: Artificial
<220> FEATURE:
<223> OTHER INFORMATION: Primer

<400> SEQUENCE: 2
ctggaagctg acaagaggat ag                                           22

<210> SEQ ID NO 3
<211> LENGTH: 31
<212> TYPE: DNA
<213> ORGANISM: Artificial
<220> FEATURE:
<223> OTHER INFORMATION: Primer

<400> SEQUENCE: 3
aataatttaa tagttctggt gatatgacag c                                 31

<210> SEQ ID NO 4
<211> LENGTH: 22
<212> TYPE: DNA
<213> ORGANISM: Artificial
<220> FEATURE:
<223> OTHER INFORMATION: Primer

<400> SEQUENCE: 4
gggcagacgg cgagaagcag ag                                           22

<210> SEQ ID NO 5
<211> LENGTH: 27
<212> TYPE: DNA
<213> ORGANISM: Artificial
<220> FEATURE:
<223> OTHER INFORMATION: Primer

<400> SEQUENCE: 5
gctacacaag tggcctctgg cctcgca                                      27

<210> SEQ ID NO 6
<211> LENGTH: 24
<212> TYPE: DNA
<213> ORGANISM: Artificial
<220> FEATURE:
<223> OTHER INFORMATION: Primer

<400> SEQUENCE: 6
atgtgtcagt ttcatagcct gaag                                         24

<210> SEQ ID NO 7
<211> LENGTH: 24
<212> TYPE: DNA

<210> SEQ ID NO 7
<211> LENGTH: 24
<212> TYPE: DNA
<213> ORGANISM: Artificial
<220> FEATURE:
<223> OTHER INFORMATION: Primer

<400> SEQUENCE: 7
tagggtacaa attatccttg cttc        24

<210> SEQ ID NO 8
<211> LENGTH: 23
<212> TYPE: DNA
<213> ORGANISM: Artificial
<220> FEATURE:
<223> OTHER INFORMATION: Primer

<400> SEQUENCE: 8
ctgcagagac ccatgattgt gcc        23

<210> SEQ ID NO 9
<211> LENGTH: 25
<212> TYPE: DNA
<213> ORGANISM: Artificial
<220> FEATURE:
<223> OTHER INFORMATION: Primer

<400> SEQUENCE: 9
caagttgagt acgaatactc cgtac        25

<210> SEQ ID NO 10
<211> LENGTH: 25
<212> TYPE: DNA
<213> ORGANISM: Artificial
<220> FEATURE:
<223> OTHER INFORMATION: Primer

<400> SEQUENCE: 10
caaagggaga ctcacatatt tttgg        25

<210> SEQ ID NO 11
<211> LENGTH: 25
<212> TYPE: DNA
<213> ORGANISM: Artificial
<220> FEATURE:
<223> OTHER INFORMATION: Primer

<400> SEQUENCE: 11
tccataggag tttgtcgcca gtcag        25

<210> SEQ ID NO 12
<211> LENGTH: 46
<212> TYPE: DNA
<213> ORGANISM: Artificial
<220> FEATURE:
<223> OTHER INFORMATION: Primer

<400> SEQUENCE: 12
gattaatacg actcactata gggacgcgag aggaagcgat gcagag        46

<210> SEQ ID NO 13
<211> LENGTH: 33
<212> TYPE: DNA
<213> ORGANISM: Artificial
<220> FEATURE:
<223> OTHER INFORMATION: Primer

<400> SEQUENCE: 13
cttgaattca agcaaatcag tgaaggaaag gac        33

<210> SEQ ID NO 14
<211> LENGTH: 31172
<212> TYPE: DNA
<213> ORGANISM: Artificial
<220> FEATURE:
<223> OTHER INFORMATION: Abi1/Hssh3bp1 full length conditional allele

<400> SEQUENCE: 14

```
gtactttgct tttggctaca cttggagtta gattttaaga taagtaagta aggtaaaaat      60
gaaatgatta gactagggcc ctaattaaat acagctgagg tttttgtgtc attataaaaa     120
gaggaaaaga tacaagggtt ggatatgtga agagaaaatg ccgggtgagg cacacagat      180
tatcatgcaa ggtgagagcc tcaggagaaa ccttgtttgg gacttgtgtc acccagaact     240
atgagaaaaa cctttctgtt gtctgagcta cctttcagag aggggagaat gggcggttca     300
gctataaaga cgtgtgaaga aaaggccatg tgccctgact ctcttacttc ttcctgagtg     360
ggtgcctgca tcactgaggc tgtcatcaga cttcagattc tctagccttg caacaggaat     420
tgaatccttg tggttctcca gggagcttcc tggacagact gcggctgcgc ctccagcctt     480
gtggcccaag cagttggtga gttctcttcc tcttctgtgc cgacagctgt tggtacacaa     540
cccccaactt ctgtcctttg ccaatcaaat aactttctta ctgttctttc gctgtgaaga     600
aacaccatga ccatggcaac tcttaaaaaa gaaagccttt aactaggggc ttgcctatag     660
tttcagaaag ttagtccatt accatcgcag gaggggagca tggcagcagg caggcatggt     720
gctggagaga tagctgataa ctacatcctg atccttgggg gtgggggag aggggagag      780
agaggaggaa gggggagggg gagagggagg agagggagag ggagagacta agtcttgtgt     840
gggcttttaa aacctgaaag cccacccccca ttgacatatt tcctccaaca agaccacacc     900
tcctaatctt tctattgctt tcagacagtt ccattccctg gtgatgaagc attcaaatat     960
atgagcctct gggggcattc ttattgaaac catcacacta cacattatgt attttccttt    1020
cagtctattt ctctacataa ccctccctaa catgagaaat tatgccatat ggggatggtg    1080
gcaatgcaag tggtgggagt attttggagg gtgcaggaca gatgggggag tggttctgcc    1140
ttcctgactg ctagtttctt tccagtatat cacgtcgcca ttctggattc tagcttgctg    1200
accacctact tagcatcctg gtacacagtg ctgtgaatta tctacacaga aagtaaaaac    1260
aaaaaacaaa cagaaagcag agttctgaag tttttcagt gtaatgtgcc agataatatc    1320
agcaattatg taccaaaata atccaaatta taatttttttt gcctgtcaca tcacacatct    1380
cttttttgtag acatgatttt tgatgaaatc atttgtttg taacccaggc tgacttccaa    1440
caggcaaatc tactggttca acctcccaag tgctagagtt gtaatggcat attaccaggc    1500
ttagctacat agctgatctc tttatctctc tgaagcaacg tccatcattg tcagctatct    1560
actgtcttaa aactcaacct gtaaaatgtt ttcccatctg tccagaatgt gcacttcaca    1620
aactttttta ttaccaaatt aatttgctta tgtccattaa aagaagggta caggtgctag    1680
ggaatctagc ttagctggat tagtgcctgg tatgcataaa gcctagcttt agcccccagc    1740
acttcataaa gcaagatgtg gtggcacata tctgtaatcc cagtactgag aagatggaag    1800
caggaggatc agttcaaggc taccattggg tacatactaa gtttgaggct agcctagact    1860
acaacagact ttgtctcatt aaataagtaa ataaataaat ggttggattt acaggttgaa    1920
cactggcaaa agtcattaca tttaatacaa acactgttac tctttatttt attgcaattt    1980
cattttcttt tattttattc tggtacgtgt gtgtgtgtgt gtgtgtgtgt gtgtgatcac    2040
atgtgggaac atgtgtgggt acatgtacag gtatacttcc ctatagatat cttaaggtac    2100
```

```
tatagaatgt cttcttcaat cacattccat tttactttt tgttgttgtt gttttggttt    2160
ttcaagacag ggtttctctg tgtagccctg gctgtcctgg aactcactct gtagaccagg    2220
ctggcctcag aagtccacct gctttagcac aatactcttt aatacttgct taaatgaggc    2280
atggcagaaa tcagcctgtg atcctagcac ttgagccttg gaggatggtt caaggttgct    2340
ggagataact atgttaagag aaataaatca ggaacagaaa gggaaaaaaa aaaacacagt    2400
gttgtactta gctatagaga ggttcaagtc cacagtggat atgagaccct ctctcaagaa    2460
caagctaagt tattagatgc tattagtatt ttaaccttgt caaaaaaaca aaacaaaaca    2520
tggaaagcca tcagttataa tgtggtacct tgtcttatgg ttatcttcct acaggctggc    2580
tgtgaatgca ggaaactcct tgtctctagc tctcagttag ttattttctt cttttcttta    2640
gatttatttt gagtgttttg cctgtgtgta tgtctctgta ccacacccat gtcttctgtc    2700
tgcagaggtc agaagagggt ttcagatccc ctgggactgg gaattaggaa taattgtgaa    2760
ccattgtgtg gacactagga accaaaacac aggttatttg cacctcattc tttgggatgt    2820
gttgtttttc tttctttgtt gttgcattgg caatagtttc tccatacgct gtctgtctgg    2880
gacttttcta tatgcaccag accttcctca aactttcagt gatcgtcctg cctctgcctc    2940
accagtgctg gggcgacagg tatgtgcaac catgctagca tttaatttct tttgattag     3000
tatgcaaagt aatgagtttc actgtaacac tttcatgtat atactgcatt atatcccgag    3060
cttttgtccc cgccggcaag aacacactca ggacaaccgg aatcttctgt ggcaaagctt    3120
ttattgttta cttatcagga gggaagaccc cgaaccggga aaatggcgct gctcatatag    3180
cccgcagcgt gacgtttcag cacctgatgt ggtgtgacag ctcctgattc attgctcgcc    3240
catcacccca ttactacgcc gagagatggg cagtgactag gcgtgagttc actcttgcac    3300
ttgcgcataa ggcttgtcta ctagttaggc gcagtggaag ccagcgccat cttataatgg    3360
tgattgctca cggcacacac gcgattgctc gcggcacggc tcggctctcc acagcattac    3420
attggtaact ttatatataa ttatactttg ccattccaca actaccttcc ttcctcctgc    3480
tgactccacc cccacagcct gtgtttgcct ttatgtcaca tgtcacatgc tctttgttac    3540
cttcccttat tttgcttata cttcccttta gactttcttc ttcatgttca ccacaagctt    3600
cctaccttg tgttgttcct gcaaaacatg gctttcacct caaaggcaat ctgagataac     3660
tttcttttgt tactgttttg gctttctcta cttttagaca gggtatgtgt atagtccagg    3720
cctcaagctc acctggtatc tgaggatgac tttgaacaca tttgtcacat tgttgtttg     3780
ggggttttgt ttgttccttt gtttgttgt tgttgttgtt gttgttttt tttttttttt     3840
ggtgacagag tttctctgtg tagctttctc ttgctatctt ggactttgct ctcctgacca    3900
ggcttgtagg cttgtatttt tcaaaaccta ttttaataag ggttcttcaa tgcttcaacc    3960
tgccttctag cccactgacc aaagggaggg gaggaaaatg gctaatagga caagggaatt    4020
gtggacctgt ttagaagtag tttttcgagg gtgattccag tcttcgttgt cagcagtcca    4080
gtccactagc aaaacaccaa acacaaatca gcagcagcag ttccatctag aagaaacctc    4140
aaggcttccc tctactcagt gcacagaagt ggcaagaagc agccagagca ccaacagaag    4200
ttctttggtg catttctccc acaatgtcac aataagcaaa gatcagagat gaaagcaagg    4260
tgagtgaata caagagtgtc atcttcaaag accagcatta gggaaaccca acaaagacca    4320
gcaaggaaac caatgctgga gcaaggtcca ctgtctgttg ggttacactt atactctttc    4380
taaacatcac atgtcctccc aagcgtctac tacagcaaaa cattacatgc cctttcacca    4440
ggcagcttcc agaaaaacac ctcctgtctg ttctcagcag aacatcctct cataagacag    4500
```

```
cgtcagaaaa acatcacatg acacaactaa gtctccaatg aaaccagata ttcccacttc    4560
aaggctggtc tcgaactcac agagatccac ctgcctctgc ttcccaagag ctaggattaa    4620
agatgtgtgt gcgtcaccat ccagcaacct tgaagtcctg atcctcctgc ttccacctcc    4680
tgagagagag attacagaga gagagaggcg ggggagaggg agagggaaag agggagagag    4740
ggagagagag agagagggag agagagagag agggagaggg agagagggag agggaggaga    4800
gggaggagag ggaggaggga gagagagaga gagagagaga gagagagaga gagagagaga    4860
actcttagtt ggggttgcct tacagtttca gaggtttatc atcttggcag gaagcatgta    4920
gtcatggtgc tggagaggtg ctgagagttc tacattttga tctgtaggca gcaggagact    4980
gtgtcacact gagtaaaact tgagcatttt tgaaacctca aagcctgcct ccatagtgac    5040
acacttcctc caacaaggcc acaccttctt caataaaggt cacatctcct aatagtgcca    5100
tttcctgtag gccaaggatt cacatatatg agtctagggg gaccattcct attcaaacca    5160
ccatggatat gttcttcctt ggaaacagtt atatgcatgt ctagagctgt tattagttat    5220
agaaacagag aaaatactaa atcgatgtat ttaccagata cagagtgggg aaacttagga    5280
aggaaggcca tagccagtaa ggtgagtgaa ttctgctacc tactcagaca ctatgtggct    5340
gcattcttaa ctttcagatt gatagacatg aatctaaaag cctaaaagcc atttcaaaag    5400
ttttatctga aactcaaaag ggcattaggt cagatatagg aatgagaaat aaatggatat    5460
taagggtaac taaaaatagg agctggaggg gtctggaact gtctctaaca ctgttgcctg    5520 tctgggacc ctttcccata actggactgc ctcatctagc ctcaatagga gaagatgcgc    5580
ctagtcttac tgaacttaat atgccaaggc tggttgatat ccatgggagg cctgcccctt    5640
cctgaaaaga aggggggag gactggtgag ggtgggaaga ttgggaaggg aagagggagg    5700
agaaactgtg gttggaatgt aaagtaaatt aattaatttt aaaaatagag gctggaaaaa    5760
tggctcagca gctaatgaca gtggacccag atttgggtat attcccagca tccatttggt    5820
ggataacaac ggtctgtaac tccagaagct tggatgccct ctctgtcctt tgctggcacc    5880
agccacgcac gcacatacag tagacatatg caggcaaaac agacataact ataaaaggta    5940
aataatagca ccattttaaa agaaagggca ctacaaatag ctaaagaaaa aaaaatagct    6000
aaagaatttt tgctttgttt tgtttttgaa gacagggttt ctctgtgtat ctctggctgt    6060
cttggaactg gccctataga ccaggctaga aagactactg ctcagagatc tgcctgcctc    6120
tgcttcctaa gcactaggat taaaggtaag ggccaccatg cctagcagct caagatgatg    6180
aaactcaaat aaatcatata ttcatttaca accctcaaca cagcatagct tggttgggtc    6240
tttttctgag tgtttccatt tacagtgtca cacacacaca caaatttaac tgtgtattct    6300
gcatgtgaga gaaaatatga catgtgtctt cctgagtctg actcatccag tctatttcat    6360
tcttttcatc aacttttctt gcaaatgtca aaaattcacc ttttttcccc tagctcaata    6420
aattttttgc cgtttattgt tgtgaggtgg ttaccagaga agactgctca gacaagggat    6480
gaagcctatt gcaatggttt gtctatgctc agcccaggta gtggccttat tagaagttgt    6540
gatcctgttc gagtaggtgt ggcctcattg gagtcagcat ggcactgtga gtgtgggctt    6600
taagaccctc atcctagctg cctggaaacc agtatcctgc tagcagcctt cagatgaaca    6660
tgtagaactc tcagcttctc ctgcaccata gacactgcca tgctcccacc ttgatgacaa    6720
tgaactgaac ctctgaacct gtaagccagc cccaattaaa tgttgtcctt atgagagttg    6780
tcttggtcat ggcgtctatt cacagcagta aaacccctaac taatacacct atataaagtc    6840
tttactagct gaccagtgac cccagtatag tcccgaccct gttttgggggt gagcttttaa    6900
```

```
gcacaaaaac catatcctgg gttgacacac ttctgttaac aagaagagtt aaccagaagc    6960
aggactacag aagccaaaaa gcaaggtgag aacatttaga gtcattctca tgactatgga    7020
cttcgatgga tcaggtcttt gttttacttt tggcaggtgg tgctatgtgc taaatttcat    7080
agcctgacta gtatttccac cacggagtca attgtgttaa gttctcaggg cctactaaga    7140
tctagggccc tgttagctaa atatgcctgt gtccctcctt gccccaggg attcttggct     7200
gataatggtc cttaaaagca tcagaagcca ggaccagctg tggggaggca gatcaacttt    7260
acttaatgtg acacaaggtt tatataatct ggggaatgtg agcagggtca gattagctga    7320
aggcttaaga taccaaatgc ctcttttttt tttttttttt ttttttgag acaggatatc     7380
tcattactca aagctcacca attaggcaag gttggctggc cagcaagccc cagtactttc    7440
cagcagcact gggactataa gtgtgtgcca ccaagtctgg aatttttttt taataaaaaa    7500
atatgggtct caaatccaac tcagatttga gacctgtttg ccaggcaagc actttattgg    7560
ccaaatcatc tcctcagttc ctaaacagaa ctttttttt ttactcattc ccgtgtactt     7620
taatattgtt acctcaaagg atctagaatg gaaaatggca aacctctggg catgtctatg    7680
acaatctgca gattaggtga gcagagacca gaagacatgc ctaatgtgtg ggaggcactg    7740
ttccctggac tgagaaccta atctggataa aaagaagaaa gaaaattgaa caccagcatc    7800
caactctttt gtctccctaa ttgcataaac aatgttgcca actacctcct acatctccca    7860
ctctgcttct caccagggtg gactcgatca gcttgaacat aaaataacag caaggatttt    7920
ttttctctcc taacttaatt cttctcaggt gcttgtttac actgatgaga aaagcaccc     7980
atgtgggtca gtgagatagc tcggcaagga aaggtgcttg tatttcaagc cacatgacct    8040
gaatttgatt tgattctggg atttacatgg tagagagatt cacccttctcc ttaaattgtc   8100
ctctggcttc tacacgttttt ccacacatgc aagctctctc acacatacac atagttacac   8160
acccatacca ggcacatata cacacaagat aaataataa ataatgttat aaaaatgttt     8220
aaagaaagaa ggaatggaga tttaattagg gagaggataa attaatacag aagaaagagg    8280
gtaaaataac cactaaggtg tctgaaaaat cttaagaaat catttattac caatataccct   8340
aaaattacat gtaagcctgc atatacatat atagtttaaa tgatatttgc ccatccaggg    8400
tgacaatgtc ttttccctga agagtcataa acaatgcccc aacaccaggc ataaaaccc     8460
ttttttgttt gtcaagattg tccaagagtc tcccaaaaca tttcaggcta tttctgtgcc    8520
tttggttgcc tcccagaagt tgaagataag tctccattgc taaagataac ctaggtgtct    8580
ttaatcccat cacttggaag ggagaggagg ggggatctct gagttcgagg tctgcttggt    8640
gtataaagca agttccagga cagttgggc taccctgtct tggggtggtg tcggggacgg     8700
gactacacca tatgcttcag acatctgacc cagctgatct gaactctttg tgatctgaaa    8760
gcctccttcc tgaggacaag cttttcatgat actagaatgt gccatgcacg cacgcttcca   8820
agggaaggaa gtgagcaata attctaccca gctgtgatgc ctgtagaggg acattgtaca    8880
acaaccctaa ggatgcagta gtggaatgaa tagttagtgg taatcaggag ctttctgtag    8940
gcttatatat atattttaa aaatctattt ttaataaggg ttctttaatg ctttagcctc     9000
ccttctagcc caccacccat cagaagtagt ggaaaggaaa ggttcatggg gcaaaggagg    9060
atgcgctctt gtttagaaac agttctttgg agcaaatcca atctgctttg tcagcaggtc    9120
actggatcca ctcacaaaca tcagtctctt tttattttt ttttaagaa ttattatcgc      9180
ttctcggtct tttggctaag atcaagtgaa gaattatttta ttatttaat gtttatttat   9240
ttattttatg tacactgtag ctatcttcag acataccaga agagggcatc agatcgcatt    9300
```

```
acagatggtt gtgagccacc atgtggttgc tggaaattga actcaggacc tctggaagag    9360
cagtcagtgc tcttaaccac tgagccatct ctccagcccc aacaccatta gagtatcagc    9420
gatggcagtt cgatccagaa gaaatcataa gactctgcca acctgcctca gtccttggaa    9480
gtggcaagaa gaaaaccac ctatgaagtc acatcaaatg atgaccagca atggatggca     9540
aggtgagcca ataccataca gcattgtcca ctgtctgcta ggttatattt ataccctttc    9600
taaacatcac acgttctctc aagcatcggc tctagcaaaa catcacatac ctcttttcca    9660
ggctgctttc atagaaacac cacttcagct ttctagacag attatattct tactcatcaa    9720
aagagaagtc atgcctggca ctggaatccc agcccactag ccagggctaa tgaactcatg    9780
gatcttggag gaaaacctac aaccaccact ttactaaacc agcataatcc ataactacac    9840
tctaaatatg tttcctatgc ctgtaggtaa atgtagttct cactcttcaa gcaggaaatt    9900
tctccttgcc tcatacgaag accattacag aaaaccagaa ctgatataac cctgttttcg    9960
agacagggtt tctctgtgta gaccaggctg gcctagaact cagaaatctg tctgcctctg    10020
cctcccgagt gctgggatta aaagcatgcg ccaccacccc tggctggaga gatcacttta    10080
gaagaggcag attgtaagag ccagaggaac ccgaagctag ctgtgagatt tcacctccta    10140
gaaatgacaa ccaaagtgtg gacactttgc cccttcttag aattggaaac aatcacccat    10200
ggaaggagtt acagagacaa agtttggagc tgagacaaaa ggatggacca tctagagact    10260
gccatatcca gtgatccatc ccataattag cctccaaacg atgacaccat tgcatacact    10320
agcaagcgtt tgctgaaagg accctaatat agctgtctct tgtgagacta ggccggggcc    10380
tagcaaacac ataagtggat gctcacagtc aactattgga tggatcacag gcccccaat    10440 ggaggagcta gagagatctg caaccctgta ggtgcaacaa cattatgaac taaccagtac    10500
cccggagctc tcgactctag ctgcatatgt atcaaaagat ggcctagtcg gccatcactg    10560
gaaagagagg cccattggac acgcaaactt tatatgcccc agtacagggg aacgccaggg    10620
ccaaaaagtg ggaatgggtg ggtaggggag tgggggagg gtatggggga cttttgggat     10680
agcattggaa atgtaattga ggaaaatacg taatgaaaag aatatttaaa aaaaaaaag     10740 aaatgacaac aaagcctcac ccactaagtt tcatcaacat ggctatctaa acaagacctg    10800
aattagaaca ggaacagata ttattaacag gaagaggaaa tctcatccac cctcaaccct    10860
tgacaaagag ctatcggaag ctagcaagag aaatagtcat tcccaaggaa gagcacccga    10920
actggatatc caatgtcaag gtcagccttg acataatgta catacatatg gattatagag    10980
actgagcagg taggtttaca tgttttggaa gctatacaca tacacatata catcacata    11040 ctaatttaag aaatagaggt catgattttg agaaagagaa aatgggggc tacataggga     11100 gagttggagg aagaaaagca gggatgctat gattttatta taatttaaaa ttatatatta    11160
tatatagtta tatcttaatt aaaattataa tatataaata aatgaagggg gacaggagag    11220
atggctcagt gcttaagtgc atgtattact tttgcagagg actggagaac agctctgagt    11280
cctcatgttg ggtacctcac aagtgcctat aactctagtt ctaggacat gtactgtgtt     11340 tagtctcagc aggcacctac actcatgtgc acacacccac aaacagacat actctcacac    11400
gtgtaacgtt ttaatatttg ggaggaacaa aaggaaacaa agaaaagtaa cgaatgcagt    11460
ccttctcgat gaacacctgt ggagggccca gatcttggct gttgagaaca gcaataaaca    11520
cagatgtgca tgtatctctg tggtatgtaa acatacagtc ctttgggcat ataccaggaa    11580
gtggtggggc tgaatcatat gttagttagc tctattttta gctttttgag gaacttccac    11640
cctggtttcc attgtggctg aactaattta catttctggt accagtgtct aagatttgcc    11700
```

```
attccccatg tctttgtcaa tatttattgt cattgttttc aacaacaatt tccaaaagtt  11760
tgctgagtac tgttgttact tcaaaaattg tgattctcag tgagtccag  agaggactgg  11820 aaatataggt ctgtaaataa tatttaaatt taggcaactc ttttcatagc ctattatttc  11880
aaaataattt aatagttctg gtgatatgac agcttgaaat actgtcaaag accctttgag  11940
acatttgcag agcaagtgat aagaaataag aacaaaacaa ttttgtacaa tgcaagacaa  12000
aaactcctcc tcctcctcct ccttctttct tatttttttcc tcttcttctg tagtttctcc  12060
tcctcctcct cctcctcctc ctcctcctgg tttttcaaga cagggtttct ctgtgtagcc  12120
ctggctgtcc tggtactcac tttgtagacc aggctggcct cgaactcaga atcccctg    12180 tctctgcctc ccaaatgctg ggattaaagg cgtgtgccac caccatccgg cttctttca   12240 attcttttt  tttttttaa  agattattt  atttattata tgtaagtaca ctgtagctgt  12300
cctcagacac tccagaagag tggcatcaga tttcgttacg gatggttgtg agccaccatg  12360
tggttgctgg gatttgaact cgggaccttt ggaagagcag tcactgctct taaccactga  12420
gccatctcgc cagctccctc tttcaattct ttagggtaca aattatcctt gcttcatttg  12480
tttctgcaat atcaagcact actgcatgat gtacatctgc ggtggtacca taacttcgta  12540
tagcatacat tatacgaagt tatgaattcg tcgccaccgc gagaattgat agttttcagg  12600
gttttaaatg aattggggca taagttaaga aggcaaagtc tctcttacaa aattgaggaa  12660
gtcaggattc agatttctat ttttaatcgt tatctgattg gatgcctttg acttactgac  12720
tttcctaagt aagttctgcc aattttcaat gttctcatag gaaaaatttc gttgtctaga  12780
tcaacttgtg gcgccatctt ctggggcctt aagaagactc tcaagattta aaactgtatt  12840
ggttttttta aagtcttcct agttttttgga agttccttag acgcatgcgc ggcctagcca  12900
ggaagaaact acaattccca gaaagcattg ctatagtgga tgggtggggg actcccgttg  12960
tcatggggga aatgattctc gcgagaaagt gagcctgtgg cggctgtgcg tcctgggtgg  13020
agggggtggg ggggaggagg cggggagagt aaggaggaag aggaggaggt gcagtcccac  13080
aatacccggc ggagggaggg tgggtggttg gcgtctggtc tgtgcggagc tcgggtcccc  13140
ggcggactca gcttcctctg tctctttaat gcgagaggaa gcgatgcgga ggggtggaaa  13200
atggcagagc tgcagatgtt actagaggag gagatcccgt ctggcaagag ggcgctgata  13260
gagagttacc agaacctgac ccgggtggcg gactactgtg aaaacaacta tatacaggtg  13320
aggagcttga gcggccggcg ggggcggctg ggacgacagg caggctgggc gccgtgggga  13380
ctgccctact ccgccaccct ccgccccagc ccgagcggcg gccgccgcgg cgatacagga  13440
agtggccgcc ttgagaaaat gggtgaggag cagggccgcc gcgggcgccg ctgacccgat  13500
gccgctcccc gcgtacgccg gcttaagtgt acacgcgtac tagtctagcg aagttcctat  13560
actttctaga gaataggaac ttcccgcgga taacttcgta tagcatacat tatacgaagt  13620
tatgtcagct tctgatggaa ttagaacttg gcaaaacaat actgagaatg aagtgtatgt  13680
ggaacagagg ctgctgatct cgttcttcag gctatgaaac tgacacattt ggaaaccaca  13740
gtacttagaa ccacaaagtg ggaatcaaga gaaaacaat  gatcccacga gagatctata  13800
gatctataga tcatgagtgg gaggaatgag ctggcccta  atttggtttt gcttgtttaa  13860
attatgatat ccaactatga aacattatca taaagcaata gtaaagagcc ttcagtaaag  13920
agcaggcatt tatctaatcc caccccccacc cccaccccg  tagctccaat ccttccattc  13980
aaaatgtagg tactctgttc tcacccttct taacaaagta tgcaggaaa  aacttccatt  14040 ttagtggaca tctttattgt ttaatagatc atcaatttct gcagacttac agcggatcga  14100
```

```
tccccctcaga agaactcgtc aagaaggcga tagaaggcga tgcgctgcga atcgggagcg    14160
gcgataccgt aaagcacgag gaagcggtca gcccattcgc cgccaagctc ttcagcaata    14220
tcacgggtag ccaacgctat gtcctgatag cggtccgcca cacccagccg gccacagtcg    14280
atgaatccaa aaaagcggcc attttccacc atgatattcg gcaagcaggc atcgccatgg    14340
gtcacgacga gatcatcgcc gtcgggcatg cgcgccttga gcctggcgaa cagttcggct    14400
ggcgcgagcc cctgatgctc ttcgtccaga tcatcctgat cgacaagacc ggcttccatc    14460
cgagtacgtg ctcgctcgat gcgatgtttc gcttggtggt cgaatgggca ggtagccgga    14520
tcaagcgtat gcagccgccg cattgcatca gccatgatgg atactttctc ggcaggagca    14580
aggtgagatg acaggagatc ctgccccggc acttcgccca atagcagcca gtcccttccc    14640
gcttcagtga caacgtcgag cacagctgcg caaggaacgc ccgtcgtggc cagccacgat    14700
agccgcgctg cctcgtcctg cagttcattc agggcaccgg acaggtcggt cttgacaaaa    14760
agaaccgggc gcccctgcgc tgacagccgg aacacggcgg catcagagca gccgattgtc    14820
tgttgtgccc agtcatagcc gaatagcctc tccacccaag cggccggaga acctgcgtgc    14880
aatccatctt gttcaatggc cgatcccata ttggctgcag gtcgaaaggc ccggagatga    14940
ggaagaggag aacagcgcgg cagacgtgcg cttttgaagc gtgcagaatg ccgggctccg    15000
gaggaccttc gcgcccgccc cgcccctgag cccgccctg agcccgcccc cggacccacc    15060
ccttcccagc ctctgagccc agaaagcgaa ggagcaaagc tgctattggc cgctgcccca    15120
aaggcctacc cgcttccatt gctcagcggt gctgtccatc tgcacgagac tagtgagacg    15180
tgctacttcc atttgtcacg tcctgcacga cgcgagctgc ggggcggggg ggaacttcct    15240
gactagggga ggagtagaag gtggcgcgaa ggggccacca agaacggag ccggttggcg    15300 ctaccggtgg atgtggaatg tgtgcgaggc cagaggccac ttgtgtagcg ccaagtgcca    15360
gcggggctgc taaagcgcat gctccagact gccttgggaa aagcgcctcc cctacccggt    15420
agaatgaagt tcctatactt tctagagaat aggaacttcg ttcgaacata acttcgtata    15480
gcatacatta tacgaagtta tggtacctgc agaattcatg acataagctt ggatccgttc    15540
ttcggacgcc tcgtcaacac cgtacgcagc ctgcccgggg ccgcctgtgc tccccacagc    15600
ctgcccgggc gttgctccct aaagcctacc ccggccgagc tctgcttctc gccgtctgcc    15660
cggcccagct gtgctcccca ccacctgccc tggctgaggt ctgcgcctaa ccccgccgc    15720 tttccccgcc agggatctgt ttcctgcagc cttcccaggc cgggacgtgc tcccggcagt    15780 cttttccttcc cggtctccgc tcactgcagg ccgctcttct tagtcgggct gtattcagct    15840
ttgcctcttt tggctgcggt tggttcctaa gacccccac agccttccct ggctggggtc    15900
ggtcctggct gaggtccccc tggaaatccc gcagcctccc ttggtctcct tggagctcag    15960
acttcgctgt cgcccccatg tccggtgtga tgagcctagg actgggacag ctgcgagagg    16020
aatgggcagg gaaggaaaag tggggtgtgt gtgtgtcgtt ggagggtggg gtgagggtga    16080
ttatgtcagt tcatcctaga gggtgtgcct tttatttatt taaaaaaatt gtcacgagtc    16140
acatttgtac agacctccta atcgagtgcg gagagtgact gctgagggtg tgataaaatc    16200
catattaaaa ttcttttaat tgaaggaaaa atgcgtgctt ggcgattttc aagttgggct    16260
tttcctcttc cacctcctca tatttacttc cgctttagca taatgtatac tcgttattat    16320
aaagcacgaa tgattcatag ggaaattcag tgggaaatct gttaaatact ttcttcctc    16380 taaatgttct tggactgttg gccttgaacg cagtagtgtt atcgtggttg cttatgttct    16440
gagatttctt tctatactga gttaatacat agaagaatat gaataaagta gattagcaaa    16500
```

```
cattatgtag tctttaagtc ataacataga attgctcctt aatttatcag gaaattcttg    16560 gcactttta c tatgccatgc ttgcttgtgt ttatcagcga ttgtaagtga attgtatgta   16620
gtagtttgac ttgtccctat ggttgagtaa aaattaacag ttttcactag aagcaaatac   16680
agtagtggaa ttctttgtat cagataatga gaatagaaat tcatttcttg ttgataaggc   16740
aaaaccagaa cagtctttga aaaataagga atattgtact ttggacctgc agtatttctt   16800
aaagtgcctt tcatgtgatt atcattttca gagcggcta atttctgttc tagcagattc    16860
ctgtagattt tgttttcaga aggagatgct gtcttgagac ttgtctgagt atttgtcatt   16920
ttccatatta gtaacattct atctggagtg gtactccaag gagtttgtct tcctactctc   16980
gtttccagcc tttgactttg gtaatctact cataaacttg ttgaatgctt cctgtgtctt   17040
ctgtataact tggttttgaa aactatatgg ctgttttaaaa acacatttta agcagcagaa   17100
gggctgcctt aaccactgtt aagagcagtt ggtgcttttg cagaggactc gggttcagtt   17160
cccagcgccc tcatagtggt tcacagccat ccttatccta gggggtccgt gtcctcttct   17220
gacacctgtg ggcaccaaac acacattcag tacacataca cacatacaca catgcataca   17280
cataggtacg atgagtgagt ttaaacctat ttcaaaatca tacagaaatg tggatatagt   17340
gtggaaatag aaaggtgatc ttgtatttta tagatactaa aaaatgtaca tcttttattt   17400
attttagtat gaaaaacctt gggtttgttg catctttggt tcccagcact tgtatgaggc   17460
aggttacaac tacctctaac tccagcttca ggggatctaa caccctattc tggatgtatg   17520
gggtcctgca ctcaggagtg catggacaca tccacaaaca attaaaaagt ggatagacac   17580
acaatttaaa gcaacccact ttaattggta atagtgctga ttaggataag tagttgtgct   17640
atttgttttt ctttgtgtgt aaagtttgcg tttgttttca gacacaatct cattctagac   17700
caggctgctg actttctatc ctcttgtcag cttccaggtg ccatgcagct gccatacccca   17760 gctgaggtgg gaaagggttt tatgggggg tgagatgggg gacagggtct tattatgcca    17820
tcttggctgg tctggagctt attacataga ctaggctggg tgacagagat ctctcttctc   17880
tgtctcatct actgagatta acatgaatc accatgcctg aggagaaaaa ttgtcatact    17940
tactgtgaga cgattgctgt gtgttttacc atgataatta ttttgttgtt ttcttatgtt   18000
tggaaaattc agccctgttt gctgagaagt tattttggct agttcttggg ctttgggccc   18060
tgctgagttt agtacttaaa ctgagttatt aaatgcagat cttattgaaa gcttcttcag   18120
ctccttaaaa agaatggagt tttaaagtta tggggtgagg ctggagaaac agccacacca   18180
gaagagggtc ccattacaga tggttgtgag ccaccatgtg gttgctgggt attgaactca   18240
ggaactctgg aagagcagtc tgtgctctta accgctgagc catcttgcca gccctatttt   18300
tattgtttta aatcatatgt atatatgcgt gcttctgctg gcatatgca catgaatgca    18360 ggtgcctaca caagccagtg gcatcagatc tccctggagc tggagttaca gttggttatg   18420
agcctcctga tatgggggct gggaatccaa tttgtgtcct ttggaagagc agtctgcaca   18480
cttaactgct tagctcagag aaaagccagc tctaaagtac aaacctacct gctcttctgt   18540
ttgcagctta gaacttggaa tgtatttttca aaagaatggt tgctggagct gtcaggttcc   18600
catactggtc caacaggtct acttactcta agaacattcc tgaactagtc tgaggtctag   18660
attctcatga aaactgtgtg atatacaaac tactctaccc acttgtggag tctgtcacac   18720
ctaaggaatc tgccaatcac taaatgtata gccaagcaaa atttatttaa cttctcctgtg   18780 tctaaatttt cttacttata tgagggcact ccctatgaca gccagcatat aaggattaaa   18840
tacaaagtag aaagattaca gcacaataga aactcaataa acagactcaa ttaagactgg   18900
```

```
ttctccatat ctgtgtgatt cgacaatcat gtattaaacc tactgctgac ccaatgtgct   18960
gcgcagattt tattgtcact cttccctaaa aactattgtg tgtgaaaact taagaattta   19020
gggtcagcat ctatagcaca gagggcagga atagtgagca gttgggtaga tggattcagc   19080
actaaggaac aaagatgggc ttctctctca gacttctgta tagctgggtt attgctggag   19140
ggtctgtcta ttttagggag gggttttctg ctcagtcagt aggattttct tttcaaagta   19200
catcattgaa aggataatag ggaaaataac aatgcacttt gataaagaaa tagttgactt   19260
gataatttta acagtatacg tatatagtgg actttggggt tgcttttag tggtactact    19320 ctgttgaccc aaataagttt acccttggct ctgttgattt ttctccactt ataaaaaatt   19380
ttagaattaa ttgcaagtgt atccatgttc ataacaagaa tctgaaagca aatagaacat   19440
cttaagaaag gtaatgtttt tgtcgctaag tgatgtgatg gcctggtgtg atgactgttg   19500
cctgtaatcc tgtggtagga ggatcactag gagttcatgg cagcctgttg aggtacagag   19560
tgatccaagt tagcctagtc tagaatgaga ctctggctca aacaaatgac agaagaatta   19620
gctgtaaaac taagttcctt cttttcccca ctttatctct cccttcttcc tctctctctc   19680
tctctctctc tctctctctc tctctctctc ctctccctcc ctcccctcct cccttccttc    19740
ctccctctct ccctttcttc cctttttattg tagcccaggc tgatttctaa ctggtaggta   19800
gttgagattg acctagaatt cctttactgc ccctatcttc catattctgt gctatgcagc   19860
tgtgtgtgat tcttcacaac tgtgttatcc tacttgttcc tattcctgcc ccaaactacc   19920
actagttcat cttgggtgtg tgtatttgtg ttgggaggga gagatagaaa gagatggata   19980
gatggattca tgcagatgcc acagtgccca tttggaagtc acacagcctt tgacggtttg   20040
tccattcctt ttactgtggt ctgatgatta ttctgggttt caggttatta ggctttcact   20100
gtccagcagt ttctctgctg aactatattt cagcctccct tcatccccat taattcttct   20160
taagtggctt aaataattcc ttttgtttta tttattatgt ttttgagaca atctcactgt   20220
gtagctcagg ctgacctgaa actcatgggt ggcaatgtct tccctttatc tcccgagtgt   20280
tgggactgta gtgtgaaaca cctcacctgt gggttttttt ttttttttaat ggactataat   20340 gctccagtat gaggagaggc agcactggag aatgtctccc agctgactca ctaagtgagt   20400
cactttaaaa aagcaatctg ttggaattct ggcctgctca acaagaggga aagcatgttt   20460
agtactggaa acctagccaa ctacccagaa ctagtgaagt catggatctt ggaagagaac   20520
ctacaatcaa ccgccacttc taaaccagca taatccttaa ctacatttaa aatttttttt   20580
tcatacagaa tactttgatc tgattatttg ccttcttcca actcctccca ggtttttctt   20640
aactcctgac caatgtgtac atgagagccc aagcaaactt cccgaaagca gcaaccctca   20700
aaagcagaaa gaaacaaaac aaaatgagtg cacataaaaa tggagtccgc acgcctttaa   20760
tcctagcact tgggaggcag aggcaggtgg atttctgagt tcgaggccag cctggtctac   20820
agagtgagtt ccagaacagc cagggctaca cagagaaacc ctgtctcaaa aaccaaaaaa   20880
aaacaaaaag caaaaaacac cccccccca aaaaaaagg agtccatttt ggttttgtgt    20940
tggtcatttc ctcctgcgca tgggcatgt tatacctccc agtggcacct cattgtagga    21000
agctgatttt cttttcccag caggtatcaa ttgcagatag cttcttggtc tagagtggga   21060
ccttctctgt gctgctttc tgcctggttt gaacttgggc aggatttgtg cctgctgtca    21120
cagttgctgt gagttcataa agataactgt cctgttgtct ctggaaaatg gtgtttatgg   21180
cttagagtca tctgccacct ctggcttgaa cgatctttct acctcttcta aatagctgca   21240
ttttgcatag acacatttta aatattgatc tttatgcctc accttcatc atctaacttc    21300
```

```
tttttgcaat ggagggaac cattacagaa aatgataacc cacaaaataa agggttgtag    21360
agcccagtta taaccattac atctacaaca cagctcctgc acctaaggct cggggatcat    21420
tgcgtaagag tgagtagaaa agattgttaa gagccagagc atcttttgat gtgggagtgt    21480
ctcctagaaa tgcacagaagc tacactcatg aggtctcatc agcatagttg catgaacacg    21540
acctgaaaaa ggactatacc agtagacatg ctaatatgag aggggaaaag cttacaaggt    21600
ctctagacaa atagagaagt gtcccttccc actcccctaa ttgcttatca aataccaaaa    21660
ggtcagtcct gagagcatac atacaagtaa catcatttgg actgaacagg ttgttttat     21720 gtgtttagga atacacacac atacacagac atattcaaac aattaaagaa aaagaggcca    21780
tgagtttgaa agagagtgtg gtgtgaatgt acgtgagggg ttggaaggag aaaagacaag    21840
ctggaaatca tataactaat cttttttttt ttttaaagat ttatttatta tatgtaagta    21900
cattgtagct atcttcagac actccagaag agggcatcag atcttgttac agatggttgt    21960
aagccaccat gtggttgctg ggatttgaac ttaggacctt tggaagagca gtcagtgctc    22020
ttaaccactg agccatctct ccagctccat gtaactaatc ttaaaggaa aaaaaggag     22080 caaccatttt tgtgtttggg ccaatcacaa ccatttcttt ggaccagtca cagccttgtc    22140
ccctagcatt aattatagtc tttggggctt ggattttagg ccctctgtaa gtctcaccac    22200
ttagcatcag tcagagtagt acctctactg gggacagcgc tagctctctg accaaggtgg    22260
cagtagttgc aggggcacct agagtccctc agggcatgtg atagcaaaag cctggtacca    22320
gctattccag acagccctgg ctgagctggt tcctttagga gcggcagtct tagtgtgatt    22380
accaggggtt tccagggtaa tccaaacagc tagttctagt gtataggtgc acatctgact    22440
cagaagataa cttttttgtt tgttttgttt tgtcctttgc agacagagct gttcttgaac    22500
ttgctgtgta gctgagggtg atcttgaaaa cgatgtcctc ctgttacatt tcaagtgctc    22560
ggattacagg agagcattta ttaaaatcctg gcttctatta cattttaaaa aacattttgt    22620 attttatgt gtatgcatgt tttgcctgca tctgtgtctg cataccacat gcctgcttga    22680
tgcccagtga tgccagaaaa ggtgccagat cccctggaac tggagttatg aatagttgtg    22740
agccatcatg tgggtgctag actgaatctg ggtcctctgc aagagcaata attgcactta    22800
atttctttcc agttctctac cccacccaca cctggctttt acatcttaag tttgtctatt    22860
ctatatccat tgcattaact gttgagtaga catttgctat agcttcccaa tgatcctttt    22920
gtcatcttca cacatcttcc tttgaccaat tatccctcct gagcttttgt tgcaatactg    22980
tggtactttc aaagtagaaa tctggactga tgcaaggctt aggggttag agcacttgct    23040 gccaagagtg atgacctgaa ttgatctttg ggatccatgt ggtacaagga gagaatttac    23100
tatcaccagt tgttctctga tttcatgtt tacaccatgg gaatgcatgc aaacaagtat     23160
taaaaaaaaa aaagtgagcc tagcatggtg gggcacacca tttattttag cactcaggcg    23220
gtagaagcag ttgggtctct tgagttcaag gttagcctgg tctacacaat gaattccagg    23280
acagccaagg ctatgaagaa aagccctgtc tcaaaaaagc aaaaacacca ctgcctgttt    23340
aaaatactct actgatttac tattaatata cttgtagttt gaatgatggt acaccttaaa    23400
gactcatgta actgaggctt tttgggggt gcttgtcgtg gggattctgt cctcagaaat     23460
ggggtagtac ttaaaggtta gagggaatga gtttagcttg tttgcccttt ggccttttgc    23520
catatgagga tatagcaaga gactatcact acacaaaata aatgtccaca actttctttt    23580
tggctctttt ttttttttcc tttgagatag ggttttttctg tgttcttgac tgtcctggaa    23640
cttgctctat agaccaggct ggccttgaac tcacaaagat ctgcctgcct ctgcctcctg    23700
```

```
agtgctgaga ttaaaggcat cagccaccac tgcttgacaa gtatcctaga ttttaaaact   23760
gaaataaggg gctggtgagg tggtagagca cttgctgctt ttccttagga ctcaggttta   23820
ttcctagcac ccacatactg gtttacagca gtaactctag ttccagaaga ttggaacatt   23880
ctcttctagc ctctgcaggc accatacaca tgtagtatac agatatactt gcagtcaaaa   23940 taccettaca cataaattgt aaagtttgtg ttttttaatg tgtgtgtgtg tatgtgtgtg   24000
tatgtatgtg tgtgtgtata tatataaaat cacagcctgt gatattttgt tgtaacagca   24060
cacattaaga tatgtttcag tgaggtctgg aaaggtctgt atgtataggt ggattggcca   24120
tactgacttc ttaactacct ttcagtggct gtgacaaagc actgtgacca agaaggcacc   24180
ttatggaagg aagtgcttat ggtggcttgc agtgtcagag ggtgagtttg tatttatcat   24240
tgtaggaagc atggtaggca gacacgtatg gtgctggagc tgtaggtgag agcctgaacc   24300
tgacttacaa gcaagaggca cacgctcgaa tgctcacacg cacacacaca cacacacaca   24360
cacacacaca cacacacaca catacacaca cacacacaca agggggggggg gagagagaga   24420 gagagaggga ggggcatttg aaacctcaaa gcctgctttt agtgatatac cttctccaac   24480
aaggtcccac ctcttaatct tcccccaaca gtttaaccga ctgtggacca agtattcaag   24540
tacatgggcc tatgggagtc attctcattc agaccatcac attggctttc agtattccta   24600 gttttcttt taaactcact ttaattcctt agtagtatcc tctaatttga tttgtttctt   24660
ttgatggata ttactcaccc atgagggctt tccttgtcta gatggaaaat tgtcatattc   24720
ttccatacat taatacttaa cttaattgtg tatctatttt gcctcccaga gataataatg   24780
actgagacaa agactatata tccttaggaa attttcgtta tggggacaag ggaacatgct   24840
gagtatgcac acacacacct cgcgcacaca cacccacacc cacacgcaca taaccaaaca   24900
ccaaaactaa aaccectcat ttcaaataga taaggaagta gtaagatggg agctagaaaa   24960
ccaggatttg gaagaagggg cttcttcagc tacaggggtt tggaaatcaa tctttctttt   25020 cttctttct ttctttcttt cttctttct ttctttcttt cttctttct ttctttcttt   25080 cttctttct tgggtgggg cagactagac atggtttctc tgtatagccc tggctgtcct   25140
ggaactctct gtgtagacca agctggcctc caactcagaa atccctctgc ctctacctcc   25200
caagcgctgg gatcaaaggt gtgcgccacc actgcccagc tgaagatagc ttctttatat   25260
tatatctaaa tattttatg tgttctgaga gtgtgcagtg gctgcagagg ccagagaggg   25320
caccagattc tgtggagcta ggagttatag gtggttgtga gctgcctaat gtgggtgctg   25380
ggaacagatc ctgggtcctt tggaagagca gtagtgccct tagccacagt catctctgca   25440
gcctctgtga aaggagcatt catgcagatt tggaggactt gctagttgcc tgcttttttg   25500
aagatctaag gaaccatgt ggaactgtta ggaaatgaga aaaaaaatt tttttaatct   25560 tattttattt tttagggtaa agttctttat ggcaagtatg gaggcattct ggggccagat   25620
ttattttaac ataacagtat tacaataaaa tttagtcaac aaacatgcga caaaaggagg   25680
tgtgggaagc aaatgggaac agagagaggg acagaatctt cagtgaagat ctgctgaact   25740
ctttacaatt tcaaacctgt ttcccagaga agtcatatga aaatggtgat tccaggatgt   25800
tcacctggga ctcagccatg aaagtcagta aagtcacaaa aggagtgaac acagcctaga   25860
aatccagatc agtttaaaag ttgtatcggt ggatttatcg gagacaagta aatcagaaa   25920 ataaccagga gccaatttgt gactcatagg aagaaagctg gagttttctt aggtttgatg   25980
gggtgagttt attatgggag tatttgattc acttttcctt tttaaggaca ggatctcact   26040
gtgtagtcct ccgtgaccag agactcacag agatctgcaa gtctctgcct cctgagtgct   26100
```

```
gggattaaag gtgtgcctcg gttgtgctgg gcttgactta cttcttagag aattagactg   26160
ctcagtggga aacagactga aggagggagg gcagagtcag ccagtggggt gagtatgaca   26220
ctgaggagtt agagcaggta cgtgtgttga agacacagtg ggaagtgtat gttggattgc   26280
acgtggtgta agagaacggt gtaagtactc ctccattccc tttagcatgc tagcagatgg   26340
ctgggccctg ggggtaggtt ttagggagaa gaatatgatg gtgtctgttc agttatgtaa   26400
agtatgagat atcaattaag catatggtcc agttggccat gctggagctc aggaaaaact   26460
atataagata tgaaaaatac atacttagta acactaccaa ggtctcattg gaaaaatttt   26520
aaatattgaa gaggtttaaa gctcaagtga taaatgtgtt ttcccaaaat ctttttttt   26580 ttttgacttc agagttcaaa ttttatttat tgatgataag tcttgctggt tattttcctt   26640
aaatgacaaa ctgtgtactc atcagcagga gactgccagt actcaagcct gaaagtagta   26700
gttggtgtgt cagtttaaaa aaaaaaatg gtctcctttt acaagtaagt tgtactgcgg   26760
cttttttcta aagacaacca tcatatgtag tatgtaacaa aggcaatttt caggtattta   26820
agttctcttg tggggagaag ttgaaatagg gtcttatcct gtatctccag ctggcttgga   26880
atttgctgta tagacgaggc agaactcata gaaatccatc tgcctcagcc ccccaagtgc   26940
tggattggaa agctgaaggc cagcttgagc tacatagggga gagcgagtct ggaaaagttt   27000
gaccttgatc ttgtgaacaa tccctcccta aagtagacca tactaaagag cctttgtgat   27060
ttagtaagct tcataacttc tgctgtagta atgggagcct gcattttaca aatcatagta   27120
tacttattaa tatttatat ttattgagtg tctctgacta aagtaaattg gtaatctcat   27180
aaaaatttag ttacttatgc atgaatcttc ttggcataat atctaatata tattatttta   27240
ataattttat atagaggggc tagagatggt taatagcata catagcactt ggtagtgttt   27300
tggagaacct gagtttggtc cctagcaccc acactgagtg gttcataatc acctatactt   27360
tcatataggt tccaatcacc tataatcttc agctccaggg aatccaacat tattcttttg   27420
gcttctgagg gcatctgcat cacatgcaca ttctcacaca catacatatg attaaagaaa   27480
agtgaggagt tggagaggtg gctcagtggt taagagtact agatgctctt ccaaaacacc   27540
agagttcata gaccagcacc catgcccatg accaccagct gcctgtaacc agcacccatg   27600
accatgacca ccagagttca tagaccagca cccatgccca tgcccaccag ctgcctgtaa   27660
ccagcaccca tgcccatgac caccagctgc ctgtaaccag cacccatgcc catgaccacc   27720
agagttcata gaccagcacc catgcccatg accaccagct gcctgtaacc agcacccatg   27780
cccatgactc acaactgcct gcagttctag ttccaagatc tgacaccttc ctctggcctt   27840
ggtggatatt ccctcacatg tagcagacat tcaaattaac acacagaaat aaaaataatc   27900
ttaaaaaaat ctttgactag gaatttagat tcagagcctt tctattatgt atatttaatt   27960
gctgatgatc ctgtattcgc tttctagagt ctgtgtctat caataattac ttacatggtt   28020
gtttttaggc ggttgttcaa aacgattttt aggaaagagt gaaaaatagc tttttactct   28080
aaaatgatga tatagtcatt ttaaatttga aaatgtttca cattgggttt aaagaaatct   28140
tatgaacact cctttattct tgtagaagat ctgaatttaa gcatctactt ggtggctcat   28200
agagaatcta atgaccttct ggcctccact ggcacgaggt gtgcatatgg cacataaaca   28260
tgtaggcaaa agactcataa gcataattta aatccccct cccatcccca gaaacctaaa   28320
tctgttgttg gaggccagtg agataaaagt atttgctctg aagcccaaat tctgtccata   28380
gagcccatgt agtaaaggag acagccagta ctctcagcct ctgactgcca cacattttaa   28440
cacccactga taaatgttta aaaagaagcc cattgttcat gcctatggta cttatagaac   28500
```

```
ttccaattta gaatatgtgt gtgtgtgtgt gtgtgtgtgt gtgtgtgtac atgatgccat    28560
gtgcaggcca ggctgctccc tgtttacttg acatctttct ttgggtggtg gttgctgctg    28620
tagccatact tcttgctgca gtttacagca tagtgtgcag gtcagcactt gctgtagatc    28680
atcatgtcct aggtttatgt acttcagggc aagctgtcac agtgagggcc agttgataac    28740
actgtgcatg cagggtaaac tcttaatgtt ggacacagtg ctgtcatact ccagctgttc    28800
gaccatgagt atggagtgtg ataacattct tgataatgtt actgggcttg atctcaagag    28860
ctatatggtc ttgtgagtca aggtcttctc aaagactagt atcttgtctg ttggtgagct    28920
gccctgttga agaagaaaaa actgggctca gttcttgatc ctgttgtctt aacgtctcaa    28980
atgctaggat tacaggtctg taacaccatg tctgactctt cattttctta tatacattta    29040
ttacttttgt gaaaggcttt gaatgagtac attttttctgt caaactatgt cattttaaaa    29100
aggtttgata aatctgtttt attttctaac tccaggttcc attaaagttt ctaatattta    29160
aatttactaa attgtgagaa tttatcttct tattttgtcc tatgatgttt aattttttt    29220 ttttttttt tgagtattaa tagagtacca aaaatcccag aggaaaccgg caaacttta    29280 tatgatctca agttagaatc acagagtttc aaaataaatg tttagtaaaa tgagatgtat    29340
ctaacaatct gtaatgtgct tcaccgcagg aatatattcg ttacttgtta agttatccag    29400
caacctaaaa agtgcattca tcttctgtgt gaggaggcag gagggagaga gagagaatat    29460
gaacgtgttg tttgtgagtc ctgagcaaat atgtaccatg gtgtgcatgc caaggtctta    29520
ggacaacttt tgagagtcag ttctttcctt ctaacatgtg ggtcctgcag atcaaacata    29580
ggtcattagc cccttacac actgagccat tttactgacc ttttagttt taaagatttt    29640 attttatttt tacttttac tctgattta tgttgttcag gctggtcttg aactcctgat    29700
tcatttgcct ccaccttcca agtgcccaat cacagatgtg tgttgggcgc cagcatgccc    29760
agcttgttta gttggttttt ttggagacaa ggtctcatta gttgcacagg ttagccttga    29820
aggcctagtc tcaagtaatc ctttatggt aggcttatct gtgggtagaa taaaagttgc    29880
cagtcaccct gtcagcatgt ctagcttagc aactttctgc ctcctattat tcattccagt    29940
ggttttgtct ataagatgta atcactctcc tcaaatcttt tcattagtc aaataagtca    30000 tgaaacataa taaatggtat agagaaaaac acattgacac aacagagttc ttctactcag    30060
cttgatatgt caaagaagac attattaggc ttgagttctg aaaaatgtta atcaggaaag    30120
ctggggttgt gggggtgcag atagtggtat gtatctagac caaagttatg tgaaaacaga    30180
atgattttta acagtttata agcttgggtg ctttagatta cacaaagtag ggcaacagtc    30240
tgtaaagaag tagtaggaat cagattcagc aagaccttat caagtcattg tagtgatttt    30300
agcttttttc aaaccttag gctgatgaaa aggtactgaa agtttttttt ttttttttt    30360 ttttcttcga gacagggttt ctctgtgtaa ccctggctgt cctggaactc actctgtaga    30420
ccaggctggc cttgaactca gaaatctatc tgcctctgcc tcccaagtgc tgggattaaa    30480
ggagtgtgcc acctttgttc agtactgaac gttttaaaca atgagatgac actaatccca    30540
actcttggga agctgatgct gaggccgagg ccattcttga ccacaagaga ccctatctca    30600 aaaagggac gtggggctg gtgaactggc tcaggtgtta aaagtgagtg ctgttcttat    30660
aaaggaccca agtttggttc ccagtgccta tgtcatgtgc ctcacagatg cctgtaaccc    30720
caaatgcagg ggacccagta ccctcttcta tcgtctgtgg gaacctgtag tcacatgcac    30780
atgctaacaa gcatatacac atactttaaa ataagataag ttgggctaga gggttgtttc    30840
agaggtaaag agcattggct attcttcaaa aggacccagg ttcaattccc agtgtgcaca    30900
```

```
tggcatatca caactgtctg taaccttagt tccaggggat ccaacaccat cacacacaca    30960
tacaagcagg cagaactcca atgtacagaa ataaaaaat cataaaaaat aaaaataagt    31020
tgaaacaaca attgcaaatt aaaaataaag gttattttg ccttatgtga tgacacgagg    31080
ctcacaccag taatttcagt actcaggagc cgaggaggca gtattgctac aacttcaagg    31140
ttagttgggg ctaatacttt taagccacag ag                                  31172

<210> SEQ ID NO 15
<211> LENGTH: 25
<212> TYPE: DNA
<213> ORGANISM: Artificial
<220> FEATURE:
<223> OTHER INFORMATION: Primer

<400> SEQUENCE: 15
cgatacagga agtggccgcc ttgag                                          25

<210> SEQ ID NO 16
<211> LENGTH: 25
<212> TYPE: DNA
<213> ORGANISM: Artificial
<220> FEATURE:
<223> OTHER INFORMATION: Primer

<400> SEQUENCE: 16
cgttcttcgg acgcctcgtc aacac                                          25

<210> SEQ ID NO 17
<211> LENGTH: 22
<212> TYPE: DNA
<213> ORGANISM: Artificial
<220> FEATURE:
<223> OTHER INFORMATION: Primer

<400> SEQUENCE: 17
gatgccgctc cccgcagcct gc                                             22

<210> SEQ ID NO 18
<211> LENGTH: 21
<212> TYPE: DNA
<213> ORGANISM: Artificial
<220> FEATURE:
<223> OTHER INFORMATION: Primer

<400> SEQUENCE: 18
cactctccgc actcgattag g                                              21

<210> SEQ ID NO 19
<211> LENGTH: 1449
<212> TYPE: DNA
<213> ORGANISM: Artificial
<220> FEATURE:
<223> OTHER INFORMATION: Abi1/Hssh3bp1 floxed allele after removal of
      neomycin gene

<400> SEQUENCE: 19
tcactgctct taaccactga gccatctcgc cagctccctc tttcaattct ttagggtaca    60
aattatcctt gcttcatttg tttctgcaat atcaagcact actgcatgat gtacatctgc   120
ggtggtacca taacttcgta tagcatacat tatacgaagt tatgaattcg tcgccaccgc   180
gagaattgat agttttcagg gttttaaatg aattggggca taagttaaga aggcaaagtc   240
tctcttacaa aattgaggaa gtcaggattc agatttctat ttttaatcgt tatctgattg   300
gatgcctttg acttactgac tttcctaagt aagttctgcc aatttcaat gttctcatag    360
```

```
gaaaaatttc gttgtctaga tcaacttgtg gcgccatctt ctggggcctt aagaagactc      420
tcaagattta aaactgtatt ggttttttta aagtcttcct agtttttgga agttccttag      480
acgcatgcgc ggcctagcca ggaagaaact acaattccca gaaagcattg ctatagtgga      540
tgggtggggg actcccgttg tcatggggga aatgattctc gcgagaaagt gagcctgtgg      600
cggctgtgcg tcctgggtgg aggggtggg ggggaggagg cggggagagt aaggaggaag       660
aggaggaggt gcagtcccac aatacccggc ggagggaggg tgggtggttg gcgtctggtc      720
tgtgcggagc tcgggtcccc ggcggactca gcttcctctg tctctttaat gcgagaggaa      780
gcgatgcgga ggggtggaaa atggcagagc tgcagatgtt actagaggag gagatcccgt      840
ctggcaagag ggcgctgata gagagttacc agaacctgac ccgggtggcg gactactgtg      900
aaaacaacta tatacaggtg aggagcttga gcggccggcg gggcggctg ggacgacagg       960 caggctgggc gccgtgggga ctgccctact ccgccaccct ccgccccagc ccgagcggcg     1020
gccgccgcgg cgatacagga agtggccgcc ttgagaaaat gggtgaggag cagggccgcc     1080
gcgggcgccg ctgacccgat gccgctcccc gcgtacgccg gcttaagtgt acacgcgtac     1140
tagtctagcg aagttcctat actttctaga gaataggaac ttcgttcgaa cataacttcg     1200
tatagcatac attatacgaa gttatggtac ctgcagaatt catgacataa gcttggatcc     1260
gttcttcgga cgcctcgtca acaccgtacg cagcctgccc ggggccgcct gtgctcccca     1320
cagcctgccc gggcgttgct ccctaaagcc tacccggcc gagctctgct tctcgccgtc      1380
tgcccggccc agctgtgctc cccaccacct gccctggctg aggtctgcgc ctaaacccg      1440 ccgctttcc                                                             1449

<210> SEQ ID NO 20
<211> LENGTH: 354
<212> TYPE: DNA
<213> ORGANISM: Artificial
<220> FEATURE:
<223> OTHER INFORMATION: Abi1/Hssh3bp1 KO allele resulting from Cre
      recombinase-mediated recombination

<400> SEQUENCE: 20
tcactgctct taaccactga gccatctcgc cagctccctc tttcaattct ttagggtaca       60
aattatcctt gcttcatttg tttctgcaat atcaagcact actgcatgat gtacatctgc     120
ggtggtacca taacttcgta tagcatacat tatacgaagt tatggtacct gcagaattca     180
tgacataagc ttggatccgt tcttcggacg cctcgtcaac accgtacgca gcctgccgg      240 ggccgcctgt gctccccaca gcctgccgg gcgttgctcc ctaaagccta ccccggccga     300
gctctgcttc tcgccgtctg cccggccag ctgtgctccc caccacctgc cctg           354
```